United States Patent
Prybolsky et al.

(10) Patent No.: US 11,756,656 B2
(45) Date of Patent: Sep. 12, 2023

(54) METHODS FOR TREATING AND PREVENTING SYMPTOMS OF ASTHMA WITH A CORTICOSTEROID PHARMACEUTICAL COMPOSITION

(71) Applicant: AstraZeneca UK Limited, Cambridge (GB)

(72) Inventors: Robert Peter Prybolsky, West Chester, PA (US); Judy Firor, Landenberg, PA (US)

(73) Assignee: ASTRAZENECA UK LIMITED, Cambridge (GB)

( * ) Notice: Subject to any disclaimer, the term of this patent is extended or adjusted under 35 U.S.C. 154(b) by 861 days.

(21) Appl. No.: 16/440,799

(22) Filed: Jun. 13, 2019

(65) Prior Publication Data
US 2019/0385710 A1    Dec. 19, 2019

Related U.S. Application Data

(60) Provisional application No. 62/685,213, filed on Jun. 14, 2018.

(51) Int. Cl.
| | | |
|---|---|---|
| G16H 10/20 | (2018.01) | |
| A61P 11/06 | (2006.01) | |
| G16H 70/40 | (2018.01) | |
| G06F 16/9038 | (2019.01) | |
| G06F 16/9035 | (2019.01) | |
| A61K 31/573 | (2006.01) | |

(Continued)

(52) U.S. Cl.
CPC .......... *G16H 10/20* (2018.01); *A61K 31/573* (2013.01); *A61K 31/58* (2013.01); *A61P 11/06* (2018.01); *G06F 16/9035* (2019.01); *G06F 16/9038* (2019.01); *G06Q 30/0637* (2013.01); *G16H 70/40* (2018.01)

(58) Field of Classification Search
CPC ............................. A61P 11/06; G06Q 30/0637
See application file for complete search history.

(56) References Cited

U.S. PATENT DOCUMENTS

| | | |
|---|---|---|
| 4,572,909 A | 2/1986 | Keravich et al. |
| 7,493,264 B1 | 2/2009 | Kelly et al. |

(Continued)

FOREIGN PATENT DOCUMENTS

| | | | |
|---|---|---|---|
| WO | WO 2010/041052 A1 | 4/2010 | |
| WO | WO-2019166997 A1 * | 9/2019 | ............ G06Q 30/00 |

OTHER PUBLICATIONS

FDA, Highlights of Prescribing Information—Glumetza, Apr. 2011, FDA, pp. 1-25. (Year: 2011).*

(Continued)

*Primary Examiner* — Robert A Sorey
(74) *Attorney, Agent, or Firm* — Brett A. Lovejoy; Andrew J. Antczak; Morgan, Lewis & Bockius LLP

(57) ABSTRACT

A method is provided for treating or preventing symptoms of asthma in a subject in need thereof by administering a corticosteroid pharmaceutical composition to a subject qualified for over-the-counter access to the corticosteroid pharmaceutical composition. In some embodiments, the corticosteroid pharmaceutical composition includes a class B corticosteroid, a glucocorticosteroid, budesonide, ciclesonide, fluticasone furoate, mometasone furoate, fluticasone propionate, or beclomethasone dipropionate.

26 Claims, 25 Drawing Sheets

(51) Int. Cl.
    *A61K 31/58*     (2006.01)
    *G06Q 30/0601*   (2023.01)

(56) References Cited

U.S. PATENT DOCUMENTS

| | | | |
|---|---|---|---|
| 2005/0108053 A1 | 5/2005 | Jones | |
| 2009/0125324 A1 | 5/2009 | Keravich et al. | |
| 2011/0034428 A1* | 2/2011 | Morrison | A61P 43/00 540/95 |
| 2011/0166876 A1 | 7/2011 | Chapman | |
| 2011/0178812 A1* | 7/2011 | Lindsay | G16H 10/20 705/2 |
| 2011/0181410 A1* | 7/2011 | Levinson | G16H 40/67 340/540 |
| 2012/0150562 A1* | 6/2012 | Lerner | G16H 70/20 705/2 |
| 2013/0218586 A1* | 8/2013 | Huser | G16H 20/10 705/2 |
| 2018/0165739 A1* | 6/2018 | Lawless | G16H 70/20 |
| 2022/0163546 A1* | 5/2022 | Huser | G16H 10/60 |

OTHER PUBLICATIONS

Wood, A. J. J., M.D., & Brass, Eric P,M.D., PhD. (2001). Changing the status of drugs from prescription to over-the-counter availability. The New England Journal of Medicine, 345(11), 810-816. Retrieved from https://dialog.proquest.com/professional/docview/223948307?accountid=131444 (Year: 2001).*

International Search Report and Written Opinion for International Patent Application No. PCT/US2019/037085, dated Oct. 14, 2019, 27 pages.

Ye et al., "A review on the Safety and Efficacy of Inhaled Corticosteroids in the Management of Asthma", Pulmonary therapy, vol. 3, No. 1, Apr. 20, 2017, pp. 1-8.

Daley-Yates et al., "Inhaled corticosteroids: potency, dose equivalence and therapeutic index: Inhaled corticosteroids potency and therapeutic index", British Journal of Clinical Pharmacology, vol. 80, No. 8, May 28, 2015, pp. 372-380.

Ramkumar, S. et al., Acta Cardiol. Sin., 32(6):631-39 (2016).

Barias S. FDA Considers a New Paradigm for Over-the-Counter Medications: More Power—but More Burdens—for Pharmacists and Pharmacies. P T. May 2012;37(5):300-5. PubMed PMID: 22876088; PubMed Central PMCID: PMC3411219.

Crestor, Full Prescribing Information, 2012, AstraZeneca Pharmaceuticals LP.

Dyer O., "FDA Rejects sale of over the counter Statins", BMJ, Jan. 22, 2005; 330(7484):164.

May 9, 2013, power point presentations from the Engelberg Center for Health Care Reform.

Pfizer Wants Atorvastatin Available Over the Counter—Medscape—Aug. 4, 2011, downloaded from the Internet Nov. 30, 2018.

PR Newswire Association, "Americans Should Pay More Attention to Over-the-Counter (OTC) medicine Labels According to New Survey", (Oct. 15, 2015) (citing McNeil Consumer Healthcare research).

Pulmicort Flexhaler (Budesonide Inhalation Powder) Prescribing Information, (AstraZeneca) Apr. 2010, [online], [retrieved on Feb. 28, 2021], Retrieved from the Internet: <URL: https://www.accessdata.fda.gov/drugsatfda_docs/label/2010/021949s006lbl.pdf>.

Arnuity Ellipta (fluticasone furoate inhalation powder) Prescribing Information, (GlaxoSmithKline) Aug. 2015, [online], [retrieved on Feb. 28, 2021], Retrieved from the Internet: <URL: https://www.accessdata.fda.gov/drugsatfda_docs/label/2014/205625s000lbl.pdf>.

Asmanex Twisthaler (mometasone furoate inhalation powder) Prescribing Information, (Schering Corporation) Jan. 2008, [online], [retrieved on Feb. 28, 2021], Retrieved from the Internet: <URL: https://www.accessdata.fda.gov/drugsatfda_docs/label/2008/021067s003lbl.pdf>.

Flovent Diskus (fluticasone propionate inhalation powder) Prescribing Information, (GlaxoSmithKline) Apr. 2014, [online], [retrieved on 2021-02-28], Retrieved from the Internet: <URL: https://www.accessdata.fda.gov/drugsatfda_docs/label/2014/020833s028lbl.pdf>.

QVAR (beclomethasone dipropionate HFA) Prescribing Information, (3M) Jul. 2014, [online], [retrieved on Feb. 28, 2021], Retrieved from the Internet: <URL: ttps://www.accessdata.fda.gov/drugsatfda_docs/label/2014/020911s025lbl.pdf>.

ALVESCO® (ciclesonide) Inhalation Aerosol Prescribing Information, (Sunovion Pharmaceuticals) 2012, [online], [retrieved on Feb. 28, 2021], Retrieved from the Internet: <URL: https://www.accessdata.fda.gov/drugsatfda_docs/label/2012/021658s006lbl.pdf>.

Both et al., Analysis of licensed over-the-counter (OTC) antibiotics in the European Union and Norway. Euro Surveill (2015).

Ferris et al., Over-the-Counter Antifungal Drug Misuse Associated With Patient-Diagnosed Vulvovaginal Candidiasis. Antifungal Drug Misuse. Obstetrics & Gynecology. vol. 99, No. 3, (2002) The American College of Obstetricians and Gynecologists.

Stomberg et al., Utilization effects of Rx-OTC switches and implications for future switches. Health. vol. 5, No. 10, 1667-1680 (2013).

Chang et al., Prescription to over-the-counter switches in the United States. Journal of Research in Pharmacy Practice. (2016).

D'Agostino et al., "General Cardiovascular Risk Profile for Use in Primary Care. The Framingham Heart Study" Circulation (2008): 743-753.

Hand, L. "FDA Panel Rejects OTC Use of Montelukast (Singulair Allergy)" https://www.medscape.com (May 2, 2014).

* cited by examiner

400

(402) A computer system for qualifying a human subject for over-the-counter delivery of a corticosteroid pharmaceutical composition for treating or preventing symptoms of asthma. The computer system comprises one or more processors and a memory. The memory comprises non-transitory instructions which, when executed by the one or more processor, perform a method.

(404) The corticosteroid pharmaceutical composition includes a class B corticosteroid.

(406) The corticosteroid pharmaceutical composition includes a glucocorticoid steroid.

(408) The corticosteroid pharmaceutical composition includes budesonide.

(410) The corticosteroid pharmaceutical composition includes a composition selected from the group consisting of ciclesonide, fluticasone furoate, mometasone furoate, fluticasone propionate, and beclomethasone dipropionate.

(412) Conduct a first survey of the subject thereby obtaining a first plurality of survey results.

(414) The first plurality of survey results comprise whether the subject has a dairy allergy, whether the subject is taking a steroid medication, an age of the subject, a pulmonary function status of the subject, whether the subject has a liver problem, whether the subject has an untreated infection, a surgery status of the subject, a bone density status of the subject, whether the subject has ever had cataracts or glaucoma, and whether the subject is taking a medication that interacts with the corticosteroid pharmaceutical composition.

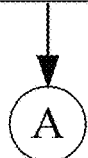

Fig. 4A

(416) Run all or a portion of the first plurality of survey results against a first plurality of filters of a first category class. When a respective filter in the first plurality of filters is fired, the subject is deemed not qualified for delivery of the corticosteroid pharmaceutical composition and the method is terminated without delivery of the corticosteroid pharmaceutical composition to the subject.

(418) The first plurality of filters comprises a first allergy filter that is fired at least when the first plurality of survey results indicates that the subject has a severe dairy allergy.

(420) The first plurality of filters comprises a first steroid medication filter that is fired at least when the first plurality of survey results indicates that the subject is taking a steroid medication.

(422) The first plurality of filters comprises an age filter.

(424) The age filter is fired when the first plurality of survey results indicates that the subject is less than eighteen years old (426) The first plurality of filters comprises a first pulmonary function filter that is fired at least when the first plurality of survey results indicates that the subject has compromised pulmonary function.

(428) The compromised pulmonary function, capable of firing the first pulmonary filter, is a forced expiratory volume measured over one second (FEV1) of no more than 80% of a predicted volume for the subject.

*(430)* The first plurality of survey results further comprises an asthma severity status of the subject. The first plurality of filters includes a first asthma filter that is fired when the first plurality of survey results indicates that the subject has severe asthma.

*(432)* The first plurality of survey results further comprises how frequently the subject experiences symptoms of asthma. An infrequency with which the subject experiences symptoms of asthma, which is capable of firing the first asthma filter, is less than twice a week. A frequency with which the subject experiences symptoms of asthma, which is capable of firing the first asthma filter, is more than six times a week.

*(434)* The first plurality of survey results further comprises how frequently symptoms of asthma disrupt the subject's sleep. An infrequency with which the subject's sleep is disrupted by symptoms of asthma, which is capable of firing the first asthma filter, is less than three times a month. A frequency with which the subject's sleep is disrupted by symptoms of asthma, which is capable of firing the first asthma filter, is more than four times a month.

*(436)* The first plurality of survey results further comprises how frequently the subject uses a rescue inhaler. An infrequency with which the subject uses a rescue inhaler, which is capable of firing the first asthma filter, is less than twice a week. A frequency with which the subject uses a rescue inhaler, which is capable of firing the first asthma filter, is more than six times a week.

*(438)* The first plurality of survey results further comprises how frequently the subject uses oral steroids. A frequency with which the subject has used oral steroids, which is capable of firing the first asthma filter, is more than once in the past year.

*(440)* The first plurality of survey results further comprises whether the subject is allergic to the corticosteroid pharmaceutical composition. The first plurality of filters includes a second allergy filter that is fired when the first plurality of survey results indicates that the subject is allergic to the corticosteroid pharmaceutical composition.

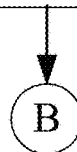

Fig. 4C

(442) Run all or a portion of the first plurality of survey results against a second plurality of filters of a second category class. When a respective filter in the second plurality of filters is fired, the subject is provided with a warning corresponding to the respective filter.

(444) The second plurality of filters comprises a first liver disease filter that is fired at least when the first plurality of survey results indicates that the subject has a liver problem.

(446) The second plurality of filters comprises a first infection filter that is fired at least when the first plurality of survey results indicates that the subject has a severe, untreated infection.

(448) The second plurality of filters comprises a first surgery filter that is fired at least when the first plurality of survey results indicates that the subject is planning on undergoing surgery.

(450) The second plurality of filters comprises a first bone density filter that is fired at least when the first plurality of survey results indicates that the subject has decreased bone mineral density.

(452) The second plurality of filters comprises a first ocular disease filter that is fired at least when the first plurality of survey results indicates that the subject has ever had cataracts or glaucoma.

(454) The second plurality of filters comprises a first drug interaction filter that is fired at least when the first plurality of survey results indicates that the subject is taking a medication that interacts with the corticosteroid pharmaceutical composition.

(456) The first drug interaction filter is fired when the first plurality of survey results indicates that the subject is taking a medication selected from the group consisting of a corticosteroid medicine, an anticonvulsant, an immunosuppressant, ketoconazole, a medicine for the liver, and a prescription anti-retroviral.

(458) The warning corresponding to a respective filter in the second plurality of filters comprises a prompt for the subject to indicate whether they have discussed the risk factor underlying the respective filter in the second plurality of filters that was fired with a health care provider. Acknowledgement is obtained from the subject when the subject indicates that they have discussed the risk factor underlying the respective filter in the second plurality of filters that was fired with a health care provider.

Fig. 4D

(460) Obtain acknowledgment from the subject for the warning issued to the subject by any filter in the second plurality of filters.

(462) Proceed with a fulfillment process when no filter in the first plurality of filters has been fired and the subject has acknowledged each warning associated with each filter in the second plurality of filters that was fired.

(464) The fulfillment process comprises storing an indication in a subject profile of an initial order for the corticosteroid pharmaceutical composition, communicating an over the counter drug facts label for the corticosteroid pharmaceutical composition to the subject, and authorizing, upon confirmation from the subject that the over the counter drug facts label has been received and read, provision of the corticosteroid pharmaceutical composition to the subject.

(466) Upon confirmation from the subject that the over the counter drug facts label has been received and read, the subject is authorized for provision of a dosage of from 90 mcg to 720 mcg of corticosteroid no more than twice per day.

(468) Upon confirmation from the subject that the over the counter drug facts label has been received and read, the subject is authorized for provision of a dosage of 180 mcg of corticosteroid no more than once per day.

(470) The fulfillment process further comprises storing a destination associated with the subject in the subject profile.

(472) The fulfillment process further comprises coordinating shipping of the corticosteroid pharmaceutical composition to a physical address associated with the subject.

(474) Responsive to receiving a re-order request from the subject for the corticosteroid pharmaceutical composition, performing a re-fulfillment procedure.

Fig. 4E

(476) Conduct a second survey of the subject thereby obtaining a second plurality of survey results.

(478) The second plurality of survey results comprises whether the subject has developed a dairy allergy since receiving their last provision of the corticosteroid pharmaceutical composition, whether the subject is taking a steroid medication, a pulmonary status function of the subject, whether the subject has observed an improvement in the symptoms of asthma since receiving their last provision of the corticosteroid pharmaceutical composition, whether the subject has or has been in contact with someone having chicken pox, measles, or tuberculosis since receiving their last provision of the corticosteroid pharmaceutical composition, whether the subject has developed symptoms of an infections ince receiving their last provision of the corticosteroid pharmaceutical composition, a vision status of the subject, an oral health status of the subject, whether the subject has developed a liver problem since receiving their last provision of the corticosteroid pharmaceutical composition, whether the subject has developed an infection since receiving their last provision of the corticosteroid pharmaceutical composition, a surgery status of the subject, a bone density status of the subject, whether the subject has developed cataracts or glaucoma since receiving their last provision of the corticosteroid pharmaceutical composition, and whether the subject is taking a medication that interacts with the corticosteroid pharmaceutical composition.

(480) Run all or a portion of the second plurality of survey results against a third plurality of filters of the first category class. When a respective filter in the third plurality of filters is fired, the subject is deemed not qualified for the corticosteroid pharmaceutical composition and the re-fulfillment process is terminated without delivery of the corticosteroid pharmaceutical composition to the subject.

(482) The third plurality of filters comprises a third allergy filter that is fired at least when the second plurality of survey results indicates that the subject has a severe dairy allergy.

(484) The third plurality of filters comprises a second steroid medication filter that is fired at least when the second plurality of survey results indicates that the subject is taking a steroid medication.

(486) The third plurality of filters comprises a second pulmonary function filter that is fired at least when the second plurality of survey results indicates that the subject has compromised pulmonary function.

(488) The compromised pulmonary function, capable of firing the second pulmonary filter, is a forced expiratory volume measured over one second (FEV1) of no more than 80% of a predicted volume for the subject.

Fig. 4F (480 continued)

(490) The third plurality of filters comprises a second asthma filter that is fired when the second plurality of survey results indicates that the subject has not observed an improvement in symptoms of asthma.

(492) The second plurality of survey results further comprises how frequently the subject experiences symptoms of asthma. A frequency with which the subject experiences symptoms of asthma, which is capable of firing the second asthma filter, is more than twice a week.

(494) The second plurality of survey results further comprises how frequently symptoms of asthma disrupt the subject's sleep. A frequency with which the subject's sleep is disrupted by symptoms of asthma, which is capable of firing the second asthma filter, is more than twice a month.

(496) The second plurality of survey results further comprises how frequently the subject uses a rescue inhaler. A frequency with which the subject uses a rescue inhaler, which is capable of firing the second asthma filter, is more than twice a week.

(498) The second plurality of survey results further comprises how frequently the subject uses oral steroids. A frequency with which the subject has used oral steroids, which is capable of firing the second asthma filter, is more than once in the past year.

Fig. 4G

(500) Run all or a portion of the second plurality of survey results against a fourth plurality of filters of the second category class. When a respective filter in the fourth plurality of filters is fired, the subject is provided with a warning corresponding to the respective filter.

(502) The fourth plurality of filters comprise a viral contact filter that is fired at least when the second plurality of survey results indicates that the subject has or has been in contact with someone having chicken pox, measles, or tuberculosis since receiving their last provision of the corticosteroid pharmaceutical composition, a symptoms of infection filter that is fired at least when the second plurality of survey results indicates that the subject has a symptom of infection, a vision deterioration filter that is fired at least when the second plurality of survey results indicates that the subject has experienced a change in vision since receiving their last provision of the corticosteroid pharmaceutical composition, an oral health filter that is fired at least when the second plurality of survey results indicates that the subject has experienced redness or white-colored patches in their mouth or throat since receiving their last provision of the corticosteroid pharmaceutical composition, a second liver disease filter that is fired at least when the second plurality of survey results indicates that the subject has a liver problem, a second infection filter that is fired at least when the second plurality of survey results indicates that the subject has a severe, untreated infection, a second surgery filter that is fired at least when the second plurality of survey results indicates that the subject is planning on undergoing surgery, a second bone density filter that is fired at least when the second plurality of survey results indicates that the subject has decreased bone mineral density, a second ocular disease filter that is fired at least when the second plurality of survey results indicates that the subject has developed cataracts or glaucoma since receiving their last provision of the corticosteroid pharmaceutical composition, and a second drug interaction filter that is that is fired at least when the second plurality of survey results indicates that the subject is taking a medication that interacts with the corticosteroid pharmaceutical composition.

(504) The second plurality of survey results further comprises whether the subject has experienced a side effect from the corticosteroid pharmaceutical composition. The fourth plurality of filters further comprises a side effect filter that is fired at least when the second plurality of survey results indicates that the subject has experienced, since receiving their last provision of the corticosteroid pharmaceutical composition, a side effect selected from the group consisting of a sore nose, a sore throat, nausea, hay fever, an upper respiratory tract viral infection, gastroenteritis, and an ear infection.

(506) When a respective filter in the third plurality of filters or fourth plurality of filters is fired, store a record associated with the firing of the respective filter in an adverse event profile comprising records of filter firing events associated with a plurality of subjects.

Fig. 4H

Do you have an allergy to dairy? ⎯550

⎯552

Budesonide is known to contain traces levels of milk proteins.

Please consult with your doctor before taking Budesonide OTC.

Do you have decreased bone mineral density? ⎯554

⎯556

FEV1 Level

558

Are you taking any of the following:

A corticosteroid medication

An anti-convulsant

An immunosuppressant

Ketoconazole

A medicine for the liver

A prescription strength anti-retroviral

Fig. 5E

Budesonide OTC may not be right for you. Based on your answers, it is important to talk to your doctor about potential risks of taking Budesonide OTC. It may be helpful to have your summary of answers when talking to your doctor.

— 602

Has your doctor said it is OK for you to take Budesonide OTC?

Yes

No, View/Print Summary

METHODS FOR TREATING AND PREVENTING SYMPTOMS OF ASTHMA WITH A CORTICOSTEROID PHARMACEUTICAL COMPOSITION

CROSS REFERENCE TO RELATED APPLICATIONS

This application claims priority to U.S. Provisional Patent Application Ser. No. 62/685,213, filed Jun. 14, 2018, which is hereby incorporated by reference in its entirety.

TECHNICAL FIELD

The present disclosure relates generally to methods for treating and preventing symptoms of asthma by administering an over-the-counter corticosteroid pharmaceutical composition to a subject in need thereof, who has been qualified for over-the-counter access to the composition.

BACKGROUND

Even though asthma is the one of the most common diseases worldwide, with proper care it's symptoms are some of the most preventable. CDC Vital Signs (2011), Asthma in the US. Center for Disease Control and Prevention. As of 2016, according to the CDC, 1 in 13 adults in the U.S. is inflicted with asthma. Centers for Disease Control, Uncontrolled Asthma among Persons with Asthma, Print (2016). Of an approximately 25 million U.S. citizens that have been told by a health professional that they have asthma, 50% of these citizens are aware that they have asthma, yet are not being treated. Each year, uncontrolled asthma costs an estimated additional $8750 per person annually in direct and indirect medical expenses compared to individuals that have controlled asthma. Casciano, J. et al., Clinical and Economic Burden of Uncontrolled Asthma and Elevated Eosinophil Levels, Am J Respir Crit Care Med, 193 (2016).

Asthma can be managed, for example, using corticosteroids, which are well established prescription pharmaceuticals used to treat asthma and prevent asthma symptoms. For instance, the efficacy of budesonide, which was first approved in the U.S. for the treatment of asthma in 1981, has been demonstrated in numerous double-blind, placebo-controlled, randomized studies conducted throughout the recent decades. See, O'Connell, Efficacy of Budesonide in Moderate to Severe Asthma, Clin Ther., 24(6), 2002; Eigen H., Efficacy of Budesonide in Inhaled Corticosteroid-naïve Patients and Patients with Mild Persistent Asthma, Clin. Ther., 24(7), 2002. However, access to corticosteroids is restricted by the requirement for a prescription. Unfortunately, long-term trends demonstrate many people avoid prescription medications, including corticosteroids.

One approach to making corticosteroids more accessible is to make them available without a prescription, e.g., over the counter ("OTC"). There are a variety of health benefits derived from switching a drug from prescription to OTC including generating wider availably to therapies, providing a greater number of therapeutic approaches, providing direct and rapid access to treatments, providing patients with an active role in their own health care, and allowing patients to become self-reliant in preventing and relieving minor symptoms or conditions (World Health Organization, 2000, "Guidelines for the Regulatory Assessment of Medicinal Products for use in Self-Medication," Print). Given the large number of individuals with uncontrolled asthma, providing access to OTC corticosteroids would provide significant societal health benefits.

However, switching distribution of a pharmaceutical from prescription-only to OTC creates a significant risk that the patient population will be unable to appropriately self-select themselves for safe use of the pharmaceutical and then self-medicate with the pharmaceutical in a responsible manner. The manifestations embodied within these concerns include incorrect self-diagnosis, incorrect drug-qualification, unrecognized drug-drug interactions (DDI), unanticipated adverse drug reactions and/or side-effects, improper dosing and/or administration, masking of a disease, addiction, inappropriate drug dependency, substance abuse, and patient delay in seeking necessary medical attention. Ruiz et al., Current Drug Safety, 5(4):315 (2010).

Because corticosteroids cause adverse effects in certain patients, the population receiving them should be carefully selected and monitored. This is why corticosteroid distribution has traditionally been regulated through exclusive prescription access. In order to ensure the safety of OTC distribution of corticosteroids, prospective patients must effectively self-select themselves for the corticosteroids. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey," Oct. 15 (2015) (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Currently, there are two regulatory pathways for legal marketing of an OTC drug in the United States. In the first pathway, marketing occurs in compliance with an OTC drug monograph, that sets regulatory standards for non-prescription drugs that are not covered by human drug applications, e.g., a New Drug Application (NDA) or Abbreviated New Drug Application (ANDA). An OTC monograph is created as a result of a three phase OTC drug review by the FDA. In phase I of the review, an advisory review panel determines whether ingredients in the proposed OTC composition could be generally recognized as safe and effective for use in self-treatment. In the second pathway, marketing occurs under the authority of an approved product-specific new drug application (NDA), or an abbreviated new drug application (ANDA). In order to support an over-the-counter label for a drug for which regulatory approval is being sought through an NDA, a consumer research study is required to assess the consumer's ability to select and deselect themselves as appropriate users of the drug, based on the proposed labeling for the drug. Oliver, A., Regulatory Rapporteur, 10(3):4-9 (2013), which is incorporated by reference herein.

However, attempts at switching distribution of respiratory drugs having potentially far-reaching benefits for societal health, from prescription-only to an OTC model, have failed, in large part due to concerns over inappropriate patient selection and medication. For instance, in 2014, FDA advisory committee panels rejected two respiratory medications for over-the-counter distribution, montelukast and epinephrine mist. Hand L., FDA Panel Rejects OTC Use of Montelukast (Singulair Allergy), Medscape, (2014); Brown T., FDA Panels: Primatene HFA Inhaler Not Recommended for Asthma, Medscape, (2014). While the panels found these medications efficacious, the rejections stemmed from concerns regarding each medication's safety of use. Id. The committees described major concerns for potential nonprescription use of both montelukast and epinephrine mist as having a high risk of being used off-label and the complexity of the labeling being too difficult for the average adult to understand. Id.

Other examples of the inability to switch important medications from a prescription distribution model include the repeated failure of companies to bring statins, used to treat high cholesterol levels, over-the-counter. For instance, applications for sale of over the counter lovastatin have been rejected by the FDA in 2000, 2005, and 2007. For instance, in the 2005 proposal to permit over the counter sales of lovastatin, an expert advisory panel at the FDA was concerned by a marketing study performed to support the proposal in which, after reviewing data from the marketing study, the panel concluded that 45% of the purchases made by subjects in the marketing study were inappropriate for a variety of reasons, including subject age, subject's lack of knowledge about their condition, and contraindications associated with their condition. Dyer O., BMJ, 330(7484): 164 (2005). In 2007, the board again concluded that the ability of consumers to appropriately self-select and to adequately comply with chronic MEVACOR® therapy without the intervention of a physician had not been demonstrated. Division of Metabolic and Endocrine Drug Products, 2005, "NDA 21-213 Non-prescription MEVACOR® 20 mg Joint Advisory Committee Meeting."

Similarly, efforts to switch LIPITOR® from prescription-only to OTC status were announced in 2011. Sett OTC bulletin, 16 Nov. 2011, page 7. However, this effort was abandoned in 2014 when a phase 3 "actual use" trial, intended to simulate the OTC use of LIPITOR® (atorvastatin calcium) 10 mg, failed to meet its primary objectives on the basis that patient compliance with the direction to check their low-density lipoprotein cholesterol (LDL-C) level and, after checking their LDL-C level, take appropriate action based on their test results was unsatisfactory. Pfizer Inc., "Pfizer Reports Second-Quarter 2015 Results," (2015).

In fact, in the nearly two decades since Bristol-Myers Squibb and Merck & Co first failed in their attempts to switch PRAVACHOL® and lovastatin, respectively, to OTC, a statin has never been granted OTC status in the United States. This is despite that nearly ⅙th of the adult population in the U.S. is eligible for cholesterol-lowering medications, under the current guidelines, but are not taking anything.

The information disclosed in this Background section is only for enhancement of understanding of the general background of the invention and should not be taken as an acknowledgment or any form of suggestion that this information forms the prior art already known to a person skilled in the art.

SUMMARY

Given the above background, what is needed in the art are systems and methods for qualifying a human subject for delivery of a corticosteroid pharmaceutical composition over-the-counter to treat and/or prevent symptoms of asthma.

The present disclosure addresses the need in the art for systems and methods configured for qualifying a human subject for over-the-counter delivery of corticosteroid pharmaceutical composition (e.g., budesonide) thereby treating or preventing symptoms of asthma. In the present disclosure, systems and methods are provided for over-the-counter delivery of a corticosteroid pharmaceutical composition to a subject. Survey results from the subject are run against a first plurality of filters. When a filter in the first plurality is fired, the subject is deemed not qualified for delivery of the corticosteroid pharmaceutical composition. The survey results are also run against a second plurality of filters. When a respective filter in the second plurality is fired, the subject is provided with a corresponding warning. The method proceeds to a fulfillment process when no filter in the first plurality of filters is fired and the subject has acknowledged each warning associated with each fired filter in the second plurality of filters. The fulfillment process stores the composition order, communicates a drug facts label for the corticosteroid pharmaceutical composition to the subject, and authorizes, upon subject confirmation that the label has been read, provision of corticosteroid pharmaceutical composition to the subject.

Accordingly, one aspect of the present disclosure provides a method for qualifying a subject for over-the-counter delivery of a corticosteroid pharmaceutical composition thereby treating or preventing symptoms of asthma of the subject. The method includes conducting a first survey of the subject in order to obtain a variety of survey results. In some embodiments, the survey results indicate one or more of: whether the subject is already taking a steroid medication, an age of the subject, a pulmonary function status of the subject, a frequency with which the subject experiences symptoms of asthma, whether the subject has an untreated infection, a surgery status of the subject, a bone density status of the subject, and whether the subject has ever had cataracts or glaucoma.

The method also includes running all or a portion of the survey results against a first plurality of filters of a first category class, corresponding to contraindications associated with the corticosteroid pharmaceutical composition. When a respective filter in the first plurality of filters is fired, the subject is deemed not qualified for delivery of the corticosteroid pharmaceutical composition, and the method is then terminated accordingly without delivery of the corticosteroid pharmaceutical composition to the subject. In some embodiments, the first plurality of filters includes one or more of a steroid medication filter, an age filter, a pulmonary function filter, and an asthma severity filter.

The method also includes running all or a portion of the survey results against a second plurality of filters of a second category class, corresponding to risk factors associated with the corticosteroid pharmaceutical composition. When a respective filter in the second plurality of filters is fired, the subject is provided with a warning corresponding to the respective filter. In some embodiments, the second plurality of filters includes one or more of an infection filter, a surgery filter, a bone density filter, and an ocular disease filter. However, unlike filters in the first plurality of filters, filters in the second plurality of filters do not automatically terminate the process without delivery of the corticosteroid pharmaceutical composition to the subject.

The method continues by obtaining acknowledgment from the subject for the warning issued to the subject by any filter in the second plurality of filters.

The method continues by proceeding with a fulfillment process when no filter in the first plurality of filters has been fired and the subject has acknowledged each warning associated with each filter in the second plurality of filters that was fired.

In some embodiments, the fulfillment process includes storing an indication in a subject profile of an initial order for the corticosteroid pharmaceutical composition, communicating an over-the-counter drug label for the corticosteroid pharmaceutical composition, and authorizing, upon confirmation from the subject that the over-the-counter drug label has been received and read, provision of the corticosteroid pharmaceutical composition to the subject.

In some embodiments, e.g., where the corticosteroid pharmaceutical composition includes budesonide, the survey results also indicates whether the subject has a dairy allergy, whether the subject has a liver problem, and whether the subject is taking a medication that interacts with the corticosteroid pharmaceutical composition, and the first plurality of filters also includes an allergy filter, and the second plurality of filters also includes a liver disease filter and a drug interaction filter.

In some embodiments, e.g., where the corticosteroid pharmaceutical composition includes mometasone furoate, the survey results also indicates whether the subject has a dairy allergy, whether the subject has a liver problem, and whether the subject is taking a medication that interacts with the corticosteroid pharmaceutical composition, and the first plurality of filters also includes an allergy filter, and the second plurality of filters also includes a liver disease filter and a drug interaction filter.

In some embodiments, e.g., where the corticosteroid pharmaceutical composition includes fluticasone furoate, the survey results also indicates whether the subject has a dairy allergy, whether the subject has a liver problem, and whether the subject is taking a medication that interacts with the corticosteroid pharmaceutical composition, and the first plurality of filters also includes an allergy filter, and the second plurality of filters also includes a liver disease filter and a drug interaction filter.

In some embodiments, e.g., where the corticosteroid pharmaceutical composition includes fluticasone propionate, the survey results also indicates whether the subject has a dairy allergy and the first plurality of filters also includes an allergy filter.

In some embodiments, the corticosteroid pharmaceutical composition includes a class B corticosteroid. In some embodiments, the corticosteroid pharmaceutical composition includes a glucocorticosteroid.

In some embodiments, the corticosteroid pharmaceutical composition includes budesonide, or a pharmaceutically acceptable salt thereof. In some embodiments, the corticosteroid pharmaceutical composition includes a corticosteroid selected from ciclesonide, fluticasone furoate, mometasone furoate, fluticasone propionate, beclomethasone dipropionate, and a pharmaceutically acceptable salt thereof.

In one aspect, the present disclosure provides a method for qualifying a subject (e.g., a subject who was previously qualified to receive a provision of the corticosteroid pharmaceutical composition) for a re-order of the corticosteroid pharmaceutical composition (e.g., which is optionally performed in conjunction with a method for qualifying the subject for a first order of the corticosteroid pharmaceutical composition). The method includes a re-fulfillment procedure that includes conducting a second survey of the subject in order to obtain second survey results. In some embodiments, the second survey results indicate one or more of: whether the subject has begun taking a steroid medication, a pulmonary function status of the subject, whether the subject has observed an improvement in the symptoms of asthma since receiving their last provision of the corticosteroid pharmaceutical composition, whether the subject has or has been in contact with someone having chicken pox, measles, or tuberculosis since receiving their last provision of the corticosteroid pharmaceutical composition, whether the subject has experienced symptoms of infection since receiving their last provision of the corticosteroid pharmaceutical composition, whether the subject has experienced deterioration in vision since receiving their last provision of the corticosteroid pharmaceutical composition, an oral health status of the subject, whether the subject has developed an infection since receiving their last provision of the corticosteroid pharmaceutical composition, a surgery status of the subject, a bone density status of the subject, and whether the subject has developed cataracts or glaucoma since receiving their last provision of the corticosteroid pharmaceutical composition.

The method also includes running all or a portion of the second survey results against a third plurality of filters of the first category class, corresponding to contraindications associated with the corticosteroid pharmaceutical composition. When a respective filter in the third plurality of filters is fired, the subject is deemed not qualified for the corticosteroid pharmaceutical composition, and the re-fulfillment process is terminated without delivery of the corticosteroid pharmaceutical composition to the subject. In some embodiments, the third plurality of filters includes a steroid medication filter, a pulmonary function filter, and an asthma reduction filter.

The method also includes running all or a portion of the second survey results against a fourth plurality of filters of the second category class, corresponding to risk factors associated with the corticosteroid pharmaceutical composition. When a respective filter in the fourth plurality of filters is fired the subject is provided with a warning corresponding to the respective filter. In some embodiments, the fourth plurality of filters includes one or more of: an infectious disease contact filter, a symptoms infection filter, a vision deterioration filter, an oral health filter, an infection filter, a surgery filter, a bone density filter, and an ocular disease filter.

The method continues by obtaining acknowledgment from the subject for the warning issued to the subject by any filter in the fourth plurality of filters. When the re-fulfillment process is not already terminated by the firing of a filter in the third plurality of filters and the subject has acknowledged each warning associated with each filter in the fourth plurality of filters that was fired, the method continues with a re-fulfillment procedure.

In some embodiments, the method includes storing an indication in the subject profile of a re-order for the corticosteroid pharmaceutical composition, communicating an over-the-counter drug facts label for the corticosteroid pharmaceutical composition to the subject, and authorizing, upon confirmation from the subject that the over-the-counter drug facts label has been received and read, a re-order provision of the corticosteroid pharmaceutical composition to the subject.

BRIEF DESCRIPTION OF THE DRAWINGS

FIGS. 4A, 4B, 4C, 4D, 4E, 4G, 4H, and 4I collectively provide a flow chart of processes for qualifying a human subject for over-the-counter delivery of a corticosteroid pharmaceutical composition to treat or prevent symptoms of asthma, where elements in dashed boxes are optional, in accordance with various embodiments of the present disclosure.

FIGS. 5A, 5B, 5C, 5D, and 5E illustrate example survey questions for obtaining survey results, in accordance with an embodiment of the present disclosure.

Figure 1:
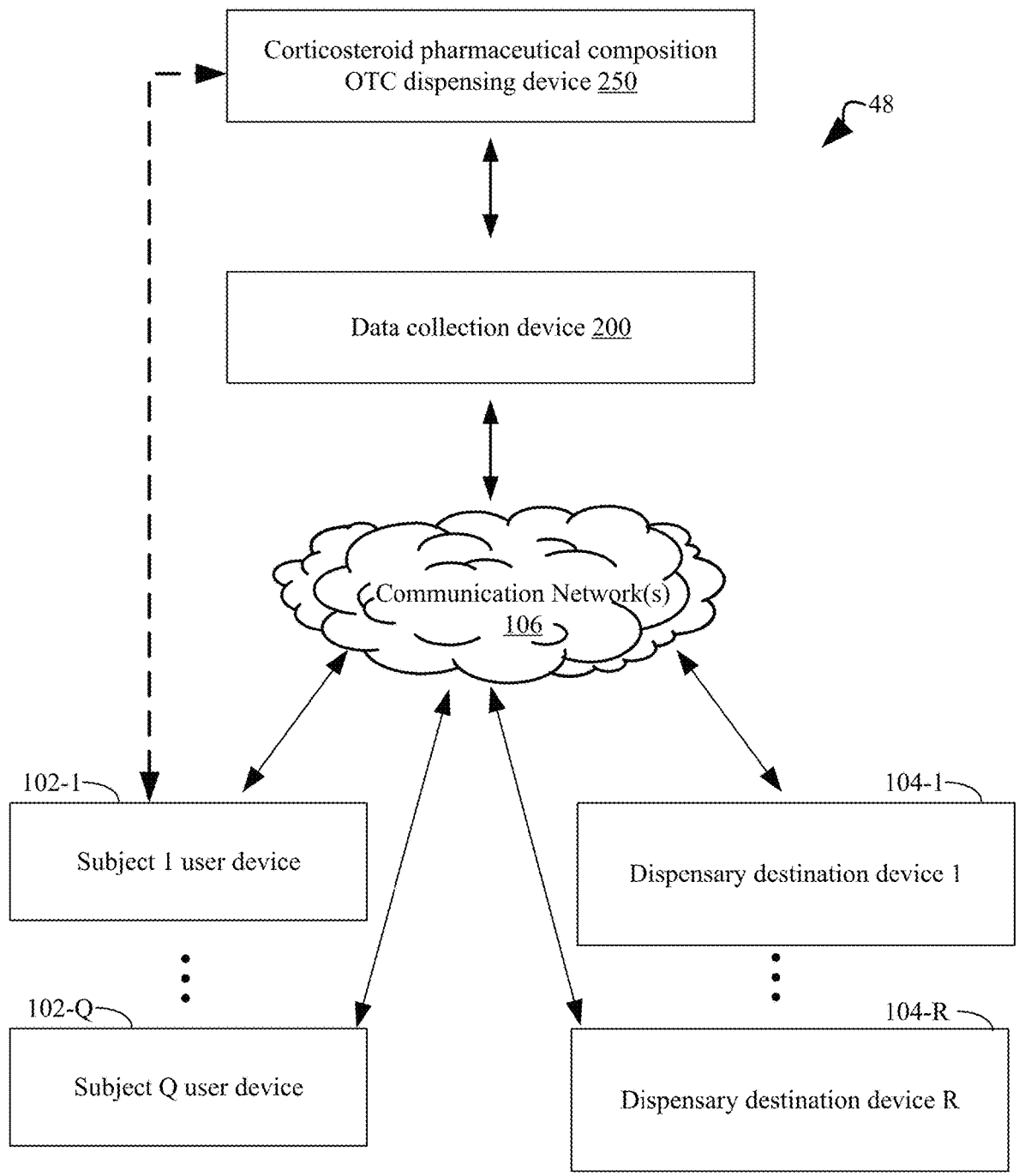
FIG. 1 illustrates an exemplary system topology that includes a corticosteroid pharmaceutical composition over-the-counter (OTC) dispensing device for qualifying a human subject for over-the-counter delivery of a corticosteroid pharmaceutical composition to treat or prevent symptoms of asthma, a data collection device for collecting subject data, one or more user devices associated with human subjects, and one or more dispensary destinations for distributing the corticosteroid pharmaceutical composition over-the-counter, where the above-identified components are interconnected, optionally through a communications network, in accordance with an embodiment of the present disclosure.

In the figures, reference numbers refer to the same or equivalent parts of the present invention throughout the several figures of the drawing.

DETAILED DESCRIPTION

Asthma is a growing health problem, in the United States and worldwide. Although symptoms of asthma can be effectively treated and/or prevented using established pharmaceutical compositions, access to these drugs is hindered by to the requirement for a prescription, as many individuals do not have adequate access and/or avoid the healthcare system for a variety of reasons. Accordingly, many people are not managing their asthma or conditions related to asthma appropriately. While over-the-counter alternatives to these prescription pharmaceuticals would increase access to these compositions, thereby improving population management of asthma around the world, patients often have difficulty self-selecting themselves for an appropriate over-the-counter medication. Because inappropriate use of these drugs can result in ineffective treatment and/or serious side-effects, better methods for selecting for, and treating patients with, other-the-counter asthma medications are needed. The present disclosure provides, among other aspects, methods, systems, and computer readable media that solve these problems.

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over-the-counter" means to provide by retail purchase, subject to the constraints disclosed herein, but without a prescription or license from a physician or medical practitioner.

As used herein, the term "pharmaceutical compound" refers to any physical state of a material. Pharmaceutical compounds include capsules, tablets, liquids, topical formulations, and inhaled formulations.

As used herein, the term "contraindication" refers to a condition that makes a treatment, e.g., over-the-counter use of a corticosteroid pharmaceutical composition, inadvisable. Contraindications include physical characteristics of a subject, e.g., is not a male or has a liver disease, and contemporaneous drug use, e.g., corticosteroid pharmaceutical composition use. In the present context, identification of a contraindication fires a filter of a first category class, which prevents authorizing provision of a corticosteroid pharmaceutical composition, in accordance with some implementations of the methods, systems, and software disclosed herein.

As used herein, the term "risk factor" refers to a condition that makes a treatment, e.g., over-the-counter use of a corticosteroid pharmaceutical composition, possibly inadvisable. Risk factors include physical characteristics of a subject, e.g., a bone density measurement, and contemporaneous drug use, e.g., use of a steroid medication. In the present context, identification of a risk factor fires a filter of a second category class, which prevents authorizing provision of a corticosteroid pharmaceutical composition without confirmation that the subject has discussed the risk factor with a medical professional, in accordance with some implementations of the methods, systems, and software disclosed herein.

As used herein, "drug interactions," e.g., with a corticosteroid, include pharmacokinetic drug interactions and pharmacodynamics drug interactions. Generally, a pharmacokinetic drug interaction is an interaction between two drugs (e.g., a corticosteroid and a second drug) that result in alterations in the absorption, transport, distribution, metabolism, and/or excretion of either drug. Generally, a pharmacokinetic drug interaction is an interaction between two drugs (e.g., a corticosteroid and a second drug) that result in a direct change in the effect or either drug. For a more comprehensive summary of pharmacokinetic drug interactions and pharmacodynamics drug interactions, see, Cascorbi, I, Dtsch Arztebl Int., 109(33-34):546-55 (2012), the content of which is hereby incorporated by reference.

In the context of the present disclosure, classification of a condition as either a contraindication or a risk factor is specific to a particular identity and dose of a corticosteroid pharmaceutical composition being authorized for over-the-counter use. Classification of a particular condition, e.g., contemporaneous corticosteroid pharmaceutical composition use, may vary between different corticosteroid pharmaceutical compositions (e.g., it may be classified as a contraindication for a first corticosteroid, a risk factor for a second corticosteroid, and/or neither for a third corticosteroid). Likewise, a particular condition may be classified as a contraindication for use of a particular corticosteroid at a first over-the-counter dosage, classified as a risk factor for the same particular corticosteroid at a second (e.g., lower) over-the-counter dosage, and/or classified as neither for the same particular corticosteroid at a third (e.g., lowest) over-the-counter dosage.

As used herein, whether a subject "has developed" a condition since receiving their last provision of a corticosteroid refers to both conditions that are new to the subject, i.e., a condition that the subject did not have at the time they received their last provision of the corticosteroid, and conditions that have been newly diagnosed, regardless of whether the condition existed when the subject received their last provision of the corticosteroid, i.e., a condition that the subject was not aware of when they received their last provision of the corticosteroid.

In one aspect, the present disclosure conducts a survey of a subject to obtain survey results in order to determine if the subject qualifies for an over-the-counter (OTC corticosteroid pharmaceutical composition for the treatment or prevention of symptoms of asthma. The survey results are used as the basis for running filters of a first category class. If the triggering conditions of any of the filters in the first category class are fired, the subject does not qualify for the OTC corticosteroid pharmaceutical composition. The survey results are also used as the basis for running filters of a second category class. If the triggering conditions of any of the filters in the second category class are fired, the subject is provided with warning messages associated with the respective filters of the second category class that have been fired. If none of the filters in the first category class are fired and the subject successfully addresses the warning messages associated with the respective filters of the second category class that have been fired, a fulfillment process is initiated for OTC delivery of the corticosteroid pharmaceutical composition.

FIG. 1 illustrates an example of an integrated system 48 for conducting one or more surveys of subjects in order to qualifying the subjects for OTC delivery of a corticosteroid pharmaceutical composition. The integrated system 48 includes one or more connected user devices 102. The user devices 102 are configured for entering survey data and making requests for the corticosteroid pharmaceutical composition. The system 48 also includes one or more dispensary destination devices 104 that are configured to receive instructions in order to provide the corticosteroid pharmaceutical composition to qualifying subjects. Furthermore, the system 48 includes a corticosteroid pharmaceutical composition over-the-counter (OTC) dispensing device 250 and one or more data collection devices 200 that are configured for collecting subject data.

Throughout the present disclosure, the data collection device 200 and the corticosteroid pharmaceutical composition OTC dispensing device 250 will be referenced as separate devices solely for purposes of clarity. That is, the disclosed functionality of the data collection device 200 and the disclosed functionality of the corticosteroid pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the corticosteroid pharmaceutical composition OTC dispensing device 250 are contained in a single device.

With the integrated system 48, survey results from the subjects are run against a first plurality of filters (e.g., filter 216-1, filter 216-2, filter 216-3, etc.) When a filter in the first plurality of filters (e.g., filter 216) is fired for a respective subject, the respective subject is deemed not qualified for the corticosteroid pharmaceutical composition. The survey results are also run against a second plurality of filters (e.g., filter 222-1, filter 222-2, filter 222-3, etc.). When a respective filter in the second plurality is fired for a respective subject, the respective subject is provided with a warning (e.g., filter warning 226) associated with the respective filter. In some embodiments, the survey results are run against the first plurality of filters and the second plurality of filters concurrently. In some embodiments the survey results are run against the first plurality of filters and then against the second plurality of filters. The method enabled by the integrated system 48 proceeds to a fulfillment process when no filter in the first plurality fires and the subject has acknowledged, or otherwise successfully addressed, each warning associated with each filter in the second plurality of filters that fired. As part of the fulfillment process, the composition order is stored (e.g., in a user profile 234 associated with the subject to receive the drug), a drug facts label (e.g., drug facts label 230) for the corticosteroid is communicated to the qualifying subject. Upon subject confirmation that the label has been read, authorization is granted to dispense the corticosteroid.

Referring to FIG. 1, the corticosteroid pharmaceutical composition OTC dispensing device 250 qualifies a subject for over-the-counter delivery of a corticosteroid pharmaceutical composition to treat or prevent symptoms of asthma. To accomplish this, the data collection device 200, which is in electrical communication with the corticosteroid OTC dispensing device 250, receives survey results originating from one or more user devices 102 associated with corresponding subjects. In some embodiments, the data collection device 200 receives such survey results directly from the user devices 102. For instance, in some embodiments the data collection device 200 receives this data wirelessly through radio-frequency signals. In some embodiments, such signals are in accordance with an 802.11 (Wi-Fi), Bluetooth, or ZigBee standard. In some embodiments, the data collection device 200 receives such data directly, analyzes the data, and passes the analyzed data to the corticosteroid pharmaceutical composition OTC dispensing device 250.

In some embodiments, the data collection device 200 and/or the corticosteroid pharmaceutical composition OTC dispensing device 250 is not proximate to the subject and/or does not have wireless capabilities or such wireless capabilities are not used for the purpose of acquiring survey results. In some embodiments, a communication network 106 may be used to survey questions (e.g., survey questions 208, 212) from the corticosteroid pharmaceutical composition OTC dispensing device 250 to user devices 102 and the answers to such survey questions from the user devices 102 to the data collection device 200 and/or the corticosteroid pharmaceutical composition OTC dispensing device 250. Further, in some embodiments the communication network 106 is used to communicate authorization to dispense the corticosteroid survey questions from the corticosteroid pharmaceutical composition OTC dispensing device 250 to dispensary destination devices 104.

Examples of networks 106 include, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the corticosteroid pharmaceutical composition OTC dispensing device 250. Further, the data collection device 200 and/or the corticosteroid pharmaceutical composition OTC dispensing device 250 may constitute a portable electronic device, a server computer, or in fact constitute several computers that are linked together in a network, be a virtual machine in a cloud computing context, be a container in a cloud computer context, or a combination thereof. As such, the exemplary topology shown in FIG. 1 merely serves to describe the features of an embodiment of the present disclosure in a manner that will be readily understood to one of skill in the art.

Figure 2:
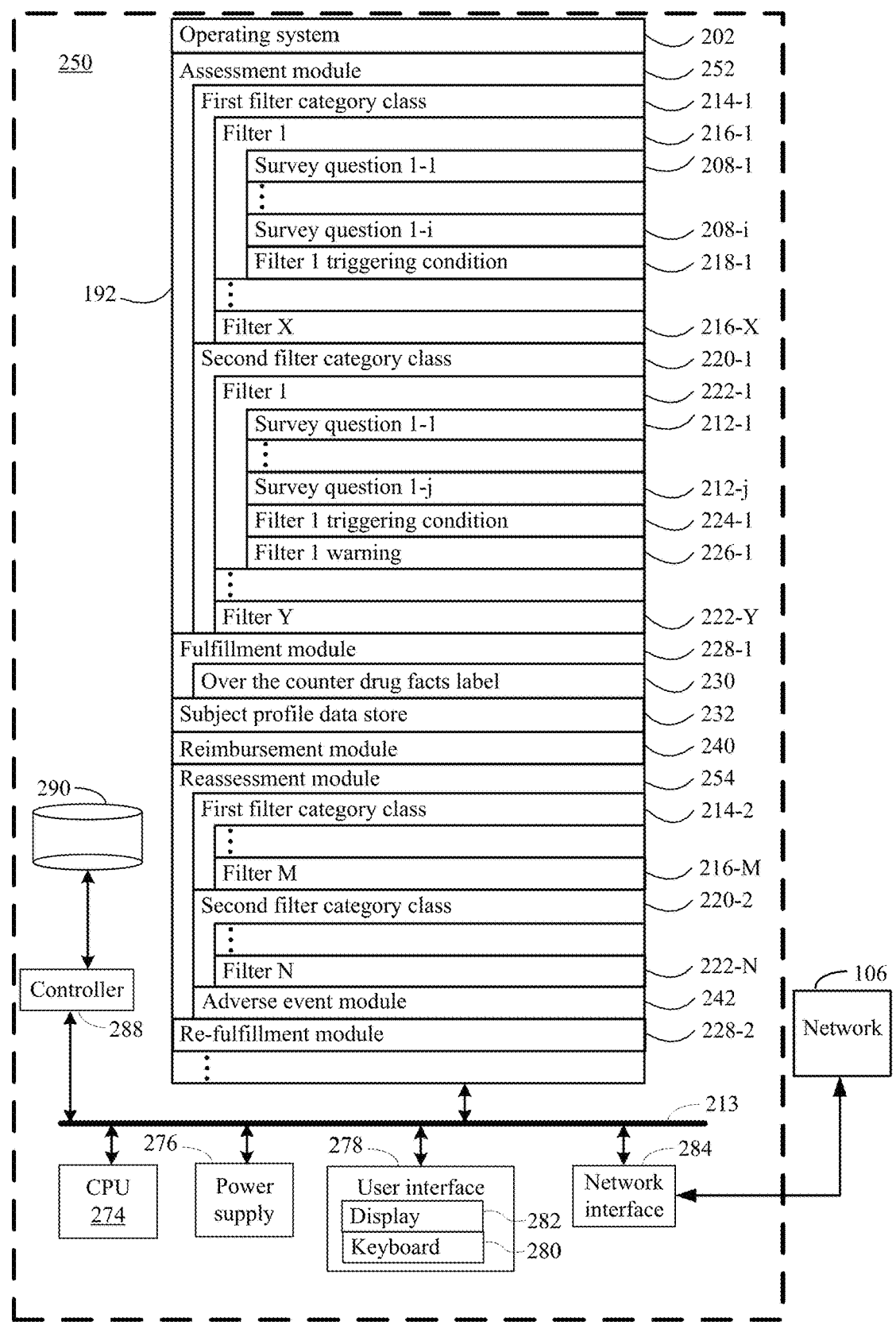
FIG. 2 illustrates an example device for qualifying a human subject for delivery of a corticosteroid pharmaceutical composition over-the-counter to treat or prevent symptoms of asthma in accordance with various embodiments of the present disclosure.

Turning to FIG. 2 with the foregoing in mind, an exemplary corticosteroid pharmaceutical composition OTC dispensing device 250 configured for determining whether a subject is qualified for OTC delivery of a corticosteroid is depicted. Referring to FIG. 2, in typical embodiments, the corticosteroid pharmaceutical composition OTC dispensing device 250 includes one or more computers. For purposes of illustration in FIG. 2, the corticosteroid pharmaceutical composition OTC dispensing device 250 is represented as a single computer that includes all of the functionality for qualifying a human subject for over-the-counter delivery of a corticosteroid pharmaceutical composition to treat or prevent symptoms of asthma. However, the present disclosure is not limited thereto. In some embodiments, the functionality for qualifying a human subject for over-the-counter delivery of a corticosteroid pharmaceutical composition to treat or prevent symptoms of asthma is spread across any number of networked computers and/or resides on each of several networked computers, is hosted on one or more virtual machines at a remote location accessible across the communications network 106, and/or is hosted on one or more containers at a remote location accessible across the communications network 106. One of skill in the art will appreciate that any of a wide array of different computer topologies are used for the application and all such topologies are within the scope of the present disclosure.

The corticosteroid pharmaceutical composition OTC dispensing device 250 of FIG. 2 is configured to conduct a first survey (e.g., using assessment module 252 to perform an initial qualification of the subject for provision of a corticosteroid pharmaceutical composition) and/or a second survey (e.g., using reassessment module 254 to perform a re-qualification of the subject for provision of a corticosteroid pharmaceutical composition). The first survey (e.g., the assessment) includes a variety of questions 208, 212 associated with respective filters 216, 222 within a plurality of filters of the first filter category class 214-1 and a plurality of filters in the second filter category class 220-1, respectively. Answers to the questions in the first survey received by the device are run against filters of a first category class 214-1 and filters of a second category class 220-1 within the first and second pluralities of filters 216, 222, respectively. Similarly, the second survey (e.g., the reassessment) also includes a variety of questions associated with filters 216, 222 within a plurality of filters of a first category class 214-2 and a plurality of filters of a second category class 220-2, respectively. Answers to the questions in the second survey received by the device are run against filters of a first category class 214-2 and filters of a second category class 220-2, e.g., within the first and second pluralities of filters, respectively. Filters 216 of the first filter category class 214 are configured to terminate the qualification process when fired. Filters 222 of the second filter category class 220 are configured to provide the subject with a warning associated with a corresponding survey question. In other words, the device of FIG. 2 is configured to accumulate results from a survey (e.g., survey questions 208 and survey questions 212) and run the results against corresponding filters (e.g., filters 216 and filters 222, respectively) in order to determine if a subject is qualified for OTC delivery of a corticosteroid pharmaceutical composition.

In the present disclosure, a plurality of filters refers to a series, or set, or filters in either the first filter category class or the second category class. For instance, in some embodiments, a plurality of filters of the first filter category class 214 can include any subset of filters 216 of the first filter category class. As an example, in some embodiments a plurality of filters of the first category class includes filters 216-1, 216-2, 216-3, . . . , 216-$i$, or any combination thereof. Similarly, a plurality of filters of the second filter category class 220 can include any set of filters 222 of the second filter category class. Moreover, in some embodiments a plurality of filters of the second category class includes filters 222-1, 222-2, 222-3, . . . , 222-$i$, or any combination thereof.

Continuing to refer to FIG. 2, in some embodiments, the dispensing device 250 includes one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278 that includes a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the corticosteroid pharmaceutical composition OTC dispensing device 250 but that can be electronically accessed by the corticosteroid pharmaceutical composition OTC dispensing device 250 over an Internet, intranet, or other form of network or electronic cable (illustrated as element 106 in FIG. 2) using network interface 284.

In some embodiments, the memory 192 of the corticosteroid pharmaceutical composition OTC dispensing device 250 stores one or more of:
- an operating system 202 that includes procedures for handling various basic system services;
- an assessment module 252 for qualifying a subject for an initial over-the-counter delivery of a corticosteroid pharmaceutical composition to treat or prevent symptoms of asthma, by communicating survey questions, obtaining results therefrom, and applying the results to qualifying filters, the assessment module including:
  - a first filter category class 214-1, including filters 216 (e.g., a first plurality of filters), each respective filter 216 in the first filter category class 214-1 associated with one or more survey questions 208 and one or more triggering conditions 218; and
  - a second filter category class 220-1, including filters 222 (e.g., a second plurality of filters), each respective filter 222 in the second filter category class 220-1 associated with one or more survey questions 208, triggering conditions 224, and warnings 226;
  - a fulfillment module 228-1 for executing a fulfillment process when no filter 216 in the first filter category class 214-1 has been fired for a subject and the subject has acknowledged each warning 226 associated with each filter 222 in the second filter category class 220-1 that was fired as a result of answers by the subject to the survey questions 208, where the fulfillment process includes communicating an over-the-counter drug facts label 230 for the corticosteroid pharmaceutical composition to the subject and receiving confirmation from the subject that the over-the-counter drug facts label has been received and read;
- a reassessment module 254 for qualifying a subject for a subsequent over-the-counter delivery of a corticosteroid pharmaceutical composition to treat or prevent symptoms of asthma, by communicating survey questions, obtaining results therefrom, and applying the results to qualifying filters, the assessment module including:
  - a first filter category class 214-2, including filters 216 (e.g., a third plurality of filters), each respective filter 216 in the first filter category class 214-2 associated with one or more survey questions 208 and one or more triggering conditions 218; and
  - a second filter category class 220-2, including filters 222 (e.g., a second plurality of filters), each respective filter 222 in the second filter category class 220-2 associated with one or more survey questions 208, triggering conditions 224, and warnings 226;
- a re-fulfillment module 228-2 for executing a re-fulfillment process when no filter 216 in the first filter category class 214-2 has been fired for a subject and the subject has acknowledged each warning 226 associated with each filter 222 in the second filter category class 220 that was fired as a result of answers by the subject to the survey questions 212, where the fulfillment process includes communicating an over-the-counter drug facts label 230 for the corticosteroid pharmaceutical composition to the subject and receiving confirmation from the subject that the over-the-counter drug facts label has been received and read;
- a subject profile data store 232 including a user profile 234 for each of a plurality of subjects, each respective user profile 234 including information (e.g., shipping information, billing information, biometric information, etc.) about a corresponding subject in the plurality of subjects, an initial order date and destination 236, and any re-order date and the destination 238 for the corticosteroid pharmaceutical composition made by the corresponding subject using the corticosteroid pharmaceutical composition OTC dispensing device 250;
- an adverse event module 242 for identifying and aggregating records of adverse events associated with a plurality of subjects, e.g., corresponding to the firing of a filter 216 in the first filter category class 214-2 during a re-fulfillment process; and
- a reimbursement module 240 for determining eligibility and/or communicating an insurance claim associated with delivery of the corticosteroid, e.g., based on insurance information stored in a respective user profile 234.

In some embodiments, the assessment module 252, reassessment module 254, and/or fulfillment module 228 are accessible within any browser (e.g., phone, tablet, laptop/desktop, or smartwatch). In some embodiments, the assessment module 252, reassessment module 254, and/or fulfillment module 228 run on native device frameworks, and is available for download onto a user device 102 running an operating system 202 such as Android, iOS, or WINDOWS. In some embodiments, the assessment module 252, reassessment module 254, and fulfillment module 228 are module in a single software application.

In some implementations, one or more of the above identified data elements or modules (e.g., assessment module 252, fulfillment module 228-1, etc.) of the corticosteroid pharmaceutical composition OTC dispensing device 250 for qualifying a human subject for over-the-counter delivery of a corticosteroid pharmaceutical composition to treat or prevent symptoms of asthma are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a corticosteroid pharmaceutical composition OTC dispensing device 250 for qualifying a human subject for over-the-counter delivery of a corticosteroid pharmaceutical composition to treat or prevent symptoms of asthma is a smart phone (e.g., an iPhone, Blackberry, etc.), a laptop, a tablet computer, a desktop computer, a smart watch, or other form or wired or wireless networked device. In some embodiments, the corticosteroid pharmaceutical composition OTC dispensing device 250 is not mobile. In some embodiments, the corticosteroid pharmaceutical composition OTC dispensing device 250 is mobile. In the interest of brevity and clarity, only a few of the possible components of the corticosteroid pharmaceutical composition OTC dispensing device 250 are shown in FIG. 2 in order to better emphasize the additional software modules that are installed on the corticosteroid pharmaceutical composition OTC dispensing device 250.

Figure 3A:
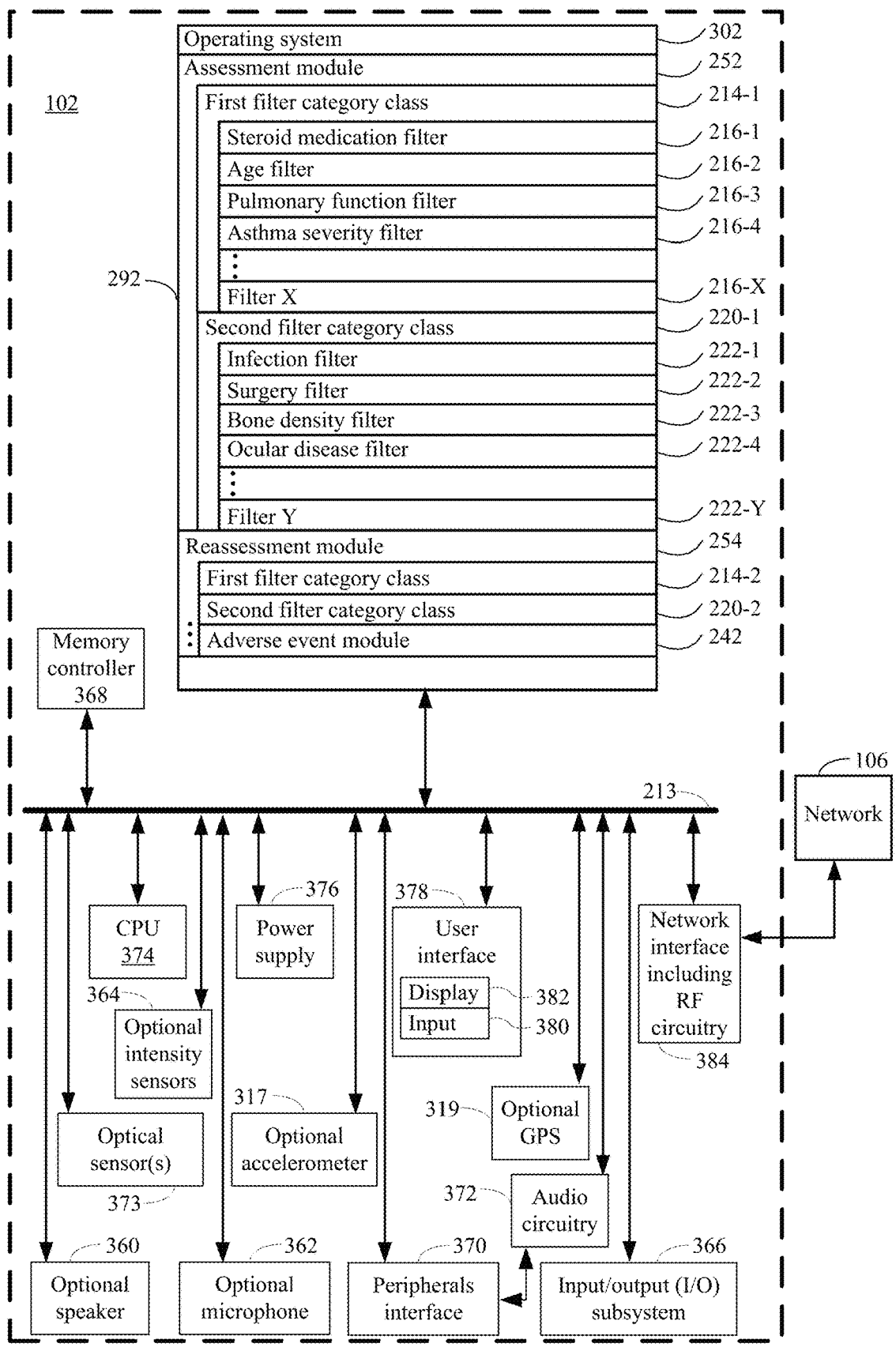
FIGS. 3A and 3B collectively illustrate an example device associated with a human subject for qualifying the human subject for over-the-counter delivery of a corticosteroid pharmaceutical composition to treat or prevent symptoms of asthma, in accordance with an embodiment of the present disclosure, where it will be appreciated that the example device of FIGS. 3A and 3B works in conjunction with the device of FIG. 2 to perform the methods illustrated in FIGS. 4 through 8 in some embodiments by, for instance providing the device of FIG. 2 with survey results and/or the results of firing filters of the present disclosure against such survey results but that, in alternative embodiments, the device of FIG. 2 performs all the methods of the present disclosure and the device of FIGS. 3A and 3B is not used. In still further alternative embodiments, the device of FIGS. 3A and 3B performs the methods of the present disclosure and the device of FIG. 2 is not used.
Figure 3B:
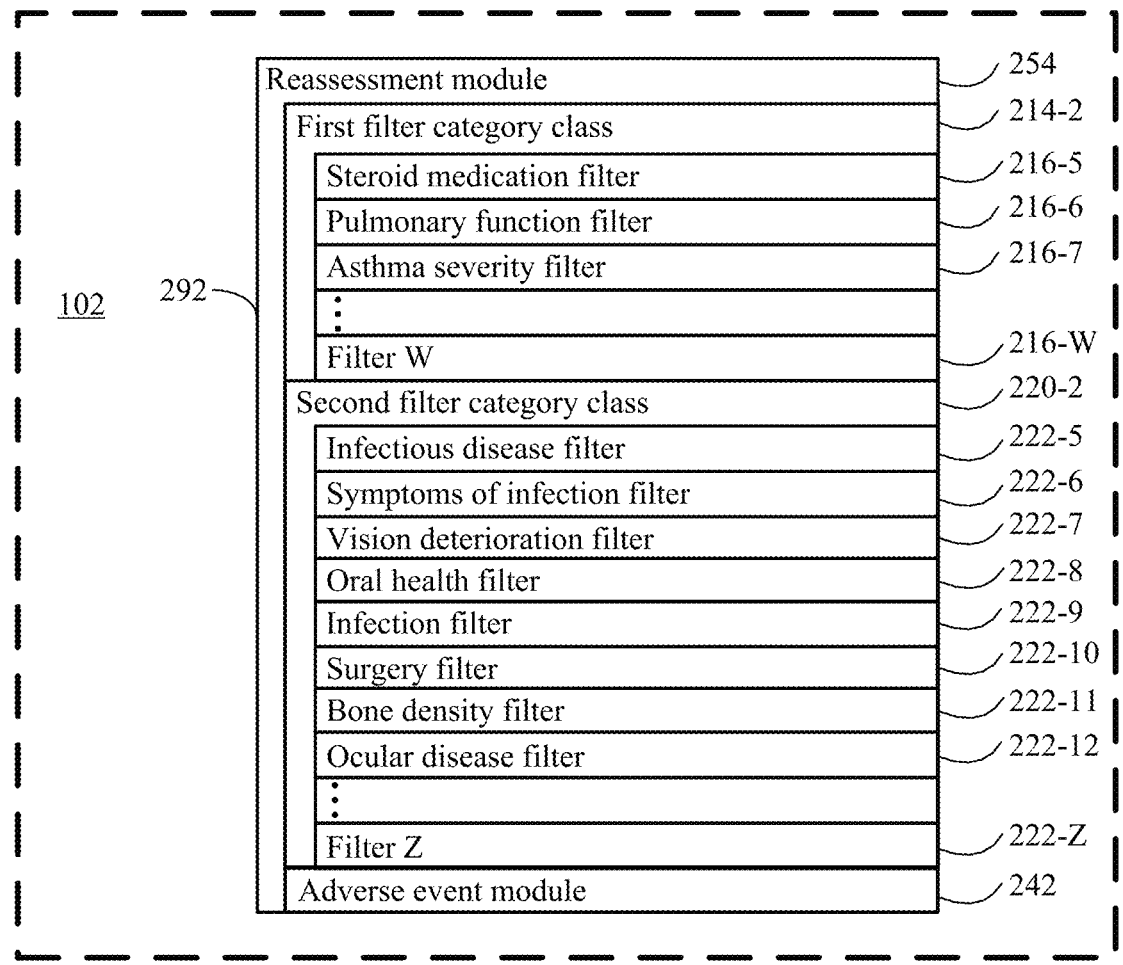

FIGS. 3A and 3B provide a description of a user device 102 that can be used with the present disclosure. The user device 102 illustrated in FIGS. 3A and 3B has one or more processing units (CPU's) 374, peripherals interface 370, memory controller 368, a network or other communications interface 384, a memory 392 (e.g., random access memory), a user interface 378 that includes a display 382 and input 380 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 382 of the user device 102), an optional input/output (I/O) subsystem 366, one or more optional optical sensors 373, one or more communication busses 313 for interconnecting the aforementioned components, and a power supply 376 for powering the aforementioned components.

In some embodiments, the input 380 is a touch-sensitive display, such as a touch-sensitive surface. In some embodiments, the user interface 378 includes one or more soft keyboard embodiments. The soft keyboard embodiments may include standard (e.g., QWERTY) and/or non-standard configurations of symbols on the displayed icons.

The user device 102 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the user device 102 and/or for determining an amount of physical exertion by the subject.

It should be appreciated that the user device 102 illustrated in FIG. 3 is only one example of a multifunction device that may be used for performing a survey (e.g., first survey 206) in order to qualify for over-the-counter delivery of a corticosteroid pharmaceutical composition to treat or prevent symptoms of asthma, and that the user device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 392 of the user device 102 illustrated in FIG. 3 optionally includes high-speed random access memory and optionally also includes non-volatile memory, such as one or more magnetic disk storage devices, flash memory devices, or other non-volatile solid-state memory devices. Access to memory 392 by other components of the corticosteroid pharmaceutical composition OTC dispensing device 250, such as CPU(s) 374 is, optionally, controlled by the memory controller 368. In some embodiments, the memory 392 of the user device 102 illustrated in FIG. 3 optionally includes:
- an operating system 302 that includes procedures for handling various basic system services;
- the assessment module 252 described above in conjunction with the corticosteroid OTC dispensing device 250;
- a first filter category class 214-1 described above in conjunction with the corticosteroid pharmaceutical composition OTC dispensing device 250 that includes a first steroid medication filter 216-1, an age filter 216-2, a first pulmonary function filter 216-3, and a first asthma severity filter 216-4;
- a second filter category class 220-1 described above in conjunction with the corticosteroid pharmaceutical composition OTC dispensing device 250 that includes a first infection filter 222-1, a first surgery filter 222-2, a first bone density filter 222-3, and a first ocular disease filter 222-4;
- the reassessment module 254 described above in conjunction with the corticosteroid OTC dispensing device 250;
- a first filter category class 214-2 that includes a second steroid medication filter 216-5, a second pulmonary function filter 216-6, and a second asthma severity filter 216-7; and
- the second filter category class 220-2 described above in conjunction with the corticosteroid pharmaceutical composition OTC dispensing device 250 including an infectious disease filter 222-5, a symptoms of infectious disease filter 222-6, a vision deterioration filter 227-7, on oral health filter 222-8, a second infection filter 222-9, a second surgery filter 222-10, a second bone density filter 222-11, and a second ocular disease filter 222-12.

In some embodiments, the optional accelerometer 317, optional GPS 319, and/or magnetometer (not shown) of the user device 102 or such components are used to recommend to qualifying subjects one or more suitable destinations for delivery of the corticosteroid pharmaceutical composition over-the-counter. In some embodiments, the GPS 319 is used to determine if a subject is geographically restricted for OTC delivery of the corticosteroid pharmaceutical composition. Geographical restrictions include a subject residing outside of delivery or shipping regions, marketing restrictions, and/or government regulations.

The peripherals interface 370 can be used to couple input and output peripherals of the device to CPU(s) 374 and memory 392. The one or more processors 374 run or execute various software programs and/or sets of instructions stored in memory 392, such as the survey module 204, to perform various functions for the user device 102 and to process data.

In some embodiments, the peripherals interface 370, CPU(s) 374, and memory controller 368 are, optionally, implemented on a single chip. In some other embodiments, they are implemented on separate chips.

RF (radio frequency) circuitry of network interface 384 receives and sends RF signals, also called electromagnetic signals. In some embodiments, the survey module 204, survey questions 208/212, answers to survey questions 208/212, and/or the over-the-counter drug facts label 230 are communicated to the subject device 102 using this RF circuitry. In some embodiments, the RF circuitry 384 converts electrical signals to/from electromagnetic signals and communicates with communications networks and other communications devices and/or the data collection device 200 and/or the corticosteroid pharmaceutical composition OTC dispensing device 250 via the electromagnetic signals. The RF circuitry 384 optionally includes well-known circuitry for performing these functions, including an antenna system, an RF transceiver, one or more amplifiers, a tuner, one or more oscillators, a digital signal processor, a CODEC chipset, a subscriber identity module (SIM) card, memory, and so forth. RF circuitry 384 optionally communicates with the communication network 106. In some embodiments, the circuitry 384 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. In some embodiments, the speaker 260 converts the electrical signals to human-inaudible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 392 and/or the RF circuitry 384 by the peripherals interface 370.

In some embodiments, the power supply 376 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 382 on the front of the user device 102, so that the input 380 is enabled for use as a viewfinder for still and/or video image acquisition. In some embodiments, another optical sensor 373 is located on the front of the user device 102 so that the subject's image is obtained (e.g., to verify the health, condition, or identity of the subject as part of qualifying the subject for over-the-counter delivery of a corticosteroid pharmaceutical composition to treat or prevent symptoms of asthma), to help diagnose a subject's condition remotely, or to acquire visual physiological measurements of the subject, etc.)

As illustrated in FIG. 3, the user device 102 preferably includes an operating system 302 that includes procedures for handling various basic system services. The operating system 302 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the user device 102 is a smart phone or a smart watch. In other embodiments, the user device 102 is not a smart phone or a smart watch but rather is a tablet computer, a desktop computer, an emergency vehicle computer, or other form or wired or wireless networked device. In the interest of brevity and clarity, only a few of the possible components of the user device 102 are shown in FIG. 3 in order to better emphasize the additional software modules that are installed on the user device 102.

While the system 48 disclosed in FIG. 1 can work standalone, in some embodiments it can also be linked with electronic medical record systems to exchange information in any way.

Now that details of a system 48 for qualifying a human subject for over-the-counter delivery of a corticosteroid pharmaceutical composition to treat or prevent symptoms of asthma have been disclosed, details regarding a method (400), including processes and features to be performed by the system, in accordance with an embodiment of the present disclosure, are disclosed with reference to FIGS. 4A through 4I. In some embodiments, such processes and features of the system are carried out by the assessment module 252, reassessment module 254, fulfillment module 228-1, and/or re-fulfillment module 228-2 illustrated in FIGS. 2 and 3. In some embodiments, the assessment module 252, reassessment module 254, fulfillment module 228-1, and/or reassessment module 228-2 are a single software module. In the flow chart, elements in dashed boxes are considered to be optional.

In some embodiments, symptoms of asthma include difficulty breathing, chest pain, a cough (e.g., a chronic cough, a dry cough, a cough including phlegm, a mild cough, and a severe cough), wheezing, difficulty breathing, breathing through the mouth, fast breathing, rapid breathing, frequent respiratory infections, shortness of breath at night, tightness of the chest, a flaring of symptoms, anxiety, early awakening, fast or elevated heart rate, and/or throat irritation. In some embodiments, symptoms of asthma include fast breathing with chest retractions, cyanosis, rapid movement of nostrils, deep and/or rapid rib and/or stomach movement, and an expanded chest that does not deflate when exhaling.

Blocks 402-410. Referring to block 402 of FIG. 4A, a goal of the present disclosure is to qualify subjects for over-the-counter delivery of a corticosteroid pharmaceutical composition to treat or prevent symptoms of asthma using a computer system such as a corticosteroid pharmaceutical composition OTC dispensing device 250. The corticosteroid pharmaceutical composition OTC dispensing device (e.g., device 250) includes one or more processors (e.g., processor 274) and a memory (e.g., memory 192 and/or 290). The memory stores non-transitory instructions that, when executed by the one or more processors, perform a method.

Referring to blocks 404-410, in some embodiments the corticosteroid pharmaceutical composition includes a class B corticosteroid. In some embodiments, the corticosteroid includes a glucocorticosteroid. In some embodiments, the corticosteroid includes budesonide.

In some embodiments the corticosteroid pharmaceutical composition includes fluticasone furoate (e.g., ($6\alpha,11\beta,16\alpha,17\alpha$)-6,9-difluoro-17-{[(fluoro-methyl)thio]carbonyl}-11-hydroxy-16-methyl-3-oxoandrosta-1,4-dien-17-yl 2-furancarboxylate). In some embodiments the corticosteroid pharmaceutical composition includes mometasone furoate (e.g., (9R,10S,11S,13S,14S,16R,17R)-9-chloro-17-(2-chloroacetyl)-11-hydroxy-10,13,16-trimethyl-3-oxo-6,7,8,9,10,11,12,13,14,15,16,17-dodecahydro-3H-cyclopenta[a]phenanthren-17-yl furan-2-carboxylate). In some embodiments the corticosteroid pharmaceutical composition includes fluticasone propionate (e.g., S-(fluoromethyl)-$6\alpha$, 9-difluoro-$11\beta$, 17-dihydroxy-$16\alpha$-methyl-3-oxoandrosta-1, 4-diene-$17\beta$-carbothioate, 17-propanoate). In some embodiments the corticosteroid pharmaceutical composition includes beclomethasone dipropionate (e.g., (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phenanthren-17-yl propionate). In some embodiments, the corticosteroid pharmaceutical composition includes ciclesonide (e.g., 2-[(1S, 2S, 4R, 8S, 9S,11S, 12S, 13R)-6-cyclohexyl-11-hydroxy-9, 13-dimethyl-16-oxo-5, 7-dioxapentacyclo $[10.8.0.0^{2,9}.0^{4,8}.0^{13,18}]$ icosa-14, 17-dien-8-yl]-2-oxoethyl 2-methylpropanoate). These, and other, corticosteroids are described, for example, in Swartz, et al., "Corticosteroids: clinical pharmacology and therapeutic use," Drugs 16(3), (1978), the content of which is hereby incorporated by reference.

In some embodiments, the corticosteroid pharmaceutical composition includes any compound disclosed in U.S. Pat. No. 6,598,603, entitled "Method for treating respiratory diseases," which is hereby incorporated by reference. In some embodiments, the corticosteroid pharmaceutical composition includes any compound disclosed in U.S. Pat. No. 7,759,328, entitled "Composition for inhalation," which is hereby incorporated by reference. In some embodiments, the corticosteroid pharmaceutical composition includes any compound disclosed in U.S. Pat. No. 7,897,646, entitled "Use for budesonide and formoterol," which is hereby incorporated by reference.

In some embodiments, the corticosteroid pharmaceutical composition includes any compound disclosed in U.S. Pat. No. 5,695,743, entitled "Medical aerosol formulations," which is hereby incorporated by reference. In some embodiments, the corticosteroid pharmaceutical composition includes any compound disclosed in U.S. Pat. No. 5,482,934, entitled "Pregna-1,4-diene3,20-dione-16-17-acetal-21 esters, process for their preparation, composition, and methods for the treatment of inflammatory conditions," which is hereby incorporated by reference.

In some embodiments, the corticosteroid pharmaceutical composition includes any compound disclosed in U.S. Pat. No. 6,858,596, entitled "Formulation containing anti-inflammatory androstane derivative," which is hereby incorporated by reference. In some embodiments, the corticosteroid pharmaceutical composition includes any compound disclosed in U.S. Pat. No. 7,101,866, entitled "Anti-inflammatory androstane derivative," which is hereby incorporated by reference.

In some embodiments, the corticosteroid pharmaceutical composition includes any compound disclosed in U.S. Pat. No. 6,127,353, entitled "Mometasone furoate monohydrate, process for making same and pharmaceutical compositions," which is hereby incorporated by reference. In some embodiments, the corticosteroid pharmaceutical composition includes any compound disclosed in U.S. Pat. No. 5,837,699, entitled "Use of mometasone furoate for treating upper airway passage diseases," which is hereby incorporated by reference.

In some embodiments, the corticosteroid pharmaceutical composition includes any compound disclosed in U.S. Pat. No. 7,972,626, entitled "Fluticasone propionate nasal pharmaceutical formulations and methods of using same," which is hereby incorporated by reference.

In some embodiments, the corticosteroid pharmaceutical composition includes any compound disclosed in U.S. Pat. No. 5,993,781, entitled "Fluticasone propionate nebulizable formulations," which is hereby incorporated by reference.

In some embodiments, the corticosteroid pharmaceutical composition includes any compound disclosed in U.S. Pat. No. 4,866,051, entitled "Micronised beclomethasone dipropionate monohydrate compositions and methods of use," which is hereby incorporated by reference.

In some embodiments, in response to receiving a first request from a user to be qualified for provision of a corticosteroid pharmaceutical composition, the system creates a corresponding subject profile, e.g., containing biographic information about the subject, e.g., one or more of a subject name, date of birth, residence, delivery address, social security number, medical record number, insurance information, user name, identification password, etc. In some embodiments, the system registers a subject that has not previously received an over-the-counter provision of a corticosteroid pharmaceutical composition as a new user of the corticosteroid pharmaceutical composition, and the device will perform an initial assessment method for qualifying the subject for a provision of the corticosteroid pharmaceutical composition, e.g., regardless of whether the subject previously received a provision of a corticosteroid pharmaceutical composition via prescription.

In some embodiments, the system registers a subject that has previously received a provision of a corticosteroid pharmaceutical composition via prescription as a previous user of the corticosteroid pharmaceutical composition, and the device will perform a reassessment method for re-qualifying the subject for a provision of the corticosteroid pharmaceutical composition.

In some embodiments, where the subject previously received a provision of a different corticosteroid pharmaceutical composition via prescription, the system will perform a modified method for qualifying the subject for provision of the corticosteroid pharmaceutical composition that accounts for differences in the contraindications and risk factors of the two corticosteroid pharmaceutical compositions. For example, in response to receiving a request to qualify a user that previously received a provision of a pharmaceutical composition containing ciclesonide via prescription, for an over-the-counter provision of budesonide, the system performs a modified method for re-qualifying (e.g., a reassessment) the subject for the corticosteroid pharmaceutical composition that includes a survey question and corresponding filter relating to whether the subject has a dairy allergy (e.g., regardless of whether a reassessment for a pharmaceutical composition containing budesonide would normally consider a subject's dairy allergy), because that factor would not have been considered when the subject received the prescription for the composition containing ciclesonide.

In some embodiments, in response to receiving a second or subsequent request from a user to be qualified for provision of a corticosteroid pharmaceutical composition, the system registers the subject as a returning customer, e.g., when the subject has previously received an over-the-counter provision of the corticosteroid and a corresponding subject profile 232 already exists for the subject.

Figure 7A:
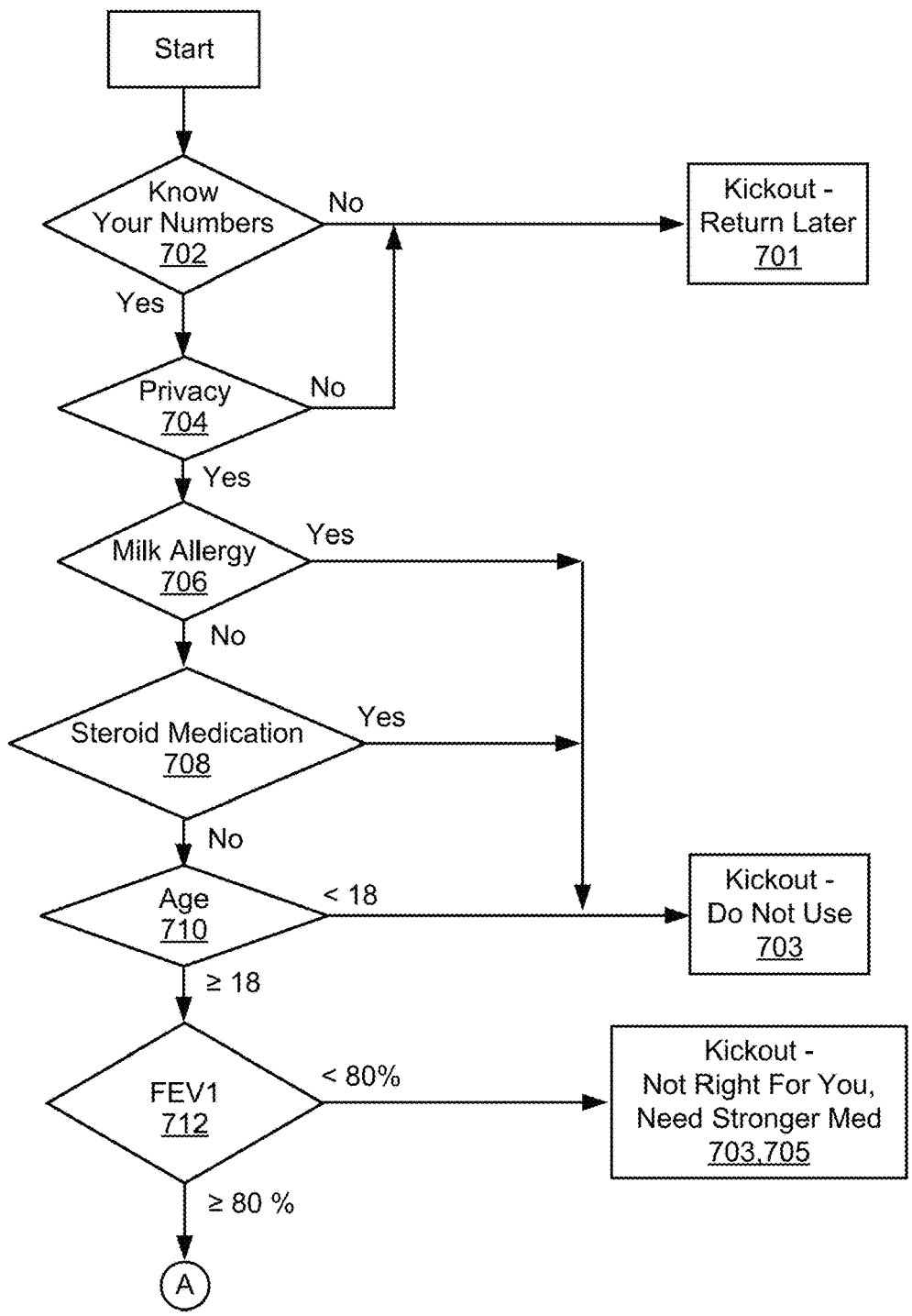
FIGS. 7A, 7B, 7C, and 7D collectively illustrate an example method for qualifying a subject for an over-the-counter provision of a corticosteroid pharmaceutical composition in accordance with an embodiment of the present disclosure.

In some embodiments, prior to proceeding with the qualification or re-qualification method, the device prompts (702, 704) the user is asked to confirm that they have adequate privacy to provide sensitive medical information (e.g., prompt 704 in FIG. 7A) and/or that they are in possession of medical information required to complete the qualification process (e.g., prompt 702 to confirm that they have knowledge of the required medical information required to complete the survey.

Blocks 412-414. Referring to block 412 of FIG. 4A, the method includes conducting a first survey of the subject thereby obtaining a first plurality of survey (e.g., results to survey questions 208, 212 (e.g., one or more of the survey questions set forth in Table 1). In some embodiments, the device transmits one or more survey questions to the user, prompting a response, and then receives a response to the one or more survey questions back from the subject. In some embodiments, the first survey results include, or at least indicate, some or all of the subject characteristics listed in Table 1. For example, in some embodiments, the first plurality of survey results includes, or at least indicates, 2, 3, 4, 5, 6, 7, 8, 9, 10, 11, or all 12 of the characteristics listed in Table 1. In one embodiment, the first survey questions 208, 212 and results include, or at least indicate, characteristics 2-4, 6-9, and 11 as provided in Table 1.

Referring to block 414, in some embodiments the first survey results indicate whether the subject is already taking a steroid medication (e.g., responsive to a survey question 208 that is associated with and/or applied to (708, 720) a steroid medication filter 216-1 of a first category class), an age of the subject (e.g., responsive to a survey question 208 that is associated with and/or applied to (710) an age filter 216-2 of a first category class), a pulmonary function status of the subject (e.g., responsive to a survey question 208 that is associated with and/or applied to (712, 714, 716, 718) a pulmonary function filter 216-3 of a first category class), whether the subject has an untreated infection (e.g., responsive to a survey question 208 that is associated with and/or applied to (724) an infection filter 222-1 of a second category class), a surgery status of the subject (e.g., responsive to a survey question 208 that is associated with and/or applied to (726) a surgery filter 222-2 of a second filter class category), a bone density status of the subject (e.g., responsive to a survey question 208 that is associated with and/or applied to (728) a bone density filter 222-3 of a second category class), and whether the subject has ever had cataracts or glaucoma (e.g., responsive to a survey question 208 that is associated with and/or applied to (730) an ocular disease filter 222-4 of a second category class).

In some embodiments, the first survey includes questions that elicit responses providing or indicating some or all of the characteristics listed in Table 1. In some embodiments, the survey includes questions corresponding to each of the survey results required for the methods described herein. In other embodiments, the survey includes questions corresponding to only a subset of the survey results required for the methods described herein. In some embodiments, other survey results required for the methods described herein are acquired through other means (e.g., upon registration/subscription for a service associated with qualifying the subject for over-the-counter medication, from a healthcare provider, from a prior survey, from a database associated with a pharmacy, from an electronic health record associated with the subject, from the subject profile data store 232, etc.). For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a last pulmonary function measurement determined for the subject).

TABLE 1

Example subject characteristics for qualifying a subject for an over-the-counter provision of a corticosteroid pharmaceutical composition.

| Result | Example Characteristics |
|---|---|
| 1 | whether the subject has a dairy allergy, |
| 2 | whether the subject is already taking a steroid medication, |
| 3 | an age of the subject, |
| 4 | a pulmonary function status of the subject, |
| 5 | whether the subject has a liver problem, |
| 6 | whether the subject has an untreated infection, |
| 7 | a surgery status of the subject, |
| 8 | a bone density status of the subject, |
| 9 | whether the subject has ever had cataracts or glaucoma, and |
| 10 | whether the subject is taking a medication that interacts with the corticosteroid pharmaceutical composition |
| 11 | an frequency of asthma symptoms |
| 12 | whether the subject is allergic to the corticosteroid pharmaceutical composition |

It is contemplated that, in some embodiments, any one or more of the survey questions 208, 212 provided in Table 1 will not be included in the first survey (e.g., will not be used for the assessment. For example, in some embodiments, a characteristic associated with a particular survey questions will be informative when qualifying a subject for one corticosteroid but not for another corticosteroid.

Accordingly, it is contemplated that the first survey questions 208 include any subset of survey results provided in Table 1. For brevity, all possible combinations of the survey questions 208, 212 eliciting the characteristics provided in Table 1 are not specifically delineated here. However, the skilled artisan will easily be able to envision any particular subset of the survey questions 208, 212 that elicit the characteristics provided in Table 1. Likewise, the skilled artisan may know of other survey questions, eliciting informative subject characteristics not provided in Table 1, that may be combined with any subset of survey questions that elicit subject characteristics provided in Table 1 to form the first survey questions used in the methods described herein.

In some embodiments, the first and/or second survey is conducted by transmitting a plurality of questions to the subject, e.g., some or all of the survey questions, and receiving answers to the plurality of survey questions before applying any of the answers to respective filters. For example, with reference to the workflow in FIG. 7, the device transmits questions relating to all of the filters of the first category class, all of the filters of the second category class, or all of the filters in the workflow (e.g., as a virtual survey where all of the questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the corticosteroid pharmaceutical composition. In alternative embodiments, the device transmits questions relating to just those filters of the first category class for which it could not obtain answers to the questions from an electronic database associated with the subject, such as electronic health record of the subject, and just those filters of the second category class it could not obtain answers to the questions from an electronic database associated with the subject (e.g., as a virtual survey where such unanswered questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the corticosteroid pharmaceutical composition.

Figure 7B:
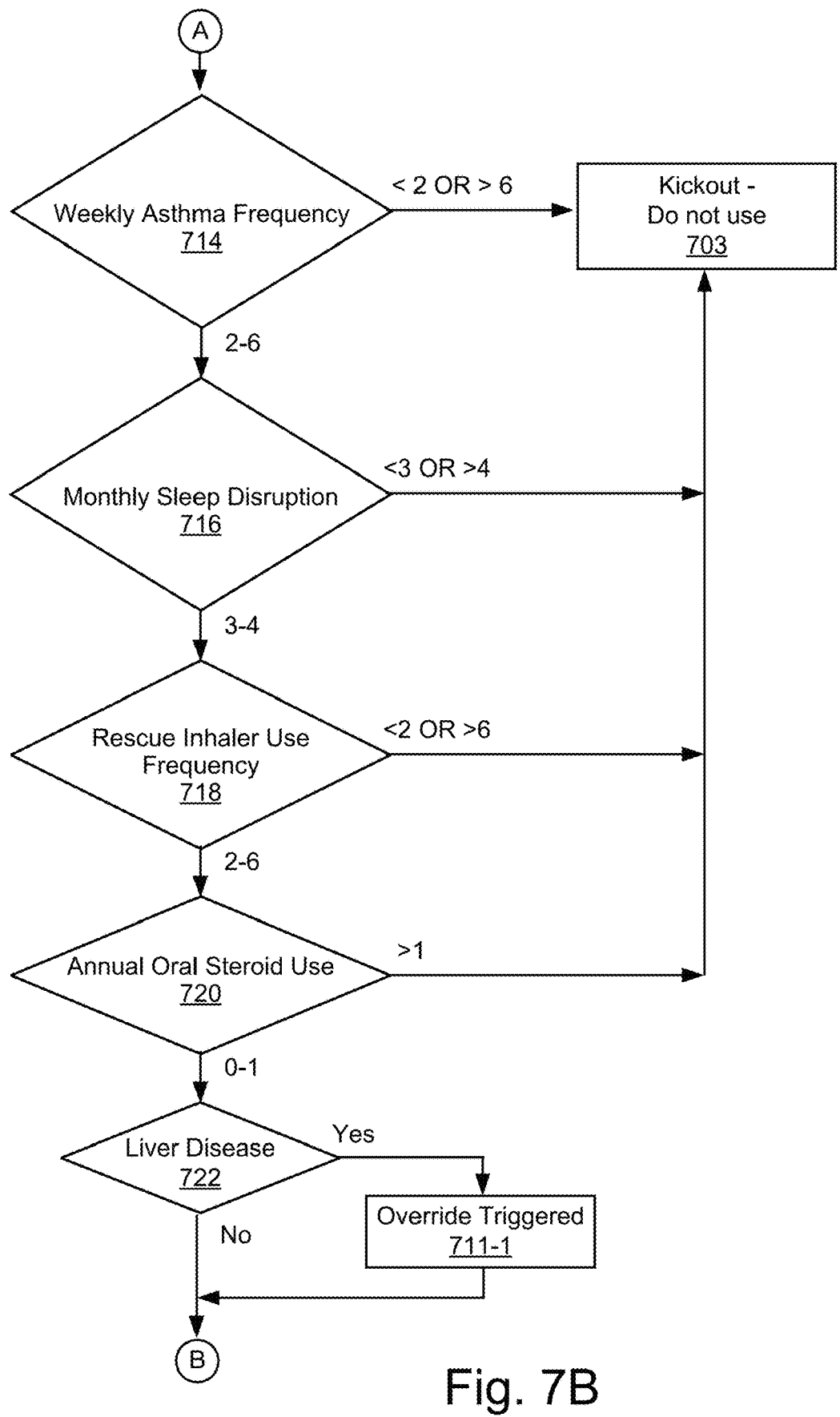
Figure 7C:
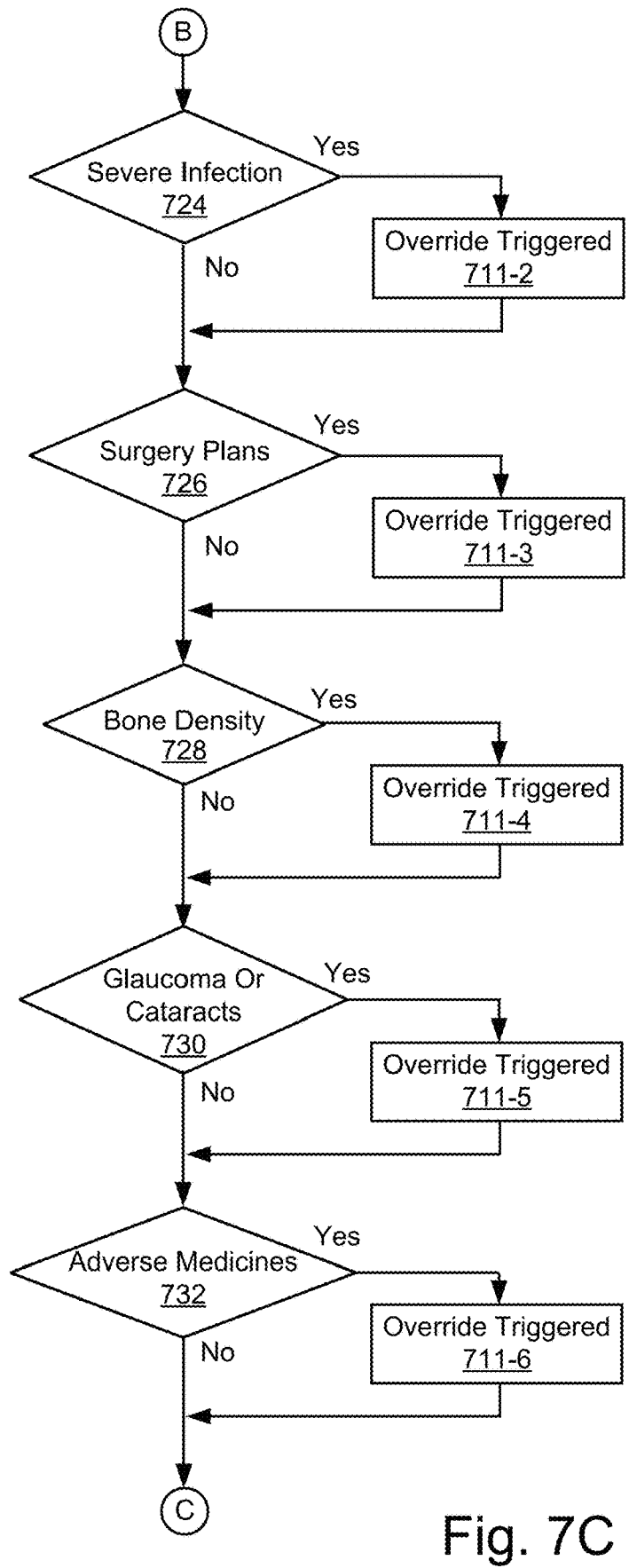

In some embodiments, the first and/or second survey is conducted in a serial fashion, e.g., by transmitting a first question or a first group of survey questions (e.g., associated with a single filter) to the subject, receiving an answer to the single survey question or small group of survey questions, and applying the answer or answers to a filter, prior to transmitting a second question or second group of questions to the subject. For example, with reference to the workflow in FIG. 7, in some embodiments the device transmits a first question to the subject, relating to the dairy allergy status of the subject. After receiving the answer to the survey question, the device applies the answer to a first allergy filter (706). If the first allergy filter is fired (e.g., in response to an answer that indicates the subject has a severe diary allergy), the device terminates (701) the process, and optionally provides the user with a message relating to why they are being denied a provision of the corticosteroid pharmaceutical composition (e.g., as illustrated in FIG. 5B, message 552, advising the subject that the corticosteroid pharmaceutical composition contains traces of milk proteins), a suggestion for following-up with a medical professional (e.g., as illustrated in FIGS. 7B and 7C, when the survey answers indicate that the subject has developed cataracts or glaucoma (730), the device initiates (711-5) an override procedure), and/or a suggestion to make a lifestyle change, to treat or prevent their symptoms of asthma. Start here Blocks 416-442. Referring to block 416 of FIG. 4B, all or a portion of the first survey results are run against a first plurality of filters of a first category class 214. As previously described, the first plurality of filters includes a subset of filters 216 of the first filter category class 214. When a respective filter in the first plurality of filters is fired (e.g., when a survey result indicates that a triggering condition 218 has been met), the subject is deemed not qualified for delivery of the corticosteroid pharmaceutical composition and the method is terminated without delivery of the corticosteroid pharmaceutical composition.

In some embodiments, e.g., when the method is terminated without delivery of the corticosteroid pharmaceutical composition, the subject is prevented from attempting to requalify for the corticosteroid for a predetermined period of time (e.g., the subject is locked out). In some embodiments, the subject is prevented from attempting to requalify for the corticosteroid after a predetermined number of qualification attempts. In some embodiments, the subject is prevented from attempting to requalify for the corticosteroid after a failing to verify a communication (e.g., failing to verify a text message sent to the subject). This prevents the subject from abusing the systems and methods of the present disclosure.

Referring to blocks 418-442, specific filters 216 in the first plurality of filters and their exemplary triggering conditions 218 that cause the corresponding filter to fire are detailed.

In some embodiments, the first plurality of filters of the first category class 214 includes some or all of the filters 216 listed in Table 2. For example, in some embodiments, the first plurality of filters results includes, or at least indicates, 2, 3, 4, 5, or all 6 of the filters listed in Table 2. In one embodiment, the first plurality of filters includes at least filters 2-4, as provided in Table 2.

TABLE 2

Example filters for contraindications associated with qualifying a subject for an over-the-counter provision of a corticosteroid pharmaceutical composition.

| Filter | Example Criteria |
| --- | --- |
| 1a | a dairy allergy filter |
| 2a | a steroid medication filter |
| 3a | an age filter |
| 4a | a pulmonary function filter |
| 5a | an asthma severity filter |
| 6a | an adverse reaction filter |

It is contemplated that, in some embodiments, any one or more of the filters 216 provided in Table 2 will not be included in the first plurality of filters. For example, in some embodiments, a characteristic associated with a particular survey result will be informative when qualifying a subject for one particular corticosteroid but not for another corticosteroid.

Accordingly, it is contemplated that the first plurality of filters includes any sub-set of filters 216 provided in Table 2. Likewise, the skilled artisan may know of other filters 216, not provided in Table 2, which may be combined with any subset of the filters 216 provided in Table 2 to form the first plurality of filters results used in the methods described herein. For brevity, all possible combinations of the filters 216 provided in Table 2 are not specifically delineated here.

Referring to block 418, in some embodiments the first plurality of filters includes a dairy allergy filter (e.g., filter 1a in Table 2). In some embodiments, the dairy allergy filter is configured to be fired when the first plurality of survey results indicates that the subject has a diary allergy (e.g., a severe milk protein allergy). If the dairy allergy filter is fired, the subject is not permitted to obtain the corticosteroid pharmaceutical composition over-the-counter (e.g., the method is terminated without authorizing provision of the corticosteroid pharmaceutical composition to the subject).

Referring to block 420, in some embodiments the first plurality of filters includes a steroid medication filter (e.g., steroid medication filter 216-1 in FIG. 3 and/or filter 2a in Table 2). In some embodiments, first steroid medication filter is configured to be fired when the first plurality of survey results indicates that the subject is already taking a steroid medication. In some embodiments, the steroid medication filter is configured to be fired when the first plurality of survey results indicates that the subject is taking a steroid medication for asthma, a steroid medication for allergies, and/or a steroid medication for a skin rash. If the steroid medication filter is fired, the subject is not permitted to obtain the corticosteroid pharmaceutical composition over-the-counter (e.g., the method is terminated without authorizing provision of the corticosteroid pharmaceutical composition to the subject).

Referring to block 422-424, in some embodiments the first plurality of filters includes an age filter (e.g., age filter 216-2 in FIG. 3 and/or filter 3a in Table 2). In some embodiments, the age filter is fired when the first plurality of survey results indicates that the subject is not of an appropriate age to take an over-the-counter corticosteroid, e.g., they have not yet reached an age of majority, e.g., they are less than eighteen years old. If the age filter is fired, the subject is not permitted to obtain the corticosteroid pharmaceutical composition pharmaceutical composition over-the-counter (e.g., the method is terminated without authorizing provision of the corticosteroid pharmaceutical composition to the subject).

Referring to blocks 426-428, in some embodiments the first plurality of filters includes a pulmonary function filter (e.g., pulmonary function filter 216-3 in FIG. 3 and/or filter 4a in Table 2). The pulmonary function filter is configured to be fired at least when the first plurality of survey results indicates that the subject has severely compromised pulmonary function, e.g., warranting a stronger, prescription medication and/or treatment under supervision of a medical professional. In some embodiments, the pulmonary function filter queries a measured lung function of the subject, e.g., from a forced expiratory volume measured over one second (FEV1) assay. In some embodiments, a lung function value of no more than 80%, e.g., of a predicted volume determined using a forced expiratory volume measurement, is sufficient to fire the pulmonary function filter. In some embodiments, a compromised pulmonary function, capable of firing a pulmonary function filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the pulmonary function filter is fired, the subject is not permitted to obtain the corticosteroid pharmaceutical composition over-the-counter (e.g., the method is terminated without authorizing provision of the corticosteroid pharmaceutical composition to the subject).

Referring to blocks 430-438 of FIG. 4C, in some embodiments the first plurality of survey results further indicates an asthma severity status of the subject, and the first plurality of filters includes an asthma severity filter. In some embodiments, the first asthma filter is configured to be fired when the first plurality of survey results indicates that the subject has sufficiently severe asthma, e.g., warranting a stronger, prescription medication and/or treatment under supervision of a medical professional, and/or sufficiently mild asthma, e.g., that does not warrant over-the-counter treatment with an inhaled corticosteroid. In some embodiments, the asthma severity filter is implemented as one or more sub-filters, e.g., that query the frequency with which the subject experiences episodes of asthma, or a set of criteria as described for the one or more sub-filters considered together (e.g., using a classification algorithm to classify an asthma severity of the subject). If the asthma severity filter is fired, the subject is not permitted to obtain the corticosteroid pharmaceutical composition over-the-counter (e.g., the method is terminated without authorizing provision of the corticosteroid pharmaceutical composition to the subject).

Referring to block 432, in some embodiments the asthma severity filter includes an asthma frequency sub-filter, which is configured to be fired when the first plurality of survey results indicates that the subject experiences symptoms of asthma infrequently, e.g., less than two or three days per week, and/or very frequently, e.g., more than five or six times a week. In some embodiments, a frequency of asthmatic symptoms, capable of firing the asthma frequency sub-filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the asthma frequency sub-filter is fired, the subject is not permitted to obtain the corticosteroid pharmaceutical composition over-the-counter (e.g., the method is terminated without authorizing provision of the corticosteroid pharmaceutical composition to the subject).

Referring to block 434, in some embodiments the asthma severity filter includes a sleep disruption sub-filter, which is configured to be fired when the first plurality of survey results indicates that the subject's sleep is infrequently disrupted by symptoms of asthma, e.g., less than three or four times per month, and/or very frequently, e.g., more than four or five times per month. In some embodiments, a frequency of sleep disruptions, capable of firing the sleep disruption sub-filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the sleep disruption sub-filter is fired, the subject is not permitted to obtain the corticosteroid pharmaceutical composition over-the-counter (e.g., the method is terminated without authorizing provision of the corticosteroid pharmaceutical composition to the subject).

Referring to block 436, in some embodiments the asthma severity filter includes a rescue inhaler use sub-filter, which is configured to be fired when the first plurality of survey results indicates that the subject uses a rescue inhaler infrequently to control symptoms of asthma, e.g., on less than two or three days per week, and/or very frequently, e.g., on more five or six times per week. In some embodiments, a frequency of rescue inhaler use, capable of firing the rescue inhaler use sub-filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the rescue inhaler use sub-filter is fired, the subject is not permitted to obtain the corticosteroid pharmaceutical composition over-the-counter (e.g., the method is terminated without authorizing provision of the corticosteroid pharmaceutical composition to the subject).

Referring to block 438, in some embodiments the asthma severity filter includes an oral corticosteroid sub-filter, which is configured to be fired when the first plurality of survey results indicates that the subject uses an oral corticosteroid, e.g., to manage asthma exacerbations, frequently, e.g., more than one, two, or three times a year. In some embodiments, a frequency of oral corticosteroid use, capable of firing the oral corticosteroid sub-filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the oral corticosteroid sub-filter is fired, the subject is not permitted to obtain the corticosteroid pharmaceutical composition over-the-counter (e.g., the method is terminated without authorizing provision of the corticosteroid pharmaceutical composition to the subject).

Referring to block 440, in some embodiments the first plurality of survey results further includes or indicates whether the subject is allergic to the corticosteroid pharmaceutical composition. Accordingly, the first plurality of filters includes an adverse reaction filter. The adverse reaction filter is configured to be fired when the first plurality of survey results indicates that the subject is allergic to the corticosteroid pharmaceutical composition. In some embodiments, the adverse reaction filter is fired when the first survey results indicate that the subject has experienced an adverse reaction to a medication containing corticosteroid in the past. In some embodiments, the adverse reaction filter is fired when the first plurality of survey results indicates that subject is allergic to one or more ingredients (e.g., active ingredients and/or excipients) included in the corticosteroid pharmaceutical composition. If the adverse reaction filter is fired, the subject is not permitted to obtain the corticosteroid pharmaceutical composition pharmaceutical composition over-the-counter (e.g., the method is terminated without authorizing provision of the corticosteroid pharmaceutical composition to the subject).

Figure 7D:
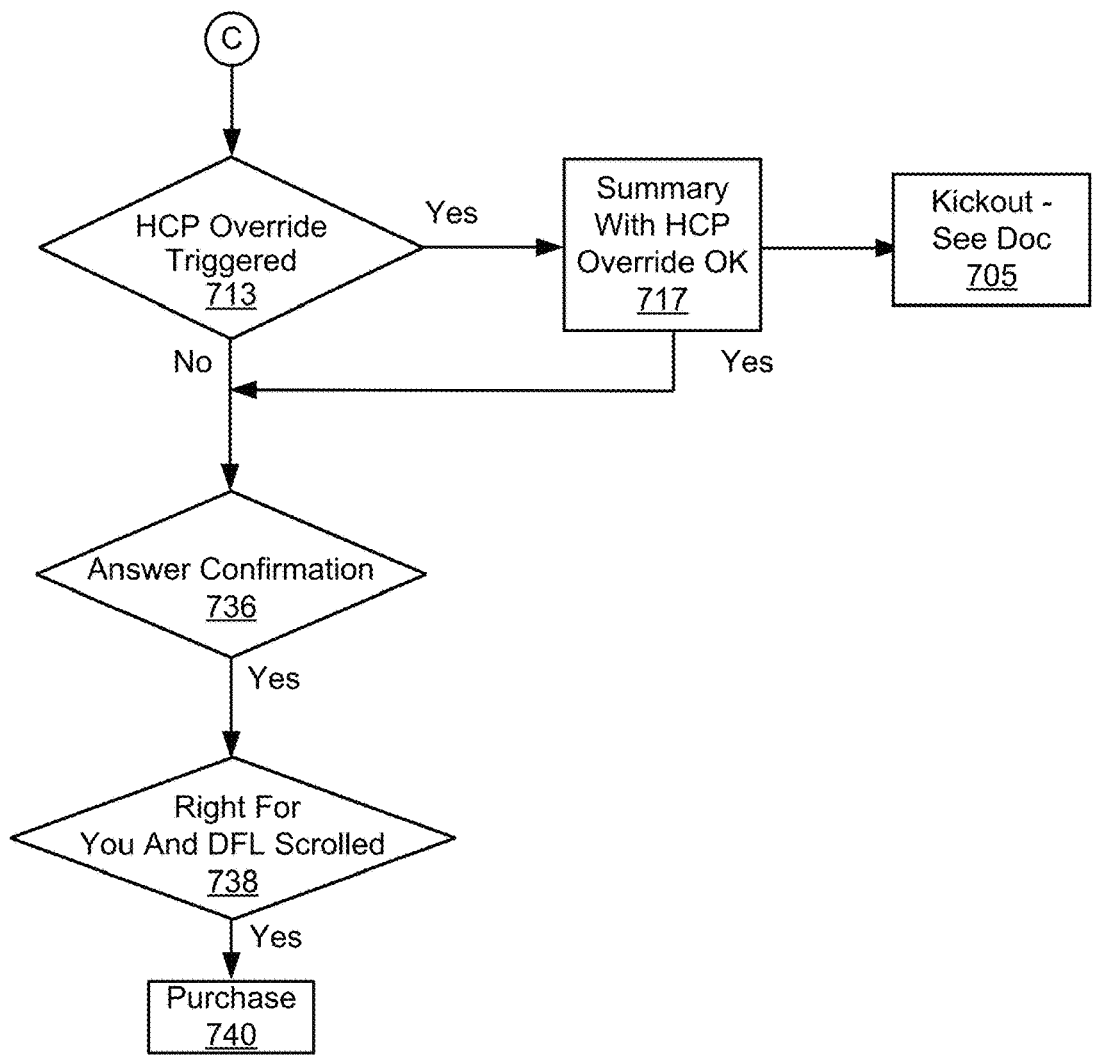

Referring to block 442 of FIG. 4D, the method also includes running all or a portion of the first survey results against a second plurality of filters of a second category class 220. When a respective filter in the second plurality of filters is fired, the subject is provided with a warning 226 corresponding to the respective filter (e.g., filter warning 226-4 corresponds to filter 222-4). In some embodiments, the warning 226 is provided as a next step, e.g., prior to applying survey results to any subsequent filters, after the corresponding filter is fired. For example, with respect to FIG. 7C, in some embodiments, e.g., when the ocular disease filter is triggered at 730, the device would provide the subject with a warning prior to proceeding to the drug interaction filter at 7432, e.g., requiring the subject confirm they have discussed their ocular disease or ocular problem with a health care provider, e.g., and the healthcare provider still recommends taking a corticosteroid pharmaceutical composition in order to proceed with the qualification. In some embodiments the warning 226 is provided after applying survey results to all subsequent filters. For example, as illustrated in FIGS. 7C and 7D, in some embodiments, e.g., when the ocular disease filter is triggered at 730, the device would proceed to the drug interaction filter at 738 prior to transmitting a warning to the subject, and then transmit all warnings corresponding to filters of the second category class, at 736, after survey results have been applied to all subsequent filters.

In some embodiments, the second plurality of filters 222 of the second category class 220 includes some or all of the filters listed in Table 3. For example, in some embodiments, the first plurality of filters results includes, or at least indicates, 2, 3, 4, 5, or all 6 of the filters listed in Table 3. In one embodiment, the first plurality of filters includes, all of filters 2-5 as provided in Table 3.

TABLE 3

Example filters for risk factors associated with qualifying a subject for an over-the-counter provision of a corticosteroid pharmaceutical composition.

| Filter | Example Criteria |
| --- | --- |
| 1a | a liver disease filter |
| 2a | an infection filter |
| 3a | a surgery filter |
| 4a | a bone density filter |
| 5a | an ocular disease filter |
| 6a | a drug interaction filter |

Referring to block 444, in some embodiments, the second plurality of filters includes a liver disease filter (e.g., filter 1a in Table 3). The liver disease filter is configured to be fired at least when the first plurality of survey results indicate that the subject has a liver problem. In some embodiments, liver problems that are capable of triggering the first liver disease filter include impaired hepatic function, acute liver failure, and cholestasis. When the liver disease filter is fired, the device transmits a warning corresponding to the liver disease filter, and requires the user to acknowledge the warning before authorizing a provision of the corticosteroid pharmaceutical composition.

Referring to block 446, in some embodiments, the second plurality of filters includes an infection filter (e.g., infection filter 222-1 in FIG. 3 and/or filter 2a in Table 3). The infection filter is configured to be fired at least when the first plurality of survey results indicates that the subject has a severe, untreated infection. In some embodiments, severe infections, which are capable of triggering the infection filter, include a fungal infection, a bacterial infection, a viral infection, a parasitic infection, tuberculosis infection of the respiratory tract, untreated systemic infections, gastroenteritis, and herpes simplex infection of the eye (e.g., ocular herpes simplex). When the infection filter is fired, the device transmits a warning corresponding to the infection filter, and requires the user to acknowledge the warning before authorizing a provision of the corticosteroid pharmaceutical composition.

Referring to block 448, in some embodiments, the second plurality of filters includes a surgery filter (e.g., surgery filter 222-2 in FIG. 3 and/or filter 3a in Table 3). The surgery filter is configured to be fired at least when the first plurality of survey results indicates that the subject has is planning on undergoing surgery. In some embodiments, the surgery filter is configured to be fired at least when the first plurality of survey results indicates that the subject is planning on being exposed to an event that produces an adrenal insufficiency. In some embodiments, the surgery filter is configured to be fired at least when the first plurality of survey results indicates that the subject has severe electrolyte loss due to a recent surgery. In some embodiments, the surgery filter is configured to be fired at least when the first plurality of survey results indicates that the subject is in a postoperative state. In some embodiments, the surgery filter is configured to be fired at least when the first plurality of survey results indicates that the subject is in a stress inducing state. In some embodiments, the surgery filter is configured to be fired at least when the first plurality of survey results indicates that the subject has hypocorticism. When the surgery filter is fired, the device transmits a warning corresponding to the surgery filter, and requires the user to acknowledge the warning before authorizing a provision of the corticosteroid pharmaceutical composition.

Referring to block 450, in some embodiments, the second plurality of filters includes a bone density filter (e.g., bone density filter 222-3 in FIG. 3 and/or filter 4a in Table 3). The bone density filter is configured to be fired at least when the first plurality of survey results indicates that the subject has a decreased bone mineral density. In some embodiments, the bone density filter is configured to be fired at least when the first plurality of survey results indicates that the subject is at risk for decreased bone mineral density. Risk factors for decreased bone mineral density include inactivity for a long period of time, a family history of osteoporosis, a female going through or post-menopause, smoking, tobacco use, poor nutrition, advanced age, and a history of using medications than decrease bone density (e.g., anti-convulsants or corticosteroids). When the bone density filter is fired, the device transmits a warning corresponding to the bone density filter, and requires the user to acknowledge the warning before authorizing a provision of the corticosteroid pharmaceutical composition.

Referring to block 452, in some embodiments, the second plurality of filters includes an ocular disease filter (e.g., ocular disease filter 222-4 in FIG. 3 and/or filter 5a in Table 3). The ocular disease filter is configured to be fired at least when the first plurality of survey results indicates that the subject has ever had cataracts or glaucoma. In some embodiments, the ocular disease filter is configured to be fired at least when the first plurality of survey results indicates that the subject has an increased intraocular pressure. When the ocular disease filter is fired, the device transmits a warning corresponding to the ocular disease filter, and requires the user to acknowledge the warning before authorizing a provision of the corticosteroid pharmaceutical composition.

Referring to blocks 454-456, in some embodiments, the second plurality of filters includes a drug interaction filter (e.g., filter 6a in Table 3). The drug interaction filter is configured to be fired at least when the first plurality of survey results indicates that the subject indicates that the subject is taking a medication that interacts (e.g., a pharmacokinetic interaction and/or a pharmacodynamic interaction) with the corticosteroid pharmaceutical composition. In some embodiments, the drug interaction filter is fired when the first plurality of survey results indicates that the subject is taking a medication selected from the group consisting of a corticosteroid medicine, an anticonvulsant, an immunosuppressant, ketoconazole, a medicine for the liver, and a prescription anti-retroviral. In some embodiments, the drug interaction filter is fired when the first plurality of survey results indicates that the subject is taking a strong CYP3A4 inhibitor such as ritonavir, atazanavir, clarithromycin, indinavir, itraconazole, nefazodone, nelfinavir, saquinavir, telithromycin, etc. When the drug interaction filter is fired, the device transmits a warning corresponding to the drug interaction filter, and requires the user to acknowledge the warning before authorizing a provision of the corticosteroid pharmaceutical composition.

The identity of drugs that are capable of triggering the drug interaction filter vary from one corticosteroid to another corticosteroid. The skilled artisan will know of drugs that interact with one corticosteroid but not another. Inclusion of a drug within the drug interaction filter is dependent upon the identity and/or the dosage of the corticosteroid pharmaceutical composition being authorized for over-the-counter use.

In some implementations, a drug that interacts with a corticosteroid pharmaceutical composition is included within a filter 216 in the first filter category class 214, rather than within drug interaction filter 222 of the second filter category class 220. For example, according to some implementations, a particular drug included in drug-interaction filter 222 (e.g., as a risk factor) for a first corticosteroid pharmaceutical composition, but included in a filter in the first plurality of filters (e.g., as a contraindication) for a second corticosteroid pharmaceutical composition. However, a person skilled in the art will know whether to include a certain drug within drug interaction filter 222 or as a separate filter 216 in the first plurality of filters, based on the severity and risk of the drug interaction with the particular identity and dosage of the corticosteroid being authorized for over-the-counter use.

It is contemplated that, in some embodiments, any one or more of the filters provided in Table 3 will not be included in the second plurality of filters. For example, in some embodiments, a characteristic associated with a particular survey result will be informative when qualifying a subject for one particular corticosteroid pharmaceutical composition but not for another corticosteroid pharmaceutical composition. Accordingly, it is contemplated that the second plurality of filters includes any sub-set of filters provided in Table 3. Likewise, the skilled artisan may know of other filters, not provided in Table 3, that may be combined with any subset of the filters provided in Table 3 to form the second plurality of filters results used in the methods described herein.

Contraindications and risk factors described in the present disclosure are non-exhaustive. The skilled artisan may know of other contraindications for a particular the corticosteroid pharmaceutical composition and/or treat risk factors as contraindications dependent upon the intended use of the corticosteroid pharmaceutical composition. In some embodiments, contraindications for use of a prescription-strength pharmaceutical agent are treated only as risk factors, or not at all, when qualifying a subject for a lower-dose OTC use of a corticosteroid pharmaceutical composition.

Accordingly, it will be appreciated that the survey questions 208, 212, and filters 216, 222 applied to the survey answers thereof, may vary depending upon the corticosteroid pharmaceutical composition being distributed. This is due to differences in the contraindication profiles of the various the corticosteroid pharmaceutical compositions, e.g., due to different drug-drug interactions, routes of drug clearance, etc. of the different the corticosteroid.

Figure 6:
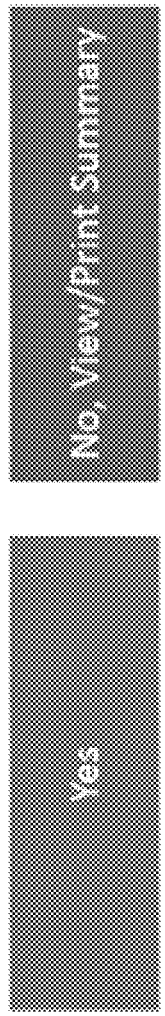
FIG. 6 illustrates feedback from a first survey in accordance with an embodiment of the present disclosure.

Referring to block 458, in some embodiments the warning 226 corresponding to a respective filter 222 in the second plurality of filters includes a prompt for the subject to indicate whether they have discussed the risk factor underlying the respective filter in the second plurality of filters that was fired with a health care practitioner (e.g., a licensed medical practitioner), e.g., and that the health care practitioner recommended taking a corticosteroid pharmaceutical composition in view of the underlying risk factor. Accordingly, acknowledgement is obtained from the subject when the subject indicates that they have discussed the risk factor underlying the respective filter in the second plurality of filters that was fired with a health care provider. For example, message 602 in FIG. 6 illustrates an example warning that is generic to any fired filters. In some embodiments, the warning is specific to a particular filter (e.g., filter warning 226 in FIG. 2), e.g., and optionally communicates to the user why the warning was issued.

In some embodiments, an acknowledgment from the user is verified by the health care practitioner (e.g., the method requires verification in order for authorization of the provision of the corticosteroid pharmaceutical composition), e.g., in order to verify an accuracy of the survey results of the subject. In some embodiments, e.g., when the acknowledgment is verified by the heath care practitioner, the subject is deemed a trusted subject, such that verification of future results is not required.

Referring to block 460 of FIG. 4E, the method includes obtaining acknowledgment from the subject for any warning 226 issued to the subject by any filter 222 in the second plurality of filters. In some embodiments, acknowledgment from the subject is a written acknowledgement, a verbal acknowledgment, or an electronic acknowledgment such as an electronic signature. If a filter 216 in the first plurality of filters fires, the subject is denied access to the over-the-counter corticosteroid pharmaceutical composition.

Blocks 462-472. Referring to block 472 of FIG. 4E, the process control proceeds to the fulfillment process when no filter 216 in the first plurality of filters has been fired and the subject has acknowledged each warning 226 associated with each filter 222 in the second plurality of filters that was fired. In some embodiments, the fulfillment process includes storing an indication in a user profile 234 of an initial order date and/or destination for the corticosteroid pharmaceutical composition. The initial order date is utilized, for example, to verify at least a refill status of a provision of the corticosteroid. The initial order date is also utilized, for example, to determine an elapsed period of time between requests for qualification. In some embodiments, such determinations are used to ensure that certain tests (e.g., FEV1 tests) are taken regularly.

The fulfillment process further includes communicating an over-the-counter drug facts label 230 for the corticosteroid pharmaceutical composition to the subject. In some embodiments, the drug facts label is communicated to the subject in real-time, e.g., within the same user interface as used for the qualification process. In some embodiments, the over-the-counter drug facts label 230 specifies what the corticosteroid is for (e.g., treating and/or preventing symptoms of asthma), what dosage the subject is being authorized to take, and/or any risks associated with taking corticosteroid pharmaceutical composition (e.g., drug-drug interactions, pharmacokinetic interactions, adverse reactions, etc.)

In some embodiments of the aspects described herein, the subject is administered, or qualified for a provision of, a dosage of from 45 to 360 mcg of budesonide twice per day. In some embodiments of the aspects described herein, the subject is administered, or qualified for a provision of, a dosage of from 90 to 180 mcg of budesonide twice per day. In some embodiments, upon confirmation from the subject that the over the counter drug facts label 230 has been received and read, the subject is authorized for provision of a dosage of 90 mcg of budesonide twice per day (e.g., 180 mcg per day). In some embodiments, upon confirmation from the subject that the over the counter drug facts label 230 has been received and read, the subject is authorized for provision of a dosage of 180 mcg of budesonide twice per day. In some embodiments, upon confirmation from the subject that the over the counter drug facts label 230 has been received and read, the subject is authorized for provision of a dosage of 270 mcg of budesonide twice per day. In some embodiments, upon confirmation from the subject that the over the counter drug facts label 230 has been received and read, the subject is authorized for provision of a dosage of 360 mcg of budesonide twice per day. In some embodiments, upon confirmation from the subject that the over the counter drug facts label 230 has been received and read, the subject is authorized for provision of a dosage of 540 mcg of budesonide twice per day. In some embodiments, upon confirmation from the subject that the over the counter drug facts label 230 has been received and read, the subject is authorized for provision of a dosage of 720 mcg of budesonide twice per day.

In some embodiments of the aspects described herein, the subject is administered, or qualified for a provision of, a dosage of from 44 to 352 mcg of fluticasone propionate twice per day. In some embodiments of the aspects described herein, the subject is administered, or qualified for a provision of, a dosage of from 88 to 176 mcg of fluticasone propionate twice per day. In some embodiments, upon confirmation from the subject that the over the counter drug facts label 230 has been received and read, the subject is authorized for provision of a dosage of 44 mcg of fluticasone propionate twice per day (e.g., 88 mcg per day). In some embodiments, upon confirmation from the subject that the over the counter drug facts label 230 has been received and read, the subject is authorized for provision of a dosage of 88 mcg of fluticasone propionate twice per day. In some embodiments, upon confirmation from the subject that the over the counter drug facts label 230 has been received and read, the subject is authorized for provision of a dosage of 132 mcg of fluticasone propionate twice per day. In some embodiments, upon confirmation from the subject that the over the counter drug facts label 230 has been received and read, the subject is authorized for provision of a dosage of 176 mcg of fluticasone propionate twice per day. In some embodiments, upon confirmation from the subject that the over the counter drug facts label 230 has been received and read, the subject is authorized for provision of a dosage of from 220 mcg of fluticasone propionate twice per day.

In some embodiments of the aspects described herein, the subject is administered, or qualified for a provision of, a dosage of from 20 to 160 mcg of beclomethasone dipropionate twice per day. In some embodiments of the aspects described herein, the subject is administered, or qualified for a provision of, a dosage of from 40 to 80 mcg of beclomethasone dipropionate twice per day. In some embodiments, upon confirmation from the subject that the over the counter drug facts label 230 has been received and read, the subject is authorized for provision of a dosage of 40 mcg of beclomethasone dipropionate twice per day (e.g., 80 mcg per day). In some embodiments, upon confirmation from the subject that the over the counter drug facts label 230 has been received and read, the subject is authorized for provision of a dosage of 80 mcg of beclomethasone dipropionate twice per day. In some embodiments, upon confirmation from the subject that the over the counter drug facts label 230 has been received and read, the subject is authorized for provision of a dosage of 100 mcg of beclomethasone dipropionate twice per day. In some embodiments, upon confirmation from the subject that the over the counter drug facts label 230 has been received and read, the subject is authorized for provision of a dosage of 120 mcg of beclomethasone dipropionate twice per day. In some embodiments, upon confirmation from the subject that the over the counter drug facts label 230 has been received and read, the subject is authorized for provision of a dosage of 200 mcg of beclomethasone dipropionate twice per day. In some embodiments, upon confirmation from the subject that the over the counter drug facts label 230 has been received and read, the subject is authorized for provision of a dosage of 320 mcg of beclomethasone dipropionate twice per day.

In some embodiments of the aspects described herein, the subject is administered, or qualified for a provision of, a dosage of from 50 to 200 mcg of fluticasone furoate per day. In some embodiments of the aspects described herein, the subject is administered, or qualified for a provision of, a dosage of 100 mcg of fluticasone furoate per day. In some embodiments, upon confirmation from the subject that the over the counter drug facts label 230 has been received and read, the subject is authorized for provision of a dosage of 50 mcg of fluticasone furoate per day. In some embodiments, upon confirmation from the subject that the over the counter drug facts label 230 has been received and read, the subject is authorized for provision of a dosage of 100 mcg of fluticasone furoate per day. In some embodiments, upon confirmation from the subject that the over the counter drug facts label 230 has been received and read, the subject is authorized for provision of a dosage of 150 mcg of fluticasone furoate per day. In some embodiments, upon confirmation from the subject that the over the counter drug facts label 230 has been received and read, the subject is authorized for provision of a dosage of 200 mcg of fluticasone furoate per day.

In some embodiments of the aspects described herein, the subject is administered, or qualified for a provision of, a dosage of from 40 to 320 mcg of ciclesonide twice per day. In some embodiments of the aspects described herein, the subject is administered, or qualified for a provision of, a dosage of from 80 to 160 mcg of ciclesonide twice per day. In some embodiments, upon confirmation from the subject that the over the counter drug facts label 230 has been received and read, the subject is authorized for provision of a dosage of 40 mcg of ciclesonide twice per day (e.g., 80 mcg per day). In some embodiments, upon confirmation from the subject that the over the counter drug facts label 230 has been received and read, the subject is authorized for provision of a dosage of 80 mcg of ciclesonide twice per day. In some embodiments, upon confirmation from the subject that the over the counter drug facts label 230 has been received and read, the subject is authorized for provision of a dosage of 100 mcg of ciclesonide twice per day. In some embodiments, upon confirmation from the subject that the over the counter drug facts label 230 has been received and read, the subject is authorized for provision of a dosage of 120 mcg of ciclesonide twice per day. In some embodiments, upon confirmation from the subject that the over the counter drug facts label 230 has been received and read, the subject is authorized for provision of a dosage of 200 mcg of ciclesonide twice per day. In some embodiments, upon confirmation from the subject that the over the counter drug facts label 230 has been received and read, the subject is authorized for provision of a dosage of 320 mcg of ciclesonide twice per day.

In some embodiments of the aspects described herein, the subject is administered, or qualified for a provision of, a dosage of from 110 to 880 mcg of mometasone furoate per day. In some embodiments of the aspects described herein, the subject is administered, or qualified for a provision of, a dosage of from 220 to 440 mcg of mometasone furoate per day. In some embodiments, upon confirmation from the subject that the over the counter drug facts label 230 has been received and read, the subject is authorized for provision of a dosage of 100 mcg of mometasone furoate per day. In some embodiments, upon confirmation from the subject that the over the counter drug facts label 230 has been received and read, the subject is authorized for provision of a dosage of 200 mcg of mometasone furoate per day. In some embodiments, upon confirmation from the subject that the over the counter drug facts label 230 has been received and read, the subject is authorized for provision of a dosage of 300 mcg of mometasone furoate per day. In some embodiments, upon confirmation from the subject that the over the counter drug facts label 230 has been received and read, the subject is authorized for provision of a dosage of 400 mcg of mometasone furoate per day. In some embodiments, upon confirmation from the subject that the over the counter drug facts label 230 has been received and read, the subject is authorized for provision of a dosage of 500 mcg of mometasone furoate per day. In some embodiments, upon confirmation from the subject that the over the counter drug facts label 230 has been received and read, the subject is authorized for provision of a dosage of 600 mcg of mometasone furoate per day. In some embodiments, upon confirmation from the subject that the over the counter drug facts label 230 has been received and read, the subject is authorized for provision of a dosage of 700 mcg of mometasone furoate per day. In some embodiments, upon confirmation from the subject that the over the counter drug facts label 230 has been received and read, the subject is authorized for provision of a dosage of 800 mcg of mometasone furoate per day.

Referring to blocks 470 and 472, in some embodiments the fulfillment process further includes authorizing provision of the corticosteroid composition to the subject. The authorization occurs upon confirmation from the subject that the over-the-counter drug facts label 230 has been received and read by the subject. In some embodiments, this authorization includes a destination associated with the subject (block 470). In some embodiments, the destination associated with the subject is stored in the user profile 234. In some embodiments, the destination associated with the subject is a physical address including a street address, a Post Office box, a pharmacy associated with the subject, a health care provider associated with the subject, and/or one or more coordinates (e.g., longitude, latitude, elevation). In some embodiments, the provision of the corticosteroid pharmaceutical composition to the subject includes shipping the corticosteroid pharmaceutical composition to the physical address associated with the subject (block 472). In some embodiments, the provision of the corticosteroid pharmaceutical composition to the subject includes shipping the corticosteroid pharmaceutical composition to a pharmacy associated and/or a location associated with a health care provider of the subject and/or an office of a medical practitioner associated with the subject.

Blocks 474-512. Referring to blocks 484-512 of FIGS. 4E-4I, a re-fulfillment process will be described infra. In some embodiments, the present disclosure provides a method for qualifying a subject for a refill of a corticosteroid pharmaceutical composition. In some embodiments, the qualification for a refill of the corticosteroid pharmaceutical composition follows an initial qualification of the subject, as described herein. In some embodiments, the qualification for a refill of the corticosteroid pharmaceutical composition follows issuance of a prescription to the subject for the corticosteroid pharmaceutical composition. For example, in some embodiments, a subject who is new to the qualification process is asked whether they previously received a prescription for the corticosteroid pharmaceutical composition and, if the subject indicates that they have not previously received a prescription, the subject is directed to an initial qualification method and, if the subject indicates that they have previously received a prescription, the subject is directed to the refill qualification method, e.g., as described below.

Referring to block 474, in some embodiments a re-fulfillment procedure is performed. The re-fulfillment procedure is responsive to receiving a re-order request from the subject for the corticosteroid pharmaceutical composition. In some embodiments, a prompt to initiate the re-fulfillment procedure is sent to user device 102 associated with the subject after a predetermined amount of time associated with a duration of dosages previously delivered to the subject (e.g., the user is reminded to fulfill their order of the corticosteroid pharmaceutical composition just before, or just after, the user is scheduled to run out of a previously delivered provision).

Referring to blocks 476-478 of FIG. 4F, in some embodiments the re-fulfillment procedure includes conducting a second survey of the subject. The second survey is configured to obtain a second plurality of survey results. These results are derived from corresponding survey questions (e.g., the device transmits one or more survey questions to the user, prompting a response, and then receives a response to the one or more survey questions back from the subject). In some embodiments, the second plurality of survey results include, or at least indicate, some or all of the subject characteristics listed in Table 4. For example, in some embodiments, the second plurality of survey results includes, or at least indicates, 1, 2, 3, 4, 5, 6, 7, 8, 9, 10, 11, 12, 13, or all 14 of the characteristic listed in Table 4. In one embodiment, the second survey results include, or at least indicate, at least characteristics 2-8 and 10-13, as provided in Table 4.

In some embodiments, the second survey results include, or at least indicate, at least: whether the subject is already taking a steroid medication (e.g., responsive to a survey question that is associated with and/or applied to (808) a steroid medication filter of a first category class), a pulmonary function status of the subject (e.g., responsive to a survey question that is associated with and/or applied to (810) a pulmonary function filter 216-6 of a first category class), whether the subject has observed an improvement in their symptoms of asthma since first receiving a provision of the corticosteroid pharmaceutical composition (e.g., responsive to a survey question that is associated with and/or applied to (812-818) an asthma reduction filter 216-7 of a first category class), whether the subject has or has been in contact with someone having chicken pox, measles, or tuberculosis since receiving their last provision of the corticosteroid pharmaceutical composition (e.g., responsive to a survey question that is associated with and/or applied to (820) an infectious disease contact filter 222-6 of a second category class 220-2), whether the subject has experienced symptoms of an infection since receiving their last provision of the corticosteroid pharmaceutical composition (e.g., responsive to a survey question that is associated with and/or applied to (822) a symptoms of infection filter 222-6 of a second category class), a vision deterioration status of the subject (e.g., responsive to a survey question that is associated with and/or applied to (824) a vision deterioration filter 222-7 of a second category class), an oral health status of the subject (e.g., responsive to a survey question that is associated with and/or applied to (826) an oral health filter 222-8 of a second category class), whether the subject has an untreated infection (e.g., responsive to a survey question that is associated with and/or applied to (830) an infection filter 222-9 of a second category class), a surgery status of the subject (e.g., responsive to a survey question that is associated with and/or applied to (832) a surgery filter 222-10 of a second category class), a bone density status of the subject (e.g., responsive to a survey question that is associated with and/or applied to (834) a bone density filter 222-11 of a second category class), and whether the subject has developed cataracts or glaucoma since receiving their last provision of the corticosteroid pharmaceutical composition (e.g., responsive to a survey question that is associated with and/or applied to (836) an ocular disease filter 222-12 of a second category class).

In some embodiments, the second survey includes questions that elicit responses providing some or all of the characteristics listed in Table 4. In some embodiments, the second survey includes questions corresponding to each of the survey results required for the methods described herein. In other embodiments, the second survey includes questions corresponding to only a subset of the survey results required for the methods described herein. In some embodiments, other survey results required for the methods described herein are acquired through other means (e.g., upon registration/subscription for a service associated with qualifying the subject for over-the-counter medication, from a healthcare provider, from a prior survey, from a database associated with a pharmacy, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a bone mineral density determined for the subject).

TABLE 4

Example characteristics for re-qualifying a subject for an over-the-counter provision of a corticosteroid pharmaceutical composition.

| Result | Example Characteristics |
|---|---|
| 1 | whether the subject has developed a dairy allergy |
| 2 | whether the subject is already taking a steroid medication |
| 3 | a pulmonary function status of the subject |
| 4 | whether the subject has observed an improvement in the symptoms of asthma |
| 5 | whether the subject has or has been in contact with someone having chicken pox, measles, or tuberculosis |
| 6 | whether the subject has experienced symptoms of an infection |
| 7 | a vision deterioration status of the subject |
| 8 | an oral health status of the subject |
| 9 | whether the subject has developed a liver problem |
| 10 | whether the subject has an untreated infection |
| 11 | a surgery status of the subject |
| 12 | a bone density status of the subject |
| 13 | whether the subject has developed cataracts or glaucoma |
| 14 | whether the subject has started taking a medication that interacts with the corticosteroid pharmaceutical composition |

It is contemplated that, in some embodiments, any one or more of the survey questions provided in Table 4 will not be included in the second survey (e.g., will not be used for the reassessment). For example, in some embodiments, a characteristic associated with a particular survey questions will be informative when qualifying a subject for one particular corticosteroid but not for another corticosteroid. For instance, a survey question is queried for budesonide qualifying surveys but not for ciclesonide qualifying surveys. The skilled artisan will recognize that different corticosteroids carry different risk and drug interaction profiles. Accordingly, survey information required for qualifying a subject for access to one corticosteroid with a known adverse drug interaction may not be necessary for qualifying the same subject for access to a second corticosteroid.

Accordingly, it is contemplated that the second survey questions elicit responses to any sub-set of survey results provided in Table 4. For brevity, all possible combinations of the characteristics provided in Table 4 are not specifically delineated here. However, the skilled artisan will easily be able to envision any particular subset of survey questions designed to elicit responses to any subset of characteristics provided in Table 4. Likewise, the skilled artisan may know of other survey questions, not provided in Table 4, that may be combined with any subset of the survey questions provided in Table 4 to form the second survey questions used in the methods described herein.

Referring to block 480, all or a portion the results are run against a third plurality of filters of the first category class. When a respective filter in the third plurality of filters is fired (e.g., when a survey result indicates that a triggering condition 218 has been met), the subject is deemed not qualified for the corticosteroid pharmaceutical composition and the method is terminated without delivery of the corticosteroid pharmaceutical composition.

Referring to blocks 482-498, specific filters in the third plurality of filters and their exemplary triggering conditions that cause the corresponding filter to fire are detailed.

In some embodiments, the third plurality of filters of the first category class 214 includes some or all of the filters 216 listed in Table 5. For example, in some embodiments, the first plurality of filters results includes, or at least indicate, 2, 3, or all 4 of the filters listed in Table 5. In one embodiment, the third plurality of filters includes, or at least indicates, all of filters all of filters 1-4 as provided in Table 5.

TABLE 5

Exemplary Third Plurality of Filters of the First Category Class.

| Filter | Example Criteria |
|---|---|
| 1a | A dairy allergy filter |
| 2a | a steroid medication filter |
| 3a | a pulmonary function filter |
| 4a | an asthma reduction filter |

It is contemplated that, in some embodiments, any one or more of the filters provided in Table 5 will not be included in the third plurality of filters. For example, in some embodiments, a characteristic associated with a particular survey result will be informative when qualifying a subject for one particular corticosteroid but not for another corticosteroid. Likewise, the skilled artisan may know of other filters, not provided in Table 5, which may be combined with any subset of the filters provided in Table 5 to form the third plurality of filters results used in the methods described herein. For brevity, all possible combinations of the filters provided in Table 5 are not specifically delineated here.

Referring to block 482, in some embodiments the third plurality of filters includes a dairy allergy filter, e.g., as described above in relation to the first survey. In some embodiments, the dairy allergy filter is configured to be fired at least when the second plurality of survey results indicates that the subject has developed a severe dairy allergy since receiving their last provision of the corticosteroid pharmaceutical composition. When the second allergy filter is fired, the subject is not permitted to obtain the corticosteroid pharmaceutical composition over-the-counter (e.g., the method is terminated without authorizing re-provision of the corticosteroid pharmaceutical composition to the subject).

Referring to block 494, in some embodiments the third plurality of filters includes a steroid medication filter, e.g., as described above in relation to the first survey. In some embodiments, the steroid medication filter is configured to be fired at least when the second plurality of survey results indicates that the subject has begun taking another steroid composition (e.g., for the treatment of asthma, allergies, and/or a skin rash). When the steroid medication filter is fired, the subject is not permitted to obtain the corticosteroid pharmaceutical composition over-the-counter (e.g., the method is terminated without authorizing re-provision of the corticosteroid pharmaceutical composition to the subject).

Referring to blocks 486-488, in some embodiments the third plurality of filters includes a second pulmonary function filter, e.g., as described above in relation to the first survey. In some embodiments, the pulmonary function filter is configured to be fired at least when the second plurality of survey results indicates that the subject has severely compromised pulmonary function, e.g., warranting a stronger, prescription medication and/or treatment under supervision of a medical professional. In some embodiments, the pulmonary function filter queries a measured lung function of the subject, e.g., from a forced expiratory volume measured over one second (FEV1) assay. In some embodiments, a lung function value of no more than 80%, e.g., of a predicted volume determined using a forced expiratory volume measurement, is sufficient to fire the pulmonary function filter. In some embodiments, a compromised pulmonary function, capable of firing a pulmonary function filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the pulmonary function filter is fired, the subject is not permitted to obtain the corticosteroid pharmaceutical composition over-the-counter (e.g., the method is terminated without authorizing provision of the corticosteroid pharmaceutical composition to the subject).

Referring to block 490 of FIG. 4G, in some embodiments the third plurality of filters includes an asthma reduction filter. In some embodiments, the asthma reduction filter is configured to be fired at least when the second plurality of survey results indicates that the subject has not observed an improvement in symptoms of asthma function since receiving a first provision of the corticosteroid pharmaceutical composition, e.g., when the over-the-counter corticosteroid pharmaceutical composition is not providing a therapeutic benefit. In some embodiments, the asthma reduction filter is implemented as one or more sub-filters, e.g., that query the frequency with which the subject experiences episodes of asthma, or a set of criteria as described for the one or more sub-filters considered together (e.g., using a classification algorithm to classify an asthma severity of the subject). If the asthma reduction filter is fired, e.g., indicating that the subject is not benefiting from the over-the-counter corticosteroid pharmaceutical composition, the subject is not permitted to obtain the corticosteroid pharmaceutical composition over-the-counter (e.g., the method is terminated without authorizing provision of the corticosteroid pharmaceutical composition to the subject). When the asthma reduction filter is fired, the subject is not permitted to obtain the corticosteroid pharmaceutical composition over-the-counter (e.g., the method is terminated without authorizing re-provision of the corticosteroid pharmaceutical composition to the subject).

Referring to block 492, in some embodiments the asthma reduction filter includes an asthma frequency sub-filter, which is configured to be fired when the first plurality of survey results indicates that the subject experiences symptoms of asthma frequently, e.g., more than two or three times per week (e.g., which has a lower threshold than a corresponding allergy severity threshold used during the initial assessment of a subject, ensuring the subject is receiving a therapeutic benefit from the corticosteroid composition). In some embodiments, a frequency of asthmatic symptoms, capable of firing the asthma frequency sub-filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the asthma frequency sub-filter is fired, the subject is not permitted to obtain the corticosteroid pharmaceutical composition over-the-counter (e.g., the method is terminated without authorizing re-provision of the corticosteroid pharmaceutical composition to the subject).

Referring to block 494, in some embodiments the asthma reduction filter includes a sleep disruption sub-filter, which is configured to be fired when the first plurality of survey results indicates that the subject's sleep is frequently disrupted, e.g., more than two or three times per month (e.g., which has a lower threshold than a corresponding allergy severity threshold used during the initial assessment of a subject, ensuring the subject is receiving a therapeutic benefit from the corticosteroid composition). In some embodiments, a frequency of sleep disruptions, capable of firing the sleep disruption sub-filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the sleep disruption sub-filter is fired, the subject is not permitted to obtain the corticosteroid pharmaceutical composition over-the-counter (e.g., the method is terminated without authorizing re-provision of the corticosteroid pharmaceutical composition to the subject).

Referring to block 496, in some embodiments the asthma reduction filter includes a rescue inhaler use sub-filter, which is configured to be fired when the first plurality of survey results indicates that the subject uses a rescue inhaler frequently, e.g., on more than two or three days per week (e.g., which has a lower threshold than a corresponding allergy severity threshold used during the initial assessment of a subject, ensuring the subject is receiving a therapeutic benefit from the corticosteroid composition). In some embodiments, a frequency of rescue inhaler use, capable of firing the rescue inhaler use sub-filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the rescue inhaler use sub-filter is fired, the subject is not permitted to obtain the corticosteroid pharmaceutical composition over-the-counter (e.g., the method is terminated without authorizing provision of the corticosteroid pharmaceutical composition to the subject).

Referring to block 498, in some embodiments the asthma reduction filter includes an oral corticosteroid sub-filter, which is configured to be fired when the first plurality of survey results indicates that the subject uses an oral corticosteroid, e.g., to manage asthma exacerbations, frequently, e.g., more than one, two, or three times a year. In some embodiments, a frequency of oral corticosteroid use, capable of firing the oral corticosteroid sub-filter, is set according to a set of healthcare guidelines, which may change over time, and/or vary on a jurisdiction-by-jurisdiction basis. For example, the National Heart, Lung, and Blood Institute Guidelines for the Diagnosis and Management of Asthma (EPR-3) (2007), the content of which is incorporated herein by reference. If the oral corticosteroid sub-filter is fired, the subject is not permitted to obtain the corticosteroid pharmaceutical composition over-the-counter (e.g., the method is terminated without authorizing provision of the corticosteroid pharmaceutical composition to the subject).

Figure 8A:
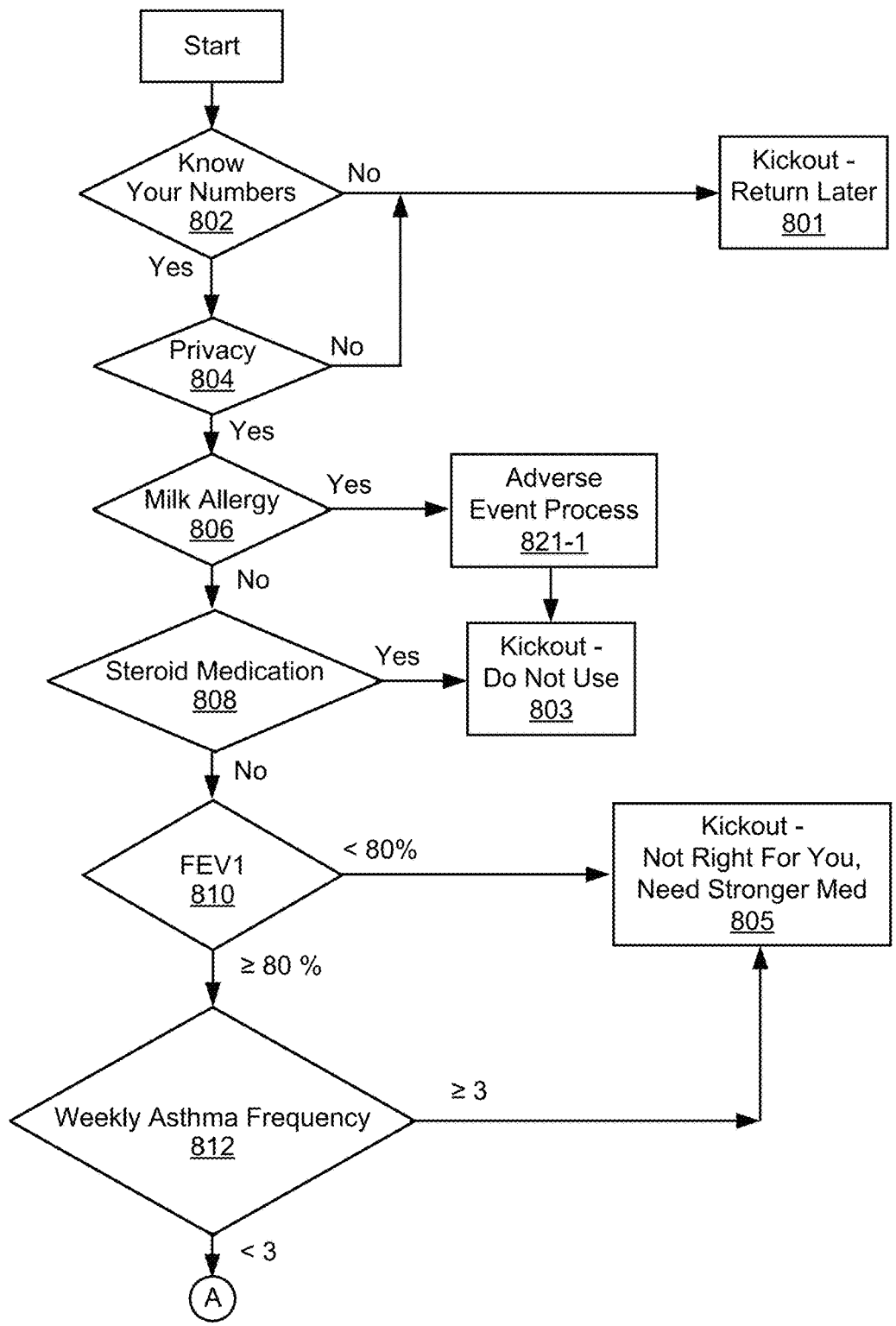
FIGS. 8A, 8B, 8C, and 8D collectively illustrate an example method for qualifying a subject for a refill of an over-the-counter provision of corticosteroid pharmaceutical composition in accordance with an embodiment of the present disclosure.
Figure 8B:
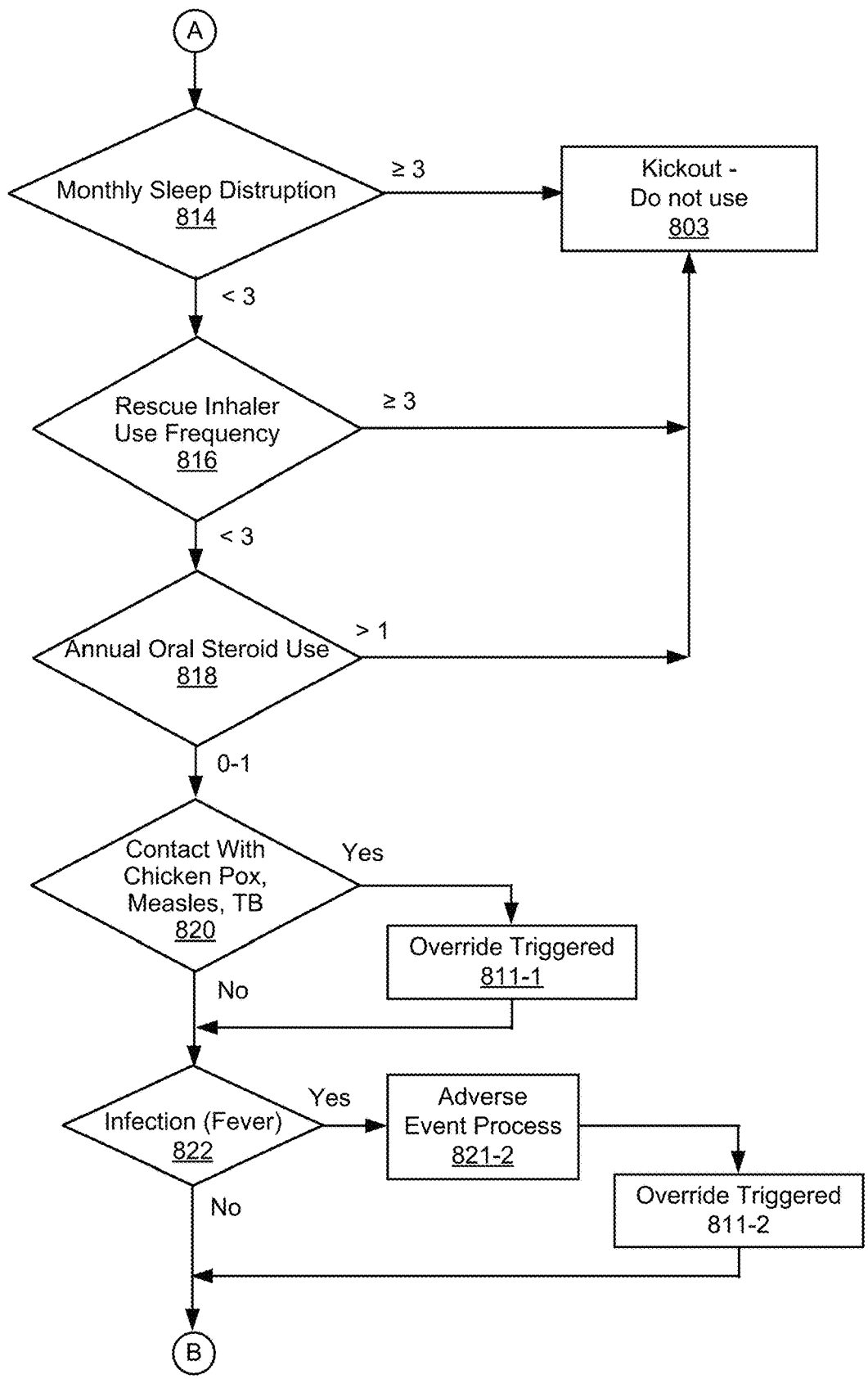
Figure 8C:
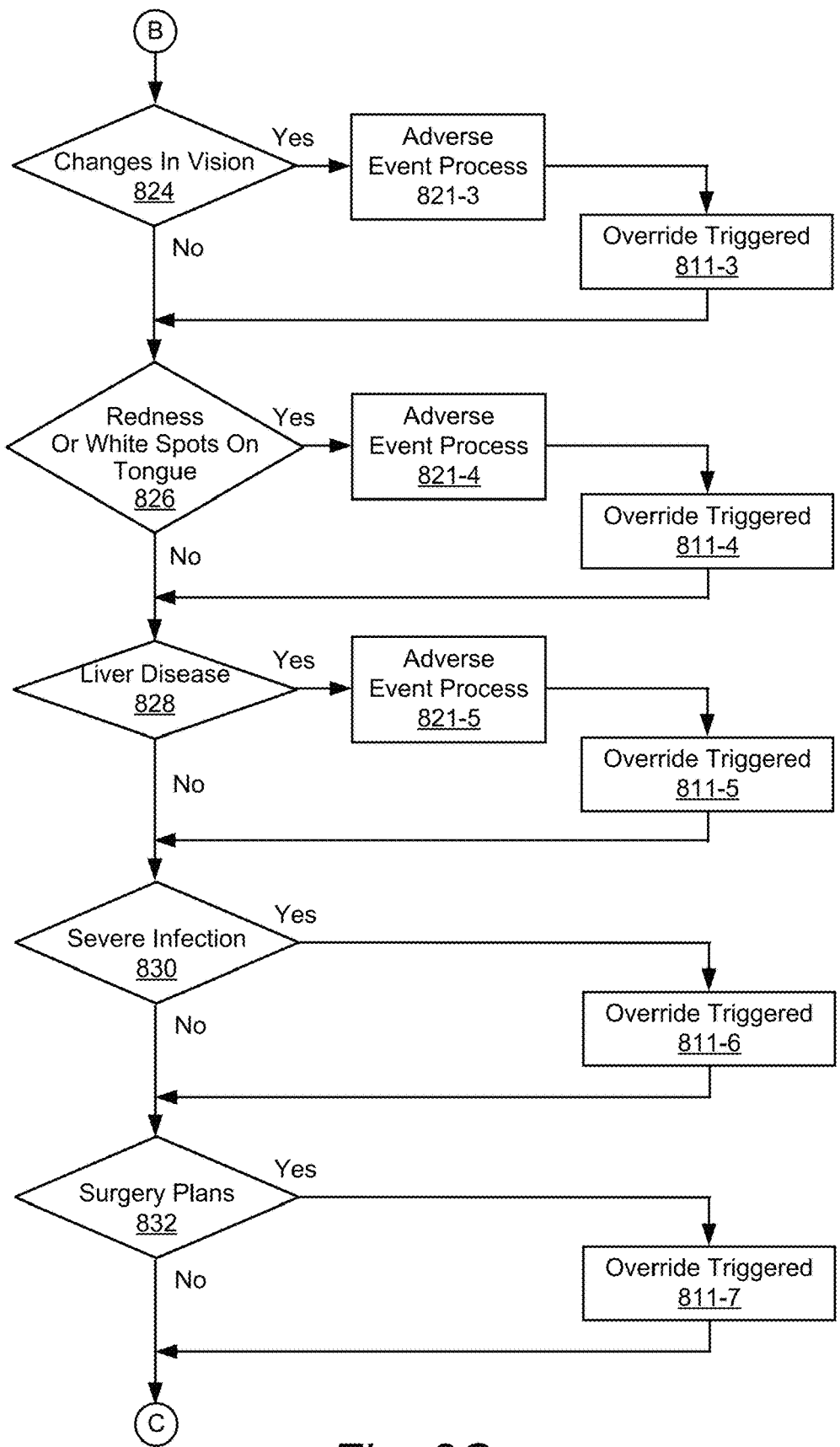
Figure 8D:
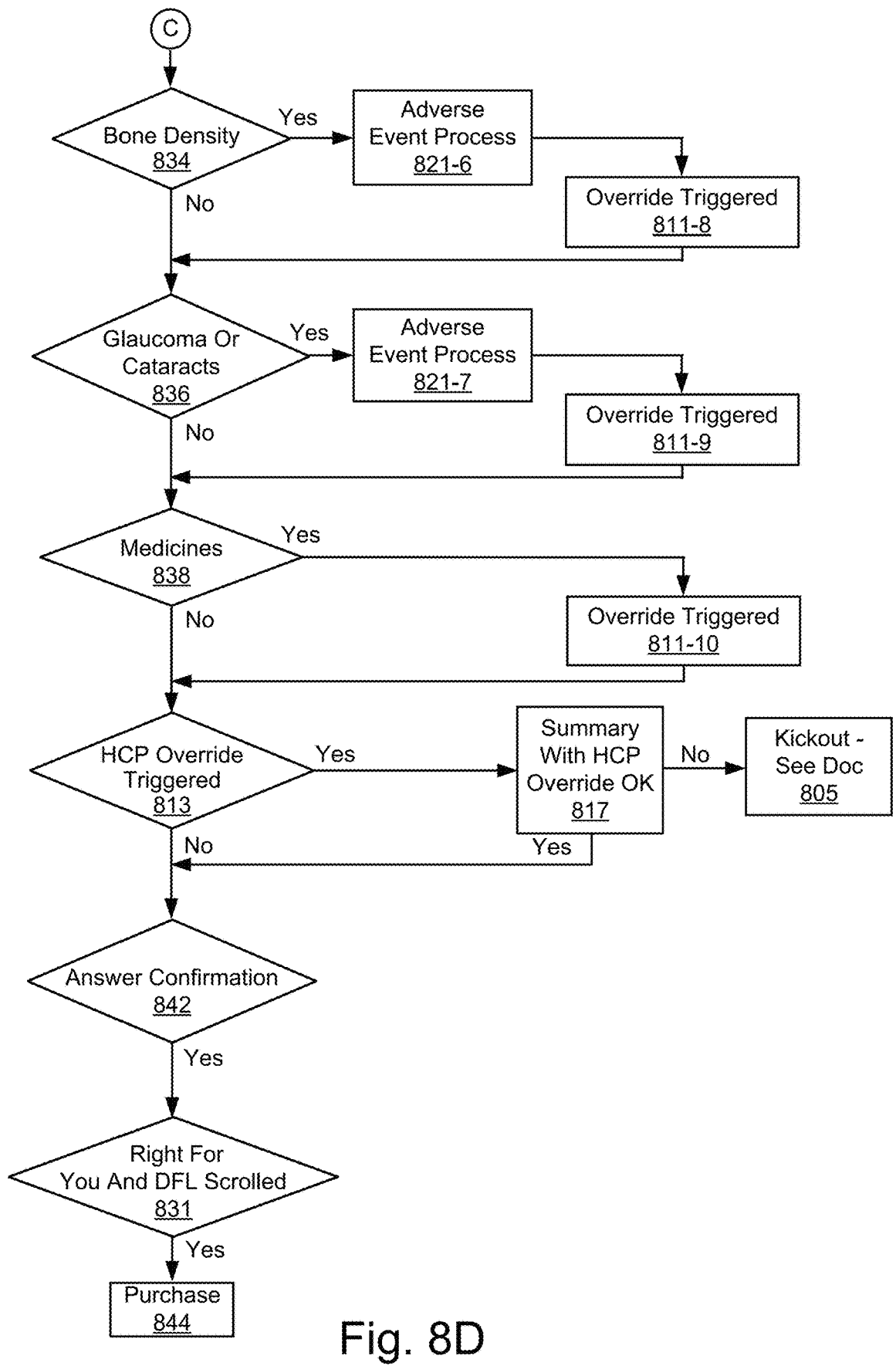

Referring to block 500 of FIG. 4H, the method also includes running all or a portion of the second survey results against a fourth plurality of filters of the second category class 220-2. When a respective filter in the fourth plurality of filters is fired, the subject is provided with a warning corresponding to the respective filter. In some embodiments, the warning is provided as a next step, e.g., prior to applying survey results to any subsequent filters, after the corresponding filter is fired. For example, with respect to FIGS. 8B and 8C, in some embodiments, e.g., when the infection filter is triggered at 822, the device would provide the subject with a warning prior to proceeding to the surgery filter at 824, e.g., requiring the subject confirm they have discussed their infection with a health care provider and the healthcare provider still recommends taking a corticosteroid pharmaceutical composition. In some embodiments the warning is provided after applying survey results to all subsequent filters. For example, with respect to FIGS. 8B, 8C, and 8E, in some embodiments, e.g., when the infection filter is triggered at 822, the device would proceed to the surgery filter at 824 prior to transmitting a warning to the subject, and then transmit all warnings corresponding to filters of the second category class, at 842, after survey results have been applied to all subsequent filters.

In some embodiments, the fourth plurality of filters of the second category class 220-2 includes some or all of the filters listed in Table 6. For example, in some embodiments, the fourth plurality of filters includes 2, 3, 4, 5, 6, 7, 8, 9, 10, or all 11 of the filters listed in Table 6. In some embodiments, the fourth plurality of filters of the second category class includes at least filters 1-4 and 6-9, as listed in Table 6.

TABLE 6

Example filters for risk factors associated with re-qualifying a subject for an over-the-counter provision of a corticosteroid pharmaceutical composition.

| Filter | Example Criteria |
|---|---|
| 1a | an infectious disease contact filter |
| 2a | a symptoms of infection filter |
| 3a | a vision deterioration filter |
| 4a | an oral health filter |
| 5a | a liver disease filter |
| 6a | an infection filter |
| 7a | a surgery filter |
| 8a | a bone density filter |
| 9a | an ocular disease filter |
| 10a | a drug interaction filter |
| 11a | a side effect filter |

It is contemplated that, in some embodiments, any one or more of the filters provided in Table 6 will not be included in the fourth plurality of filters. For example, in some embodiments, a characteristic associated with a particular survey result will be informative when qualifying a subject for one particular corticosteroid pharmaceutical composition but not for another corticosteroid pharmaceutical composition. Accordingly, it is contemplated that the fourth plurality of filters includes any sub-set of filters provided in Table 6. Likewise, the skilled artisan may know of other filters, not provided in Table 6, that may be combined with any subset of the filters 222 provided in Table 6 to form the fourth plurality of filters results used in the methods described herein.

Referring to block 502, in some embodiments, the fourth plurality of filters includes an infectious disease contact filter. The infectious disease contact filter is configured to be fired at least when the second plurality of survey results indicate that the subject has been in contact with someone having chicken pox, measles, or tuberculosis since receiving their last provision of the corticosteroid pharmaceutical composition. When the infectious disease contact filter is fired, the device transmits a warning corresponding to the infectious disease contact filter, and requires the user to acknowledge the warning before authorizing a provision of the corticosteroid pharmaceutical composition.

Referring to block 502, in some embodiments, the fourth plurality of filters includes a symptoms of infection filter. The symptoms of infection filter is configured to be fired at least when the second plurality of survey results indicates that the subject has experienced symptoms of an infection since receiving their last provision of the corticosteroid composition. In some embodiments, a symptom of infection, capable of firing the infection filter, includes fever, pain, aches, chills, tiredness, nausea, and/or vomiting. In some embodiments, a symptom of infection, capable of firing the infection filter, includes stomach area pain, diarrhea, loss of appetite, headaches, and/or weakness. When the symptoms of infection filter is fired, the device transmits a warning corresponding to the symptoms of infection filter, and requires the user to acknowledge the warning before authorizing a provision of the corticosteroid pharmaceutical composition.

Referring to block 502, in some embodiments, the fourth plurality of filters includes a vision deterioration filter. The vision deterioration filter is configured to be fired at least when the second plurality of survey results indicates that the subject has had vision deterioration since receiving their last provision of the corticosteroid pharmaceutical composition. In some embodiments, the second plurality of survey results indicates that the subject has had vision deterioration when the second plurality of survey results indicate that the subject has developed a symptom (e.g., a new and/or worsening symptom) of vision deterioration since receiving their last provision of the corticosteroid composition e.g., visual disturbances, ocular hyperemia, visual color distortions, eye pain, eye discomfort, photophobia, an increase in intraocular pressure, blurred vision, and/or conjunctivitis. When the vision deterioration filter is fired, the device transmits a warning corresponding to the vision deterioration filter, and requires the user to acknowledge the warning before authorizing a provision of the corticosteroid pharmaceutical composition.

Referring to block 502, in some embodiments, the fourth plurality of filters includes an oral health filter. In some embodiments, the oral health filter is configured to be fired at least when the second plurality of survey results indicates that the subject has experienced thrush since receiving their last provision of the corticosteroid pharmaceutical composition. In some embodiments, the oral health filter is configured to be fired at least when the second plurality of survey results indicates that the subject has experienced an oral fungal infection since receiving their last provision of the corticosteroid pharmaceutical composition. In some embodiments, the oral health filter is configured to be fired at least when the second plurality of survey results indicates that the subject has experienced a localized infection (e.g., *Candida albicans*, yeast infection, etc.) of the mouth and/or pharynx. In some embodiments, the second plurality of survey results indicate the subject has experienced an oral infection when the second plurality of survey results indicate the subject has developed redness or white-colored patches in their mouth or throat. When the oral health filter is fired, the device transmits a warning corresponding to the oral health filter, and requires the user to acknowledge the warning before authorizing a provision of the corticosteroid pharmaceutical composition.

Referring to block 502, in some embodiments, the fourth plurality of filters includes a liver disease filter. The liver disease filter is configured to be fired at least when the second plurality of survey results indicates that the subject has developed a liver problem since receiving their last provision of the corticosteroid pharmaceutical composition. In some embodiments, the second plurality of survey results indicates that the subject has developed a liver disease or a liver problem when the second plurality of survey results indicate that the subject has been diagnosed with a liver problem since receiving their last provision of the corticosteroid pharmaceutical composition. In some embodiments, the second plurality of survey results indicates that the subject has developed a liver disease or a liver problem when the second plurality of survey results indicate that the subject has developed a symptom (e.g., a new and/or worsening symptom) of a liver disease or a liver problem since receiving their last provision of the corticosteroid pharmaceutical composition, e.g., impaired hepatic function, acute liver failure, and cholestasis. In some embodiments, the liver disease filter is fired at least when the second plurality of survey results indicates that the subject has had a reduction in liver function since receiving their last provision of the corticosteroid pharmaceutical composition. When the liver disease filter is fired, the device transmits a warning corresponding to the liver disease filter, and requires the user to acknowledge the warning before authorizing a provision of the corticosteroid pharmaceutical composition.

Referring to block 508, in some embodiments, the fourth plurality of filters includes an infection filter, e.g., as described above in relation to the first survey. The infection filter is configured to be fired at least when the second plurality of survey results indicates that the subject is experiencing a severe, untreated infection. As previously described, infections include fungal infections, bacterial infections, viral infections, parasitic infections, and/or herpes simplex infection of the eye. When the infection filter is fired, the device transmits a warning corresponding to the infection filter, and requires the user to acknowledge the warning before authorizing a provision of the corticosteroid pharmaceutical composition.

In some embodiments, the fourth plurality of filters includes a single infection update filter, e.g., that encompasses both the symptoms of infection filter (e.g., that ensures the subject remains vigilant in watching for signs of an infection or changes in their immune system while taking the corticosteroid pharmaceutical composition) and the infection filter (e.g., that ensures that the subject has not developed specific types of severe infections), e.g., which is fired when the second plurality of survey results indicates that the subject has experienced symptoms of an infection or has developed a severe infection, since receiving their last provision of the corticosteroid pharmaceutical composition. For instance, in some embodiments, the fourth plurality of filters includes an infection update filter, an infectious disease contact filter, filter, a vision deterioration filter, an oral health filter, a surgery filter, a bone density filter, and an ocular disease filter.

Referring to block 502, in some embodiments, the fourth plurality of filters includes a surgery filter, e.g., as described above in relation to the first survey. The surgery filter is configured to be fired at least when the second plurality of survey results indicates that the subject is planning on undergoing surgery. In some embodiments, the surgery filter is configured to be fired at least when the second plurality of survey results indicates that the subject has undergone surgery since receiving their last provision of the corticosteroid pharmaceutical composition. As previously described, in some embodiments the surgery filter is configured to be fired at least when the second plurality of survey results indicates that the subject has experienced trauma, is adrenal insufficient, and/or has severe electrolyte loss. When the surgery filter is fired, the device transmits a warning corresponding to the surgery filter, and requires the user to acknowledge the warning before authorizing a provision of the corticosteroid pharmaceutical composition.

Referring to block 502, in some embodiments, the fourth plurality of filters includes a bone density filter, e.g., as described above in relation to the first survey. The bone density filter is configured to be fired at least when the second plurality of survey results indicates that the subject has experienced decreased bone density since receiving their last provision of the corticosteroid pharmaceutical composition. In some embodiments, the second plurality of survey results indicates that the subject has developed low bone mineral density when the second plurality of survey results indicate that the subject has been diagnosed with low bone mineral density since receiving their last provision of the corticosteroid composition. In some embodiments, the second plurality of survey results indicates that the subject has developed low bone mineral density when the second plurality of survey results indicate that the subject has developed a symptom (e.g., a new and/or worsening symptom) of low bone mineral density since receiving their last provision of the corticosteroid composition. When the bone density filter is fired, the device transmits a warning corresponding to the bone density filter, and requires the user to acknowledge the warning before authorizing a provision of the corticosteroid pharmaceutical composition.

Referring to block 502, in some embodiments, the fourth plurality of filters includes an ocular disease filter, e.g., as described above in relation to the first survey. The ocular disease filter is configured to be fired at least when the second plurality of survey results indicates that the subject has developed cataracts or glaucoma since receiving their last provision of the corticosteroid pharmaceutical composition. In some embodiments, the second plurality of survey results indicate that the subject has developed an ocular disease when the second plurality of survey results indicate that the subject has been diagnosed with an ocular disease since receiving their last provision of the corticosteroid composition. In some embodiments, the second plurality of survey results indicates that the subject has developed an ocular disease when the second plurality of survey results indicate that the subject has developed a symptom (e.g., a new and/or worsening symptom) of an ocular disease since receiving their last provision of the corticosteroid composition, e.g., increased intraocular pressure. When the ocular disease filter is fired, the device transmits a warning corresponding to the ocular disease filter, and requires the user to acknowledge the warning before authorizing a provision of the corticosteroid pharmaceutical composition.

Referring to block 502, in some embodiments, the fourth plurality of filters includes a drug interaction filter. The drug interaction filter is configured to be fired at least when the second plurality of survey results indicates that the subject has started taking a medication that interacts (e.g., a pharmacokinetic interaction and/or a pharmacodynamic interaction) with the corticosteroid pharmaceutical composition. In some embodiments, the drug interaction filter is fired when the second plurality of survey results indicates that the subject has started taking a medication selected from the group consisting of a corticosteroid medicine, an anticonvulsant, an immunosuppressant, ketoconazole, a medicine for the liver, and a prescription anti-retroviral. When the drug interaction filter is fired, the device transmits a warning corresponding to the drug interaction filter, and requires the user to acknowledge the warning before authorizing a provision of the corticosteroid pharmaceutical composition.

Referring to block 504, in some embodiments the second survey results further indicates whether the subject has experienced side effects associated with the corticosteroid pharmaceutical composition since receiving their last provision of the corticosteroid pharmaceutical composition. Accordingly, in some embodiments, the fourth plurality of filters further includes a side effect filter that is configured to be fired at least when the second survey results indicate that the subject has experienced side effects since receiving their last provision of the corticosteroid pharmaceutical composition. Side effects that are capable of triggering (e.g., triggering condition) the side effect filter include a sore throat, a sore nose, nausea, hay fever, an upper respiratory tract viral infection, gastroenteritis, and an ear infection. In some embodiments, side effects that are capable of triggering the side effect filter include viral irritation of the stomach, viral irritation of the intestine, inflammation of the stomach, inflammation of the intestine, stomach area pain, diarrhea, vomiting, loss of appetite, headaches, and weakness. In some embodiments, side effects that are capable of triggering the side effect filter include paradoxical bronchospasm, urticarial, flushing, allergic dermatitis, hypercorticism, adrenal suppression, nasopharyngitis, and a reduction in bone mineral density. In some embodiments, a side effect that is capable of triggering the side effect filter is a decrease in growth velocity of the subject. In some embodiments, side effects that are capable of triggering the side effect filter include pruritus, dyspnea, angioedema, and an anaphylactic reaction. In some embodiments, side effects that are capable of triggering the side effect filter include swelling of the lips, swelling of the tongue, and swelling of the pharynx. In some embodiments, a side effect that is capable of triggering the side effect filter is urticaria, eosinophilia, vasculitis rash, rhinitis, rhinorrhea, nasal sinus disorders, laryngitis, adverse dental symptoms such as tooth decay, tooth pain, and yellowing of the teeth, and worsening pulmonary symptoms.

Referring to block 506, in some embodiments when a respective filter in the third plurality of filters or fourth plurality of filters is fired, a record associated with the firing of the respective filter is stored (e.g., memorializing an adverse event that is required to be reported to a regulatory agency). This record is stored in an adverse event module 242 which includes records of filter firing events associated with a plurality of subjects (e.g., an aggregation of adverse events associated with the corticosteroid pharmaceutical composition across a population of subjects taking the corticosteroid pharmaceutical composition over-the-counter). In some embodiments, an indication of the adverse event is communicated to a third party (e.g., a medical practitioner associated with the subject, a health care provider of the subject, a manufacturer/promoter of the corticosteroid pharmaceutical composition, and/or a regulatory agency). In some embodiments, the indication is automatically stored in the adverse event module 242 when a response submitted by a subject, as part of the second survey, triggers a filter associated with an adverse event.

Figure 4I:
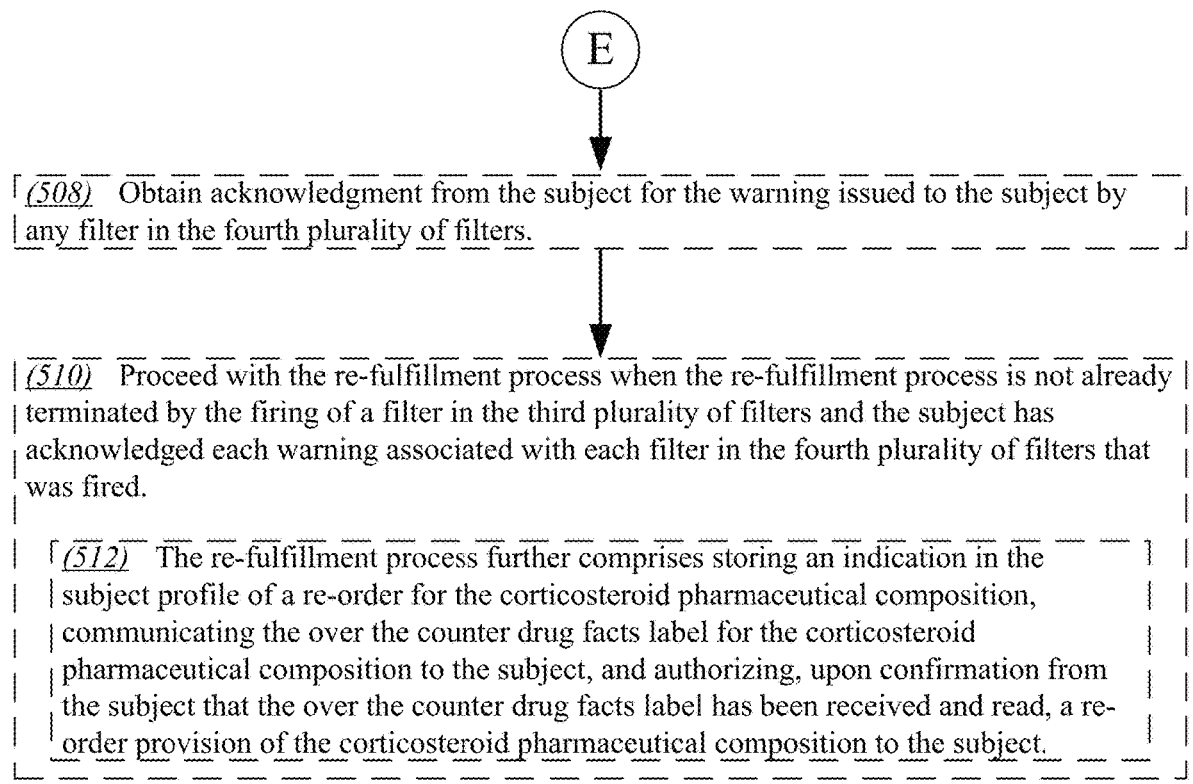
Figures 5A, 5B:

Referring to block 508 of FIG. 4I, in some embodiments the method also includes obtaining acknowledgment from the subject for each warning issued to the subject by any filter in the fourth plurality of filters. As described with respect to the warnings issued in conjunction with the second plurality of filters of the second category class, in some embodiments, the warning includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a corticosteroid pharmaceutical composition in view of the underlying risk factor. Accordingly, acknowledgement is obtained from the subject when the subject indicates that they have discussed the risk factor underlying the respective filter in the fourth plurality of filters that was fired with a health care provider.

Referring to block 510, in some embodiments the procedure further includes proceeding with the re-fulfillment process when the re-fulfillment process is not already terminated by the firing of a filter in the third plurality of filters. In order for completion of the re-fulfillment process, the subject is required to acknowledge each warning associated with each filter 222 in the fourth plurality of filters that was fired.

Referring to block 512, in some embodiments the re-fulfillment process also includes storing a record in the user profile 234 of the subject of a re-order 238 for the corticosteroid pharmaceutical composition.

The re-fulfillment process further includes communicating an over-the-counter drug facts label 230 for the corticosteroid pharmaceutical composition to the subject. As previously described, communication of the over-the-counter drug facts label 230 can occur in a variety of means. Upon confirmation from the subject that the over-the-counter drug facts label 230 has been received and read, the method includes authorizing a re-order provision of the corticosteroid pharmaceutical composition to the subject. In some embodiments, this re-order provision includes the destination of the subject.

FIG. 7 illustrates an example method (700) (e.g., performed at an electric device 102 or 250) for qualifying a subject for an over-the-counter corticosteroid pharmaceutical composition (e.g., containing budesonide, mometasone furoate, or fluticasone furoate). In some embodiments, the method of FIG. 7 is utilized when the subject has not been previously qualified for the corticosteroid pharmaceutical composition. In some embodiments, the method of FIG. 7 is utilized when the subject was previously qualified for the corticosteroid composition but a predetermined period of time elapsed since the previous qualification occurred (e.g., the most recent qualification/re-qualification of the subject was greater than one year ago).

Referring to FIG. 7, the device prompts (702) the user to confirm that they know their FEV1 levels and other relevant medical information (e.g., because the subject must know their FEV1 level in order to complete the qualification process). If the subject indicates they do not know their FEV1 value, the process terminates 701 without authorizing provision of the corticosteroid pharmaceutical agent, and optionally transmits advice to the user to return later, e.g., once they know their FEV1 level. If the subject indicates they know their FEV1 level, the process continues.

Once the subject has acknowledged they have the requisite information for continuing the device prompts (704) the subject to acknowledge a privacy notice. Since the present disclosure requires the subject to know and input sensitive medical information (e.g., information only the subject and a medical practitioner have access to), privacy of this information is important. Once the subject has acknowledged they have the requisite privacy for continuing, the device proceeds with the qualification process.

The device prompts the subject to provide information indicating their dairy allergy status and then applies (706) the answer received from the subject to a first allergy filter. When the first allergy filter is fired (e.g., when the answer indicates the subject is allergic to milk protein), the device terminates (703) the qualification process without authorizing provision of the corticosteroid pharmaceutical agent and, optionally, transmits advice to the user as to why they should not take the corticosteroid pharmaceutical agent.

When the first allergy filter is not fired, the device proceeds with the qualification process, prompting the subject to provide information indicating their use of steroid medications and then applies (708) the answer received from the subject to a steroid medication filter. When the steroid medication filter is fired (e.g., when the answer indicates the subject is already taking a steroid medication), the device terminates (703) the qualification process without authorizing provision of the corticosteroid pharmaceutical agent and, optionally, transmits advice to the user as to why they should not take the corticosteroid pharmaceutical agent and/or to return once they have ceased taking a steroid medication for a predetermined period of time.

When the steroid medication filter is not fired, the device proceeds with the qualification process, prompting to provide information indicating an age of the subject and then applies (710) the answer received from the subject to an age filter. When the age filter is fired (e.g., when the answer indicates the subject is younger than eighteen years old), the device terminates (703) the qualification process without authorizing provision of the corticosteroid pharmaceutical agent and, optionally, transmits advice to the user as to why they should not take the corticosteroid pharmaceutical agent and/or to return once they have reach an age that is appropriate to take the corticosteroid pharmaceutical agent.

When the age filter is not fired, the device proceeds with the qualification process, prompting the subject to provide information indicating pulmonary function status and then applies (712) the answer received from the subject to a pulmonary function filter. When the pulmonary function filter is fired (e.g., when the answer indicates the subject has severely compromised pulmonary function, e.g., less than 80% of expected function), the device terminates (703,705) the qualification process without authorizing provision of the corticosteroid pharmaceutical agent and, optionally, transmits advice to the user as to why they should not take the corticosteroid pharmaceutical agent and/or to seek advice from a medical professional.

When the pulmonary function filter is not fired, the device proceeds with the qualification process, prompting the subject to provide information indicating how frequently the subject experiences symptoms of asthma and then applies (714) the answer received from the subject to an asthma severity sub-filter. When the asthma severity sub-filter stimulator filter is fired (e.g., when the answer indicates the subject experiences symptoms of asthma less than twice a week or more than six times a week), the device terminates (703) the qualification process without authorizing provision of the corticosteroid pharmaceutical agent and, optionally, transmits advice to the user as to why they should not take the corticosteroid pharmaceutical agent.

When the asthma severity sub-filter is not fired, the device proceeds with the qualification process, prompting the subject to provide information indicating how frequently symptoms of asthma disrupt the subject's sleep and then applies (716) the answer received from the subject to an asthma severity sub-filter. When the asthma severity sub-filter is fired (e.g., when the answer indicates the symptoms of asthma disrupt the subject's sleep less than thrice a month or more than four a month), the device terminates (703) the qualification process without authorizing provision of the corticosteroid pharmaceutical agent and, optionally, transmits advice to the user as to why they should not take the corticosteroid pharmaceutical agent.

When the asthma severity sub-filter is not fired, the device proceeds with the qualification process, prompting the subject to provide information indicating how frequently the subject uses a rescue inhaler and then applies (718) the answer received from the subject to an asthma severity sub-filter. When the asthma severity sub-filter is fired (e.g., when the answer indicates the subject uses a rescue inhaler less than twice a week or more than six times a week), the device terminates (703) the qualification process without authorizing provision of the corticosteroid pharmaceutical agent and, optionally, transmits advice to the user as to why they should not take the corticosteroid pharmaceutical agent.

When the asthma severity sub-filter is not fired, the device proceeds with the qualification process, prompting the subject to provide information indicating how frequently the subject uses oral steroids and then applies (720) the answer received from the subject to an asthma severity sub-filter. When the asthma severity sub-filter is fired (e.g., when the answer indicates the subject uses oral steroids more than once a year), the device terminates (703) the qualification process without authorizing provision of the corticosteroid pharmaceutical agent and, optionally, transmits advice to the user as to why they should not take the corticosteroid pharmaceutical agent.

When the first asthma filter is not fired, the device proceeds with the qualification process, prompting the subject to provide information indicating whether the subject has a liver problem and then applies (722) the answer received from the subject to a liver disease filter. When the liver disease filter is fired (e.g., when the answer indicates the subject has a liver problem), an override procedure (711-1) is initiated (e.g., the device creates a record indicating that the user must confirm they have discussed taking a corticosteroid pharmaceutical composition with a health care professional, e.g., in light of the underlying risk factor).

The device proceeds with the qualification process, prompting the subject to provide information indicating an infection status of the subject and then applies (724) the answer received from the subject to an infection filter. When the liver infection filter is fired (e.g., when the answer indicates the subject has an untreated infection), an override procedure (711-2) is initiated (e.g., the device creates a record indicating that the user must confirm they have discussed taking a corticosteroid pharmaceutical composition with a health care professional, e.g., in light of the underlying risk factor).

The device proceeds with the qualification process, prompting the subject to provide information indicating a surgery status of the subject and then applies (726) the answer received from the subject to a surgery filter. When the surgery filter is fired (e.g., when the answer indicates the subject has just had or is planning on having surgery), an override procedure (711-3) is initiated (e.g., the device creates a record indicating that the user must confirm they have discussed taking a corticosteroid pharmaceutical composition with a health care professional, e.g., in light of the underlying risk factor).

The device proceeds with the qualification process, prompting the subject to provide information indicating a bone density status of the subject and then applies (728) the answer received from the subject to a bone density filter. When the bone density filter is fired (e.g., when the answer indicates the subject has reduced bone density), an override procedure (711-4) is initiated (e.g., the device creates a record indicating that the user must confirm they have discussed taking a corticosteroid pharmaceutical composition with a health care professional, e.g., in light of the underlying risk factor).

The device proceeds with the qualification process, prompting the subject to provide information indicating whether the subject has ever had cataracts or glaucoma and then applies (730) the answer received from the subject to an ocular disease filter. When the ocular disease filter is fired (e.g., when the answer indicates the subject has had cataracts or glaucoma), an override procedure (711-5) is initiated (e.g., the device creates a record indicating that the user must confirm they have discussed taking a corticosteroid pharmaceutical composition with a health care professional, e.g., in light of the underlying risk factor).

The device proceeds with the qualification process, prompting the subject to provide information indicating whether the subject is taking a medication that interacts with the corticosteroid pharmaceutical composition and then applies (732) the answer received from the subject to a drug interaction filter. When the drug interaction filter is fired (e.g., when the answer indicates the subject is taking a medication that interacts with the corticosteroid pharmaceutical composition), an override procedure (711-6) is initiated (e.g., the device creates a record indicating that the user must confirm they have discussed taking a corticosteroid pharmaceutical composition with a health care professional, e.g., in light of the underlying risk factor).

The device proceeds with the qualification process, determining (713) whether the override procedure has been triggered (e.g., by firing of any one of the liver disease filter, the infection filter, the surgery filter, the bone density filter, the ocular disease filter, or the drug interaction filter). If the override procedure has been triggered, the device prompts (717) the user to confirm that they have spoken with a medical professional about taking a corticosteroid pharmaceutical composition (e.g., in view of the underlying risk factor that triggered liver disease filter, the infection filter, the surgery filter, the bone density filter, the ocular disease filter, or the drug interaction filter) and the medical professional recommended taking the corticosteroid pharmaceutical composition. If the user's responses indicate they have not spoken with a medical professional or the medical professional did not recommend taking the corticosteroid pharmaceutical composition, the device terminates (705) the process and, optionally, transmits advice for the subject to consult a medical professional.

If the override procedure was not triggered, or the override procedure was triggered and the subject's response (717) indicated that they spoke with a medical professional, e.g., who recommended they take a corticosteroid pharmaceutical composition (e.g., in view of the underlying risk factor triggering the override procedure), the device proceeds with the qualification process, prompting (736) the subject to confirm their answers. If the user confirms their answers, the device transmits (738) a drug facts label for the corticosteroid pharmaceutical composition and prompts the user to read the drug facts label. If the subject confirms they have read the drug facts label, the device proceeds to authorize (740) purchase of the corticosteroid pharmaceutical composition.

FIG. 8 illustrates an example method for qualifying a subject for a refill of an over-the-counter corticosteroid pharmaceutical composition (e.g., following a prescription from a medical professional or initial qualification by a method described herein). Referring to FIG. 8, the device prompts (802,804) the subject to acknowledge a privacy notice and confirm that the subject knows their relevant medical information (e.g., the subject knows their FEV1 level). When the user indicates they do not know their FEV1 level, the device terminates (801) the process without authorizing provision of the corticosteroid pharmaceutical agent, optionally transmitting advice for the user to return once they know their FEV1 level. In some embodiments, e.g., where the user has recently begun taking the corticosteroid pharmaceutical compound and/or the device has access to a recent a FEV1 measurement from the subject, the device bypasses prompting the user to confirm that they know their FEV1 levels.

Once the subject has acknowledged they have the requisite privacy for continuing, the device proceeds with the process, prompting the user to provide information indicating their dairy allergy status and applies (806) the answer received from the subject to a dairy allergy filter. When the dairy allergy filter is fired (e.g., when the answer indicates the subject has developed a milk protein allergy), the device creates (821) a record of an adverse event (e.g., aggregated in an adverse event data store having records of adverse events from a plurality of users) and the device terminates (803) the qualification process, optionally transmitting advice to the subject as to why they should not take the corticosteroid pharmaceutical agent.

When the dairy allergy filter is not fired, the device proceeds with the qualification process, prompting the subject to provide information indicating whether the subject has started to take another steroid medication and then applies (808) the answer received from the subject to a steroid medication filter. When the steroid medication filter is fired (e.g., when the answer indicates that the subject is taking another steroid composition), the device terminates (803) the qualification process without authorizing provision of the corticosteroid pharmaceutical agent and, optionally, transmits advice to the user as to why they should not take the corticosteroid pharmaceutical agent.

When the steroid medication filter is not fired, the device proceeds with the qualification process, prompting the subject to provide information indicating a pulmonary function status and then applies (810) the answer received from the subject to a pulmonary function filter. When the pulmonary function filter is fired (e.g., when the answer indicates the subject has compromised pulmonary function), the device terminates (803,805) the qualification process without authorizing provision of the corticosteroid pharmaceutical agent and, optionally, transmits advice to the subject as to why they should not take the corticosteroid pharmaceutical composition and/or to discuss taking a corticosteroid with a medical professional.

When the pulmonary function filter is not fired, the device proceeds with the qualification process, prompting the subject to provide information indicating how frequently the subject experiences symptoms of asthma and then applies (812) the answer received from the subject to an asthma reduction sub-filter. When the asthma reduction sub-filter is fired (e.g., when the answer indicates the subject experiences symptoms of asthma more than twice a week), the device terminates (805) the qualification process authorizing provision of the corticosteroid pharmaceutical agent and, optionally, transmits advice to the subject as to why they should not take the corticosteroid pharmaceutical composition and/or to discuss taking a pharmaceutical corticosteroid with a medical professional.

When the asthma reduction sub-filter is not fired, the device proceeds with the qualification process, prompting the subject to provide information indicating how frequently symptoms of asthma disrupt the subject's sleep and then applies (814) the answer received from the subject to an asthma reduction sub-filter. When the asthma reduction sub-filter is fired (e.g., when the answer indicates symptoms of asthma disrupt the subject's sleep more than twice a month), the device terminates (803) the qualification process authorizing provision of the corticosteroid pharmaceutical agent and, optionally, transmits advice to the subject as to why they should not take the corticosteroid pharmaceutical agent and/or to discuss taking a corticosteroid with a medical professional.

When the asthma reduction sub-filter is not fired, the device proceeds with the qualification process, prompting the subject to provide information indicating how frequently the subject uses a rescue inhaler and then applies (816) the answer received from the subject to an asthma reduction sub-filter. When the asthma reduction sub-filter is fired (e.g., when the answer indicates the subject uses a rescue inhaler more than twice a week), the device terminates (803) the qualification process authorizing provision of the corticosteroid pharmaceutical agent and, optionally, transmits advice to the subject as to why they should not take the corticosteroid pharmaceutical agent and/or to discuss taking a corticosteroid with a medical professional.

When the asthma reduction sub-filter is not fired, the device proceeds with the qualification process, prompting the subject to provide information indicating how frequently the subject uses oral steroids and then applies (818) the answer received from the subject to an asthma reduction sub-filter. When the asthma reduction sub-filter is fired (e.g., when the answer indicates the subject uses oral steroids more than once a year), the device terminates (803) the qualification process authorizing provision of the corticosteroid pharmaceutical agent and, optionally, transmits advice to the subject as to why they should not take the corticosteroid pharmaceutical agent and/or to discuss taking a corticosteroid with a medical professional.

When the asthma reduction sub-filter is not fired, the device proceeds with the qualification process, prompting the subject to provide information indicating whether the subject has or has been in contact with someone having chicken pox, measles, or tuberculosis since receiving their last provision of the corticosteroid pharmaceutical composition and then applies (820) the answer received from the subject to an infectious disease contact filter. When the infectious disease contact filter is fired (e.g., when the answer indicates the subject has been in contact with someone having chicken pox, measles, or tuberculosis since receiving their last provision of the corticosteroid pharmaceutical composition), an override procedure (811-1) is initiated (e.g., the device creates a record indicating that the user must confirm they have discussed taking a corticosteroid pharmaceutical composition with a health care professional, e.g., in view of the underlying risk factor).

The device then proceeds with the qualification process, prompting the subject to provide information indicating whether the subject has experienced a symptom of infection since receiving their last provision of the corticosteroid pharmaceutical composition and then applies (822) the answer received from the subject to a symptoms of infection filter. When the symptoms of infection filter is fired (e.g., when the answer indicates the subject has experienced a symptom of infection), the device creates (821-2) a record of an adverse event (e.g., aggregated in an adverse event data store having records of adverse events from a plurality of users) and initiates (811-2) an override procedure (e.g., creates a record indicating that the user must confirm they have discussed taking a corticosteroid pharmaceutical composition with a health care professional).

The device proceeds with the qualification process, prompting the subject to provide information indicating whether they have experienced deterioration in vision and then applies (824) the answer received from the subject to a vision deterioration filter. When the vision deterioration filter is fired (e.g., when the answer indicates the subject has experiences loss in vision), the device creates (821-3) a record of an adverse event (e.g., aggregated in an adverse event data store having records of adverse events from a plurality of users) and initiates (811-3) an override procedure (e.g., creates a record indicating that the user must confirm they have discussed taking a corticosteroid pharmaceutical composition with a health care professional).

The device proceeds with the qualification process, prompting the subject to provide information indicating an oral health status of the subject and then applies (826) the answer received from the subject to an oral health filter. When the oral health filter is fired (e.g., when the answer indicates the subject has experienced thrush), the device creates (821-4) a record of an adverse event (e.g., aggregated in an adverse event data store having records of adverse events from a plurality of users) and initiates (811-4) an override procedure (e.g., creates a record indicating that the user must confirm they have discussed taking a corticosteroid pharmaceutical composition with a health care professional).

The device proceeds with the qualification process, prompting the subject to provide information indicating whether the subject has developed a liver problem since receiving their last provision of the corticosteroid composition and then applies (828) the answer received from the subject to a liver disease filter. When the liver disease filter is fired (e.g., when the answer indicates the subject has developed a liver problem), the device creates (821-5) a record of an adverse event (e.g., aggregated in an adverse event data store having records of adverse events from a plurality of users) and initiates (811-5) an override procedure (e.g., creates a record indicating that the user must confirm they have discussed taking a corticosteroid pharmaceutical composition with a health care professional).

The device proceeds with the qualification process, prompting the subject to provide information indicating whether the subject has an untreated infection and then applies (830) the answer received from the subject to an infection filter. When the infection filter is fired (e.g., when the answer indicates the subject has an untreated infection), the device initiates (811-6) an override procedure (e.g., creates a record indicating that the user must confirm they have discussed taking a corticosteroid pharmaceutical composition with a health care professional).

The device proceeds with the qualification process, prompting the subject to provide information indicating a surgery status of the subject and then applies (832) the answer received from the subject to a surgery filter. When the surgery filter is fired (e.g., when the answer indicates the subject has recently had or is planning to have surgery), the device initiates (811-7) an override procedure (e.g., creates a record indicating that the user must confirm they have discussed taking a corticosteroid pharmaceutical composition with a health care professional).

The device proceeds with the qualification process, prompting the subject to provide information indicating whether they have developed reduced bone density and then applies (834) the answer received from the subject to a bone density filter. When the bone density filter is fired (e.g., when the answer indicates the subject has developed reduced bone mineral density since receiving their last provision of the corticosteroid pharmaceutical composition), the device creates (821-6) a record of an adverse event (e.g., aggregated in an adverse event data store having records of adverse events from a plurality of users) and initiates (811-8) an override procedure (e.g., creates a record indicating that the user must confirm they have discussed taking a corticosteroid pharmaceutical composition with a health care professional).

The device proceeds with the qualification process, prompting the subject to provide information indicating whether they have developed cataracts or glaucoma and then applies (836) the answer received from the subject to an ocular disease filter. When the ocular disease filter is fired (e.g., when the answer indicates the subject has developed cataracts or glaucoma since receiving their last provision of the corticosteroid pharmaceutical composition), the device creates (821-7) a record of an adverse event (e.g., aggregated in an adverse event data store having records of adverse events from a plurality of users) and initiates (811-9) an override procedure (e.g., creates a record indicating that the user must confirm they have discussed taking a corticosteroid pharmaceutical composition with a health care professional).

The device proceeds with the qualification process, prompting the subject to provide information indicating whether they have begun taking a medication that interacts with the corticosteroid pharmaceutical composition and then applies (838) the answer received from the subject to a drug interaction filter. When the drug interaction filter is fired (e.g., when the answer indicates the subject has started taking a medication that interacts with the corticosteroid pharmaceutical composition), the device initiates (811-10) an override procedure (e.g., creates a record indicating that the user must confirm they have discussed taking a corticosteroid pharmaceutical composition with a health care professional).

The device proceeds with the qualification process, determining (813) whether the override procedure has been triggered (e.g., by firing of any one of the liver disease filter, the infection filter, the surgery filter, the bone density filter, the ocular disease filter, or the drug interaction filter). If the override procedure has been triggered, the device prompts (817) the user to confirm that they have spoken with a medical professional about taking a corticosteroid pharmaceutical composition (e.g., in view of the underlying risk factor that triggered liver disease filter, the infection filter, the surgery filter, the bone density filter, the ocular disease filter, or the drug interaction filter) and the medical professional recommended taking the corticosteroid pharmaceutical composition. If the user's responses indicate they have not spoken with a medical professional or the medical professional did not recommend taking the corticosteroid pharmaceutical composition, the device terminates (805) the process and, optionally, transmits advice for the subject to consult a medical professional.

If the override procedure was not triggered, or the override procedure was triggered and the subject's response (817) indicated that they spoke with a medical professional, e.g., who recommended they take a corticosteroid pharmaceutical composition (e.g., in view of the underlying risk factor triggering the override procedure), the device proceeds with the qualification process, prompting (842) the subject to confirm their answers. If the user confirms their answers, the device transmits (831) a drug facts label for the corticosteroid pharmaceutical composition and prompts the user to read the drug facts label. If the subject confirms they have read the drug facts label, the device proceeds to authorize (844) purchase of the corticosteroid pharmaceutical composition.

SPECIFIC EMBODIMENTS

In one aspect, the disclosure provides methods, software, and computer systems for qualifying a human subject for over-the-counter delivery of a corticosteroid pharmaceutical composition for treating or preventing symptoms of asthma. In one embodiment, a computer system (e.g., computer system 250 in FIG. 2) includes instructions for conducting a survey of the subject (e.g., including survey questions 208 and 212 administered via assessment module 252 in FIG. 2) to obtain information about the subject necessary to run against at least two series of filters (e.g., filters 216 and 222 in first filter category class 214-1 and second filter category class 220-2, respectively, in FIG. 2). The computer system also includes instructions for running the survey results against the filters. Filters 216 in the first series of filters 214 prevent authorization of a provision of the OTC corticosteroid where the subject's survey results identify a contraindication for the OTC corticosteroid. Filters 222 in the second series of filters 220 generate a warning 226 where the subject's survey results identify a risk factor for the OTC corticosteroid. In some embodiments, the warning 226 includes a prompt requiring the subject to confirm they have discussed the risk factor with a physician in order to proceed with qualification for the OTC corticosteroid.

In one aspect, the disclosure provides methods, software, and computer systems for re-qualifying a human subject for over-the-counter delivery of a corticosteroid pharmaceutical composition for treating or preventing symptoms of asthma. In one embodiment, a computer system (e.g., computer system 250 in FIG. 2) includes instructions for conducting a survey of the subject (e.g., administered via reassessment module 254 in FIG. 2) to obtain information about the subject necessary to run against at least two series of filters. The computer system also includes instructions for running the survey results against the filters. Filters 216 in the third series of filters prevent authorization for delivery of the OTC corticosteroid where the subject's survey results identify a contraindication for the OTC corticosteroid. Filters 222 in the fourth series of filters generate a warning 226 where the subject's survey results identify a risk factor for the OTC corticosteroid. In some embodiments, the warning 226 includes a prompt requiring the subject to confirm they have discussed the risk factor with a physician in order to proceed with qualification for the OTC corticosteroid.

In one aspect, the disclosure provides a computer system for qualifying a human subject for over-the-counter delivery of a corticosteroid pharmaceutical composition to treat or prevent symptoms of asthma. The computer system comprising one or more processors and a memory, the memory comprising non-transitory instructions which, when executed by the one or more processor, perform a method for qualifying a human subject for over-the-counter delivery of the corticosteroid pharmaceutical composition. The method includes conducting a first survey of the subject thereby obtaining a first plurality of survey results necessary to run against a first plurality of filters of a first category class and a second plurality of filters of a second category class. The method also includes running all or a portion of the first plurality of survey results against a first plurality of filters of a first category class, wherein, when a respective filter in the first plurality of filters is fired, the subject is deemed not qualified for delivery of the corticosteroid pharmaceutical composition and the method is terminated without delivery of the corticosteroid pharmaceutical composition to the subject. The method also includes running all or a portion of the first plurality of survey results against a second plurality of filters of a second category class, wherein, when a respective filter in the second plurality of filters is fired, the subject is provided with a warning corresponding to the respective filter. The method also includes obtaining acknowledgment from the subject for the warning issued to the subject by any filter in the second plurality of filters. The method also includes proceeding with a fulfillment process when no filter in the first plurality of filters has been fired and the subject has acknowledged each warning associated with each filter in the second plurality of filters that was fired. The fulfillment process includes: storing an indication in a subject profile of an initial order for the corticosteroid pharmaceutical composition, communicating an over-the-counter drug facts label for the corticosteroid pharmaceutical composition to the subject, and authorizing, upon confirmation from the subject that the over-the-counter drug facts label has been received and read, provision of the corticosteroid pharmaceutical composition to the subject. In some embodiments, the authorization includes a destination associated with the subject.

In some embodiments, the first plurality of survey results includes, or at least indicate, a plurality of survey results selected from the survey results listed in Table 1. In one embodiment, the first plurality of survey results indicates: whether the subject is already taking a steroid medication, an age of the subject, a pulmonary function status of the subject, an asthma severity of the subject, whether the subject has an untreated infection, a surgery status of the subject, a bone density status of the subject, and whether the subject has ever had cataracts or glaucoma.

In some embodiments, the first plurality of filters includes a plurality of filters selected from the filters listed in Table 2. In one embodiment, the first plurality of filters includes a steroid medication filter, an age filter, a pulmonary function filter, and an asthma severity filter.

In some embodiments, the second plurality of filters includes a plurality of filters selected from the filters listed in Table 3. In one embodiment, the second plurality of filters includes an infection filter, a surgery filter, a bone density filter, and an ocular disease filter.

In some embodiments, the first and second plurality of filters includes filters selected from the filters listed in Table 7. In some embodiments, the first plurality of filters of the first category class include a first sub-plurality of the filters listed in Table 7, for example, 2, 3, 4, 5, 6, 7, 8, 9, or 10 of the filters listed in Table 7, and the second plurality of filters of the first category class include a second sub-plurality of the filters listed in Table 7, which is different from the first sub-plurality of filters, for example, 2, 3, 4, 5, 6, 7, 8, 9, or 10 of the filters listed in Table 7. In some embodiments, each of the filters in the first sub-plurality of filters is different from each of the filters in the second sub-plurality of filters (e.g., no filter listed in Table 7 is included in both the first sub-plurality and the second sub-plurality of filters). In some embodiments, a system for qualifying a subject for delivery of an over-the-counter corticosteroid pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 7, e.g., at least 2, 3, 4, 5, 6, 7, 8, 9, or all 12 of the filters listed in Table 7. In some embodiments, where a filter listed in Table 7 corresponds to a filter listed in Table 2 or Table 3, a threshold level sufficient to fire the corresponding filter listed in Table 2 or Table 3, as described in detail above, is sufficient to fire the filter listed in Table 7.

TABLE 7

Example filters for qualifying a subject for an over-the-counter provision of a corticosteroid pharmaceutical composition.

| Filter | Example Criteria |
| --- | --- |
| 1b | a dairy allergy filter |
| 2b | a steroid medication filter |
| 3b | an age filter |
| 4b | a pulmonary function filter |
| 5b | an asthma severity filter |
| 6b | a liver disease filter |
| 7b | an infection filter |
| 8b | a surgery filter |
| 9b | a bone density filter |
| 10b | an ocular disease filter |
| 11b | a drug interaction filter |
| 12b | an adverse reaction filter |

In one aspect, the disclosure provides methods, software, and computer systems for qualifying a human subject for a re-order of an over-the-counter provision of a corticosteroid pharmaceutical composition to treat or prevent symptoms of asthma. In one embodiment, a computer system includes instructions, responsive to receiving a re-order request from the subject for the corticosteroid pharmaceutical composition, for performing a re-fulfillment procedure comprising conducting a second survey of the subject thereby obtaining a second plurality of survey results necessary to run against a third plurality of filters of a first category class and a fourth plurality of filters of a second category class. The method also includes running all or a portion of the second plurality of survey results against a third plurality of filters of a first category class, wherein, when a respective filter in the third plurality of filters is fired, the subject is deemed not qualified for delivery of the corticosteroid pharmaceutical composition and the method is terminated without delivery of the corticosteroid pharmaceutical composition to the subject. The method also includes running all or a portion of the second plurality of survey results against a fourth plurality of filters of a second category class, wherein, when a respective filter in the fourth plurality of filters is fired, the subject is provided with a warning corresponding to the respective filter. The method also includes obtaining acknowledgment from the subject for the warning issued to the subject by any filter in the fourth plurality of filters. The method also includes proceeding with a re-fulfillment process when no filter in the third plurality of filters has been fired and the subject has acknowledged each warning associated with each filter in the fourth plurality of filters that was fired. The re-fulfillment process includes: storing an indication in a subject profile of a re-order for the corticosteroid pharmaceutical composition, communicating the over-the-counter drug facts label for corticosteroid pharmaceutical composition to the subject, and authorizing, upon confirmation from the subject that the over-the-counter drug facts label has been received and read, provision of the corticosteroid pharmaceutical composition to the subject.

In some embodiments, the third series of filters includes one or more filters listed in Table 5. In some embodiments, the third plurality of filters includes a steroid medication filter, a pulmonary function filter, and an asthma reduction filter.

In some embodiments, the fourth series of filters includes one or more filters listed in Table 6. In some embodiments, the fourth plurality of filters includes an infectious disease contact filter, a symptoms of infection filter, a vision deterioration filter, an oral health filter, an infection filter, a surgery filter, a bone density filter, and an ocular disease filter.

In some embodiments, the third and fourth plurality of filters includes filters selected from the filters listed in Table 8. In some embodiments, the third plurality of filters of the first category class include a third sub-plurality of the filters listed in Table 8, for example, 2, 3, 4, 5, 6, 7, 8, 9, 10, 11, 12, 13, 14, or all 15 of the filters listed in Table 8, and the fourth plurality of filters of the first category class include a fourth sub-plurality of the filters listed in Table 8, which is different from the third sub-plurality of filters, for example, 2, 3, 4, 5, 6, 7, 8, 9, 10, 11, 12, 13, 14, or all 15 of the filters listed in Table 8. In some embodiments, each of the filters in the third sub-plurality of filters is different from each of the filters in the fourth sub-plurality of filters (e.g., no filter listed in Table 8 is included in both the first sub-plurality and the second sub-plurality of filters). In some embodiments, a system for qualifying a subject for delivery of an over-the-counter corticosteroid pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 8, e.g., at least 2, 3, 4, 5, 6, 7, 8, 9, 10, 11, 12, 13, 14, or all 15 of the filters listed in Table 8. In some embodiments, where a filter listed in Table 8 corresponds to a filter listed in Table 2, Table 3, Table 5, or Table 6, a threshold level sufficient to fire the corresponding filter listed in Table 2, Table 3, Table 5, or Table 6, as described in detail above, is sufficient to fire the filter listed in Table 8.

TABLE 8

Example filters for re-qualifying a subject for an over-the-counter provision of a corticosteroid pharmaceutical composition.

| Filter | Example Criteria |
| --- | --- |
| 1b | an allergy filter |
| 2b | a steroid medication filter |
| 3b | a pulmonary function filter |
| 4b | an asthma severity filter |
| 5b | an infectious disease contact filter |
| 6b | a symptoms of infection filter |
| 7b | a vision deterioration filter |

TABLE 8-continued

Example filters for re-qualifying a subject for an over-the-counter
provision of a corticosteroid pharmaceutical composition.

| Filter | Example Criteria |
|---|---|
| 8b | an oral health filter |
| 9b | a liver disease filter |
| 10b | an infection filter |
| 11b | a surgery filter |
| 12b | a bone density filter |
| 13b | an ocular disease filter |
| 14b | a drug interaction filter |
| 15b | a side effect filter |

In one aspect, the present disclosure provides a computer system for qualifying a human subject for over-the-counter delivery of a corticosteroid pharmaceutical composition for treating or preventing symptoms of asthma, the computer system comprising one or more processors and a memory, the memory comprising non-transitory instructions which, when executed by the one or more processor, perform a method comprising: a) conducting a first survey of the subject thereby obtaining a first plurality of survey results, wherein the first plurality of survey results indicates: whether the subject is already taking a steroid medication, an age of the subject, a pulmonary function status of the subject, an asthma severity of the subject, whether the subject has an untreated infection, a surgery status of the subject, a bone density status of the subject, and whether the subject has ever had cataracts or glaucoma; b) running all or a portion of the first plurality of survey results against a first plurality of filters of a first category class, wherein, when a respective filter in the first plurality of filters is fired, the subject is deemed not qualified for delivery of the corticosteroid pharmaceutical composition and the method is terminated without delivery of the corticosteroid pharmaceutical composition to the subject, wherein the first plurality of filters comprises: a first steroid medication filter that is fired at least when the first plurality of survey results indicates that the subject is already taking a steroid medication, an age filter, a first pulmonary function filter that is fired at least when the first plurality of survey results indicates that the subject has compromised pulmonary function, and a first asthma severity filter; c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises: a first infection filter that is fired at least when the first plurality of survey results indicates that the subject has a severe, untreated infection, a first surgery filter that is fired at least when the first plurality of survey results indicates that the subject is planning on undergoing surgery, a first bone density filter that is fired at least when the first plurality of survey results indicates that the subject has decreased bone mineral density, and a first ocular disease filter that is fired at least when the first plurality of survey results indicates that the subject has ever had cataracts or glaucoma; d) obtaining acknowledgment from the subject for the warning issued to the subject by any filter in the second plurality of filters; and e) proceeding with a fulfillment process when (i) no filter in the first plurality of filters has been fired and (ii) the subject has acknowledged each warning associated with each filter in the second plurality of filters that was fired, wherein the fulfillment process comprises: storing an indication in a subject profile of an initial order for the corticosteroid pharmaceutical composition, communicating an over-the-counter drug facts label for the corticosteroid pharmaceutical composition to the subject, and authorizing, upon confirmation from the subject that the over-the-counter drug facts label has been received and read, provision of the corticosteroid pharmaceutical composition to the subject.

In some embodiments, the corticosteroid pharmaceutical composition includes a class B corticosteroid. In some embodiments, the corticosteroid pharmaceutical composition includes a glucocorticosteroid.

In some embodiments, the corticosteroid pharmaceutical composition includes budesonide, or a pharmaceutically acceptable salt thereof. In some embodiments, upon confirmation from the subject that the over the counter drug facts label has been received and read, the subject is authorized for provision of a dosage of from 90 mcg to 270 mg of budesonide, or a pharmaceutically acceptable salt thereof, twice per day. In some embodiments, upon confirmation from the subject that the over the counter drug facts label has been received and read, the subject is authorized for provision of a dosage of 180 mcg of budesonide, or a pharmaceutically acceptable salt thereof, twice per day.

In some embodiments, the corticosteroid pharmaceutical composition includes ciclesonide, or a pharmaceutically acceptable salt thereof. In some embodiments, upon confirmation from the subject that the over the counter drug facts label has been received and read, the subject is authorized for provision of a dosage of from 40 mcg to 120 mg of ciclesonide, or a pharmaceutically acceptable salt thereof, twice per day. In some embodiments, upon confirmation from the subject that the over the counter drug facts label has been received and read, the subject is authorized for provision of a dosage of 80 mcg of ciclesonide, or a pharmaceutically acceptable salt thereof, twice per day.

In some embodiments, the corticosteroid pharmaceutical composition includes fluticasone furoate, or a pharmaceutically acceptable salt thereof. In some embodiments, upon confirmation from the subject that the over the counter drug facts label has been received and read, the subject is authorized for provision of a dosage of from 50 mcg to 150 mg of fluticasone furoate, or a pharmaceutically acceptable salt thereof, per day. In some embodiments, upon confirmation from the subject that the over the counter drug facts label has been received and read, the subject is authorized for provision of a dosage of 100 mcg of fluticasone furoate, or a pharmaceutically acceptable salt thereof, per day.

In some embodiments, the corticosteroid pharmaceutical composition includes mometasone furoate, or a pharmaceutically acceptable salt thereof. In some embodiments, upon confirmation from the subject that the over the counter drug facts label has been received and read, the subject is authorized for provision of a dosage of from 100 mcg to 300 mg of mometasone furoate, or a pharmaceutically acceptable salt thereof, per day. In some embodiments, upon confirmation from the subject that the over the counter drug facts label has been received and read, the subject is authorized for provision of a dosage of 200 mcg of mometasone furoate, or a pharmaceutically acceptable salt thereof, per day.

In some embodiments, the corticosteroid pharmaceutical composition includes fluticasone propionate, or a pharmaceutically acceptable salt thereof. In some embodiments, upon confirmation from the subject that the over the counter drug facts label has been received and read, the subject is authorized for provision of a dosage of from 44 mcg to 110 mg of fluticasone propionate twice per day, or a pharmaceutically acceptable salt thereof, per day. In some embodiments, upon confirmation from the subject that the over the counter drug facts label has been received and read, the subject is authorized for provision of a dosage of 88 mcg of fluticasone propionate, or a pharmaceutically acceptable salt thereof, twice per day.

In some embodiments, the corticosteroid pharmaceutical composition includes beclomethasone dipropionate, or a pharmaceutically acceptable salt thereof. In some embodiments, upon confirmation from the subject that the over the counter drug facts label has been received and read, the subject is authorized for provision of a dosage of from 40 mcg to 120 mg of beclomethasone dipropionate twice per day, or a pharmaceutically acceptable salt thereof, per day. In some embodiments, upon confirmation from the subject that the over the counter drug facts label has been received and read, the subject is authorized for provision of a dosage of 80 mcg of beclomethasone dipropionate, or a pharmaceutically acceptable salt thereof, twice per day.

In some embodiments, the age filter is fired when the first plurality of survey results indicates that the subject is less than eighteen years old.

In some embodiments, the compromised pulmonary function, capable of firing the first pulmonary filter, is a forced expiratory volume measured over one second (FEV1) of no more than 80% of a predicted volume for the subject.

In some embodiments (e.g., where the corticosteroid pharmaceutical composition includes budesonide), the first drug interaction filter is fired when the first plurality of survey results indicates that the subject is taking a medication selected from the group consisting of a corticosteroid medicine, an anticonvulsant, an immunosuppressant, ketoconazole, a medicine for the liver, and a prescription antiretroviral.

In some embodiments, the first plurality of survey results further indicates how frequently the subject experiences symptoms of asthma. In some embodiments, an infrequency with which the subject experiences symptoms of asthma, which is capable of firing the asthma severity filter, is less than twice a week. In some embodiments, a frequency with which the subject experiences symptoms of asthma, which is capable of firing the asthma severity filter, is more than six times a week.

In some embodiments, the first plurality of survey results further indicates how frequently symptoms of asthma disrupt the subject's sleep. In some embodiments, an infrequency with which the subject's sleep is disrupted by symptoms of asthma, which is capable of firing the asthma severity filter, is less than three times a month. In some embodiments, a frequency with which the subject's sleep is disrupted by symptoms of asthma, which is capable of firing the asthma severity filter, is more than four times a month.

In some embodiments, the first plurality of survey results further indicates how frequently the subject uses a rescue inhaler. In some embodiments, an infrequency with which the subject uses a rescue inhaler, which is capable of firing the asthma severity filter, is less than twice a week. In some embodiments, a frequency with which the subject uses a rescue inhaler, which is capable of firing the asthma severity filter, is more than six times a week In some embodiments, the first plurality of survey results further indicates how frequently the subject uses oral steroids. In some embodiments, a frequency with which the subject has used oral steroids, which is capable of firing the asthma severity filter, is more than once in the past year.

In some embodiments, the first plurality of survey results further indicates whether the subject is allergic to the corticosteroid pharmaceutical composition. Accordingly, the first plurality of filters includes an adverse reaction filter that is fired when the first plurality of survey results indicates that the subject is allergic to the corticosteroid pharmaceutical composition.

In some embodiments, the warning corresponding to a respective filter in the second plurality of filters comprises a prompt for the subject to indicate whether they have discussed the risk factor underlying the respective filter in the second plurality of filters that was fired with a health care provider. Acknowledgement is obtained from the subject when the subject indicates that they have discussed the risk factor underlying the respective filter in the second plurality of filters that was fired with a health care provider.

In some embodiments, the fulfillment process further comprises storing a destination associated with the subject in the subject profile.

In some embodiments, coordinating shipping of the corticosteroid pharmaceutical composition to a physical address associated with the subject.

In some embodiments of the aspects disclosed above, the method further comprises: f) responsive to receiving a re-order request from the subject for the corticosteroid pharmaceutical composition, performing a re-fulfillment procedure comprising: (i) conducting a second survey of the subject thereby obtaining a second plurality of survey results, wherein the second plurality of survey results indicates: whether the subject is already taking a steroid medication, a pulmonary function status of the subject, whether the subject has observed an improvement in the symptoms of asthma since receiving their last provision of the corticosteroid pharmaceutical composition (e.g., a severity of the subject's asthma when taking the corticosteroid pharmaceutical composition), whether the subject has or has been in contact with someone having chicken pox, measles, or tuberculosis since receiving their last provision of the corticosteroid pharmaceutical composition, whether the subject has experienced symptoms of an infection since receiving their last provision of the corticosteroid pharmaceutical composition, a vision deterioration status of the subject, an oral health status of the subject, whether the subject has developed an infection since receiving their last provision of the corticosteroid pharmaceutical composition, a surgery status of the subject, a bone density status of the subject, and whether the subject has developed cataracts or glaucoma since receiving their last provision of the corticosteroid pharmaceutical composition; (ii) running all or a portion of the second plurality of survey results against a third plurality of filters of the first category class, wherein, when a respective filter in the third plurality of filters is fired, the subject is deemed not qualified for the corticosteroid pharmaceutical composition and the re-fulfillment process is terminated without delivery of the corticosteroid pharmaceutical composition to the subject, wherein the third plurality of filters comprise: a second steroid medication filter that is fired at least when the second plurality of survey results indicates that the subject is already taking a steroid medication, a second pulmonary function filter that is fired at least when the second plurality of survey results indicates that the subject has severely compromised pulmonary function, and an asthma reduction filter that is fired when the second plurality of survey results indicates that the subject has not observed an improvement in symptoms of asthma; (iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises: an infectious disease contact filter that is fired at least when the second plurality of survey results indicates that the subject has or has been in contact with someone having chicken pox, measles, or tuberculosis since receiving their last provision of the corticosteroid pharmaceutical composition, a symptoms of infection filter that is fired at least when the second plurality of survey results indicates that the subject has experienced symptoms of an infection since receiving their last provision of the corticosteroid pharmaceutical composition, a vision deterioration filter that is fired at least when the second plurality of survey results indicates that the subject has developed a change in vision since receiving their last provision of the corticosteroid pharmaceutical composition, an oral health filter that is fired at least when the second plurality of survey results indicates that the subject has developed redness or white-colored patches in their mouth or throat since receiving their last provision of the corticosteroid pharmaceutical composition, a second infection filter that is fired at least when the second plurality of survey results indicates that the subject has a severe, untreated infection, a second surgery filter that is fired at least when the second plurality of survey results indicates that the subject is planning on undergoing surgery, a second bone density filter that is fired at least when the second plurality of survey results indicates that the subject has experienced decreased bone mineral density since receiving their last provision of the corticosteroid pharmaceutical composition, and a second ocular disease filter that is fired at least when the second plurality of survey results indicates that the subject has developed cataracts or glaucoma since receiving their last provision of the corticosteroid pharmaceutical composition; (iv) obtaining acknowledgment from the subject for the warning issued to the subject by any filter in the fourth plurality of filters; and (v) proceeding with the re-fulfillment process when (a) the re-fulfillment process is not already terminated by the firing of a filter in the third plurality of filters and (b) the subject has acknowledged each warning associated with each filter in the fourth plurality of filters that was fired, wherein the re-fulfillment process further comprises: storing an indication in the subject profile of a re-order for the corticosteroid pharmaceutical composition, communicating the over-the-counter drug facts label for the corticosteroid pharmaceutical composition to the subject, and authorizing, upon confirmation from the subject that the over-the-counter drug facts label has been received and read, a re-order provision of the corticosteroid pharmaceutical composition to the subject.

In some embodiments, the compromised pulmonary function, capable of firing the second pulmonary filter, is a forced expiratory volume measured over one second (FEV1) of no more than 80% of a predicted volume for the subject.

In some embodiments, the second plurality of survey results further indicates how frequently the subject experiences symptoms of asthma. Accordingly, a frequency with which the subject experiences symptoms of asthma, which is capable of firing the asthma reduction filter, is more than twice a week.

In some embodiments, the second plurality of survey results further indicates how frequently symptoms of asthma disrupt the subject's sleep. Accordingly, a frequency with which the subject's sleep is disrupted by symptoms of asthma, which is capable of firing the asthma reduction filter, is more than twice a month.

In some embodiments, the second plurality of survey results further indicates how frequently the subject uses a rescue inhaler, wherein a frequency with which the subject uses a rescue inhaler, which is capable of firing the asthma reduction filter, is more than twice a week.

In some embodiments, the second plurality of survey results further indicates how frequently the subject uses oral steroids, wherein a frequency with which the subject has used oral steroids, which is capable of firing the asthma reduction filter, is more than once in the past year.

In some embodiments of the aspects disclosed above, the second plurality of survey results further indicates whether the subject has experienced side effects associated with the corticosteroid pharmaceutical composition since receiving their last provision of the corticosteroid pharmaceutical composition, and the fourth plurality of filters further comprises a side effect filter that is fired at least when the second plurality of survey results indicates that the subject has experienced, since receiving their last provision of the corticosteroid pharmaceutical composition, a side effect selected from the group consisting of a sore nose, a sore throat, nausea, hay fever, an upper respiratory tract viral infection, gastroenteritis, and an ear infection.

In some embodiments of the aspects disclosed above, the re-fulfillment process further comprises, when a respective filter in the third plurality of filters or fourth plurality of filters is fired, storing a record associated with the firing of the respective filter in an adverse event profile comprising records of filter firing events associated with a plurality of subjects.

In one aspect, the disclosure provides a method for treating or preventing symptoms of asthma in a subject in need thereof, the method comprising: administering a (e.g., low-dose) corticosteroid pharmaceutical composition to a subject qualified for over-the-counter access to the corticosteroid pharmaceutical composition. In some embodiments, the subject is qualified for the over-the-counter access to the corticosteroid composition using a method, system, or computer readable medium disclosed herein.

In some embodiments, the corticosteroid pharmaceutical composition includes a class B corticosteroid. In some embodiments, the corticosteroid pharmaceutical composition includes a glucocorticosteroid.

In some embodiments, the corticosteroid pharmaceutical composition includes budesonide, or a pharmaceutically acceptable salt thereof. In some embodiments, the subject is administered from 90 mcg to 270 mg of budesonide, or a pharmaceutically acceptable salt thereof, twice per day. In some embodiments, the subject is administered 180 mcg of budesonide, or a pharmaceutically acceptable salt thereof, twice per day.

In some embodiments, the corticosteroid pharmaceutical composition includes ciclesonide, or a pharmaceutically acceptable salt thereof. In some embodiments, the subject is administered from 40 mcg to 120 mg of ciclesonide, or a pharmaceutically acceptable salt thereof, twice per day. In some embodiments, the subject is administered 80 mcg of ciclesonide, or a pharmaceutically acceptable salt thereof, twice per day.

In some embodiments, the corticosteroid pharmaceutical composition includes fluticasone furoate, or a pharmaceutically acceptable salt thereof. In some embodiments, the subject is administered from 50 mcg to 150 mg of fluticasone furoate, or a pharmaceutically acceptable salt thereof, per day. In some embodiments, the subject is administered 100 mcg of fluticasone furoate, or a pharmaceutically acceptable salt thereof, per day.

In some embodiments, the corticosteroid pharmaceutical composition includes mometasone furoate, or a pharmaceutically acceptable salt thereof. In some embodiments, the subject is administered from 50 mcg to 150 mg of mometasone furoate, or a pharmaceutically acceptable salt thereof, per day. In some embodiments, the subject is administered 100 mcg of mometasone furoate, or a pharmaceutically acceptable salt thereof, per day.

In some embodiments, the corticosteroid pharmaceutical composition includes fluticasone propionate, or a pharmaceutically acceptable salt thereof. In some embodiments, the subject is administered from 44 mcg to 110 mg of fluticasone propionate, or a pharmaceutically acceptable salt thereof, twice per day. In some embodiments, the subject is administered 88 mcg of fluticasone propionate, or a pharmaceutically acceptable salt thereof, twice per day.

In some embodiments, the corticosteroid pharmaceutical composition includes beclomethasone dipropionate, or a pharmaceutically acceptable salt thereof. In some embodiments, the subject is administered from 40 mcg to 120 mg of beclomethasone dipropionate, or a pharmaceutically acceptable salt thereof, twice per day. In some embodiments, the subject is administered 80 mcg of beclomethasone dipropionate, or a pharmaceutically acceptable salt thereof, twice per day.

In some embodiments, the disclosure provides methods for treating or preventing symptoms of asthma with an over the counter corticosteroid pharmaceutical composition. The method includes providing a first survey for obtaining a first information set from the human, via a computer system having a processor programmed to perform the first survey, where the first information set includes information about the human that relates to potential risk factors and contraindications for the corticosteroid pharmaceutical composition, as described herein. The method also includes applying an algorithm to the first information set, via a computer system having a processor programmed to perform the algorithm. The algorithm runs all or a portion of the first information set against a first plurality of filters, where the human is deemed not qualified for treatment with the over the counter corticosteroid pharmaceutical composition for treating or preventing symptoms of asthma when a respective filter in the first plurality of filters is fired and the method is terminated without authorizing provision of the corticosteroid pharmaceutical composition to the human, where the first plurality of filters includes filters related to contraindications of the corticosteroid pharmaceutical composition as described herein. The algorithm also runs all or a portion of the first information set against a second plurality of filters, where, when a respective filter in the second plurality of filters is fired, the human is provided with a warning corresponding to the respective filter, and where the second plurality of filters includes filters related to risk factors for the corticosteroid pharmaceutical composition as described herein. The algorithm also obtains acknowledgment from the human of the risk factor associated with each warning issued to the human by any filter in the second plurality of filters. In some embodiments, the acknowledgement includes confirmation that the human has discussed the risk factor with a physician. The algorithm proceeds with a fulfillment process when (a) no filter in the first plurality of filters has been fired and (b) the human has acknowledged each warning associated with each filter in the second plurality of filters that was fired. The fulfillment process includes storing an indication in a subject profile of an initial order for the corticosteroid pharmaceutical composition, communicating an over the counter drug facts label for the corticosteroid pharmaceutical composition to the human, and authorizing, upon confirmation from the subject that the over the counter drug facts label has been received and read, provision of the corticosteroid pharmaceutical composition to the human, where the authorization includes a destination associated with the subject. In some embodiments, the method also includes treating the human to treat or prevent symptoms of asthma of the human, upon authorization of the provision e.g., by providing access to the corticosteroid pharmaceutical composition to the human and/or by administering the corticosteroid pharmaceutical composition to treat or prevent symptoms of asthma in the human.

EXAMPLES

Example 1

A computer system is configured for qualifying a subject for over-the-counter delivery of a budesonide pharmaceutical composition (e.g., 16,17-(butylidenebis(oxy))-11,21-dihydroxy-, (11β,16-α)-pregna-1,4-diene-3,20-dione) to treat or prevent symptoms of asthma. The computer system includes instructions for conducting a survey of the subject. The survey is utilized to obtain one or more results indicating: whether the subject has a dairy allergy, whether the subject is already taking a steroid medication, an age of the subject, a pulmonary function status of the subject, an asthma severity of the subject, whether the subject has a liver problem, whether the subject has an untreated infection, a surgery status of the subject, a bone density status of the subject, whether the subject has ever had cataracts or glaucoma, and whether the subject is taking a medication that interacts (e.g., a pharmacokinetic interaction and/or a pharmacodynamic interaction) with budesonide.

The computer system runs survey results against a first series of filters that are each associated with a first filter category class. The first filter category class is configured to prevent authorization for OTC delivery of the OTC budesonide when the subject's survey results identify a contraindication for the budesonide. In some embodiments, the first series of filters includes one or more of a first dairy allergy filter, a first steroid medication filter, an age filter, a first pulmonary function filter, and an asthma severity filter. The dairy allergy filter is configured to ensure the subject is not allergic to milk protein. The steroid medication filter is configured to ensure the subject is not already taking a steroid medication. The age filter is configured to ensure that the subject is of appropriate age (e.g., eighteen years old or older). The pulmonary function filter is configured to ensure the subject has sufficient pulmonary function. The asthma severity filter is configured to ensure the subject has sufficiently severe asthma symptoms warranting daily use of a corticosteroid, but not such severe symptoms that a stronger, prescription medication should be administered (e.g., under the supervision of a medical professional).

The computer system runs survey results against a second series of filters that each generates a warning where the subject's survey results identify a risk factor for the OTC budesonide. The second series of filters includes a first liver disease filter, a first infection filter, a first surgery filter, a first bone density filter, a first ocular disease filter, and a first drug interaction filter. The first liver disease filter is configured to ensure that the subject does not have liver problems. The first infection filter is configured to ensure that the subject does not have an untreated infection. The first surgery filter is configured to ensure the subject is not planning to undergo a medical procedure. The first bone density filter is configured to ensure the subject has sufficient bone mineral density. The first ocular disease filter is configured to ensure the subject does not have an ocular disease such as cataracts or glaucoma. The first drug interaction filter is configured to ensure the subject is not taking a substance that interacts with budesonide, e.g., a corticosteroid medicine, an anticonvulsant, an immunosuppressant, ketoconazole, a medicine for the liver, or a prescription anti-retroviral.

The computer system then prompts the subject to acknowledge or deny having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC budesonide in a subject profile, and communicates an over-the-counter drug facts label for the budesonide pharmaceutical composition to the subject. Upon confirmation from the subject that they have received and read the over-the-counter drug facts label, the computer system authorizes provision of the OTC budesonide pharmaceutical composition to the subject.

In some embodiments, the computer system includes instructions for conducting another survey of the subject responsive to a re-order request of the budesonide pharmaceutical composition. This survey is utilized to obtain one or more results indicating: whether the subject has developed a dairy allergy since receiving their last provision of budesonide, whether the subject is already taking a steroid medication, a pulmonary function status of the subject, whether the subject has observed an improvement in the symptoms of asthma since receiving their last provision of the budesonide, whether the subject has or has been in contact with someone having chicken pox, measles, or tuberculosis since receiving their last provision of budesonide, whether the subject has experienced symptoms of an infection since receiving their last provision of budesonide, whether the subject has experienced vision deterioration since receiving their last provision of budesonide, an oral health status of the subject, whether the subject has developed a liver problem since receiving their last provision of budesonide, whether the subject has a severe, untreated infection, a surgery status of the subject, a bone density status of the subject, whether the subject has developed cataracts or glaucoma since receiving their last provision of budesonide, and whether the subject is taking a medication that interacts with budesonide.

The computer system runs survey results against a third series of filters that are each associated with the first filter category class. The third series of filters includes a second dairy allergy filter, a second steroid medication filter, a second pulmonary function filter, and an asthma reduction filter. The second dairy allergy filter is configured to ensure the subject is not, or has not developed, allergic to milk protein since receiving their last provision of budesonide. The second steroid medication filter is configured to ensure the subject is not taking a steroid medication. The pulmonary function filter is configured to ensure the subject has sufficient pulmonary function. The asthma reduction filter is configured to ensure the subject has observed an improvement in their symptoms of asthma since receiving their last provision of budesonide.

The computer system runs survey results against a fourth series of filters that each generates a warning where the subject's survey results identify a risk factor for the OTC budesonide. In some embodiments, the fourth series of filters includes an infectious disease contact filter, a symptoms of infection filter, a vision deterioration filter, an oral health filter, a second liver disease filter, a second infection filter, a second surgery filter, a second bone density filter, a second ocular disease filter, and a second drug interaction filter. The infectious disease contact filter is configured to ensure the subject has not been in contact with someone having chicken pox, tuberculosis, or measles since receiving their last provision of budesonide. The symptoms of infection filter are configured to ensure the subject has not experienced symptoms of an infection (e.g., fever) since receiving their last provision of budesonide. The vision deterioration filter is configured to ensure the subject has not experienced deterioration in their vision since receiving their last provision of budesonide. The oral health filter is configured to ensure the subject has not experience an oral infection (e.g., thrush) since receiving their last provision of budesonide. The second liver disease filter is configured to ensure that the subject has not developed a liver problem since receiving their last provision of budesonide. The second infection filter is configured to ensure the subject does not have an untreated infection. The second surgery filter is configured to ensure the subject is not planning on undergoing surgery. The second bone density filter is configured to ensure the subject has not experienced a decrease in bone mineral density since receiving their last provision of budesonide. The second ocular disease filter is configured to ensure the subject has not developed an ocular disease (e.g., glaucoma or cataracts) since receiving their last provision of budesonide. The second drug interaction filter is configured to ensure the subject has not started taking a substance that interacts with budesonide (e.g., a corticosteroid medicine, an anticonvulsant, an immunosuppressant, ketoconazole, a medicine for the liver, or a prescription anti-retroviral) since receiving their last provision of budesonide.

The computer system then prompts the subject to acknowledge or deny having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC budesonide in the subject profile, and communicates the over-the-counter drug facts label for the budesonide pharmaceutical composition to the subject. Upon confirmation from the subject that they have received and read the over-the-counter drug facts label, the computer system authorizes provision of the OTC budesonide pharmaceutical composition to the subject.

Example 2

A computer system is configured for qualifying a subject for over-the-counter delivery of a ciclesonide pharmaceutical composition 2-[(1S, 2S, 4R, 8S, 9S, 11S, 12S, 13R)-6-cyclohexyl-11-hydroxy-9, 13-dimethyl-16-oxo-5, 7-dioxapentacyclo [$10.8.0.0^{2,9}.0^{4,8}.0^{13,18}$] icosa-14, 17-dien-8-yl]-2-oxoethyl 2-methylpropanoate) to treat or prevent symptoms of asthma. The computer system includes instructions for conducting a survey of the subject. The survey is utilized to obtain one or more results indicating: whether the subject is already taking a steroid medication, an age of the subject, a pulmonary function status of the subject, a severity of the subject's asthma symptoms, whether the subject has an untreated infection, a surgery status of the subject, a bone density status of the subject, and whether the subject has ever had cataracts or glaucoma.

The computer system runs survey results against a first series of filters that are each associated with a first filter category class. The first filter category class is configured to prevent authorization for delivery of the OTC ciclesonide when the subject's survey results identify a contraindication for the ciclesonide. In some embodiments, the first series of filters includes one or more of a first steroid medication filter, an age filter, a first pulmonary function filter, and an asthma severity filter. The steroid medication filter is configured to ensure the subject is not already taking a steroid medication. The age filter is configured to ensure that the subject is of appropriate age (e.g., eighteen years old or older). The pulmonary function filter is configured to ensure the subject has sufficient pulmonary function. The asthma severity filter is configured to ensure the subject has sufficiently severe asthma symptoms warranting daily use of a corticosteroid, but not such severe symptoms that a stronger, prescription medication should be administered (e.g., under the supervision of a medical professional).

The computer system runs survey results against a second series of filters that each generates a warning where the subject's survey results identify a risk factor for the OTC ciclesonide. In some embodiments, the second series of filters includes filter, a first infection filter, a first surgery filter, a first bone density filter, and a first ocular disease filter. The first infection filter is configured to ensure that the subject does not have an untreated infection. The first surgery filter is configured to ensure the subject is not planning to undergo a medical procedure. The first bone density filter is configured to ensure the subject has sufficient bone mineral density. The first ocular disease filter is configured to ensure the subject does not have an ocular disease such as cataracts or glaucoma.

The computer system then prompts the subject to acknowledge having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC ciclesonide in a subject profile, and communicates an over-the-counter drug facts label for the ciclesonide pharmaceutical composition to the subject. Upon confirmation from the subject that they have received and read the over-the-counter drug facts label, the computer system authorizes provision of the OTC ciclesonide pharmaceutical composition to the subject.

In some embodiments, the computer system includes instructions for conducting another survey of the subject responsive to a re-order request of the ciclesonide pharmaceutical composition. This survey is utilized to obtain one or more results indicating: whether the subject is already taking a steroid medication, a pulmonary function status of the subject, whether the subject has observed an improvement in the symptoms of asthma since receiving their last provision of the ciclesonide, whether the subject has been in contact with someone having chicken pox, measles, or tuberculosis since receiving their last provision of ciclesonide, whether the subject has experienced symptoms of an infection (e.g., fever) since receiving their last provision of ciclesonide, a vision deterioration status of the subject, an oral health status of the subject, whether the subject has a severe, untreated infection, a surgery status of the subject, whether the subject has experienced decreased bone density since receiving their last provision of ciclesonide, and whether the subject has developed cataracts or glaucoma since receiving their last provision of ciclesonide.

The computer system runs survey results against a third series of filters that are each associated with the first filter category class. In some embodiments, the third series of filters includes one or more of a second steroid medication filter, a second pulmonary function filter, and an asthma reduction filter. The second steroid medication filter is configured to ensure the subject is not taking a steroid medication. The pulmonary function filter is configured to ensure the subject has sufficient pulmonary function. The asthma reduction filter is configured to ensure the subject has observed an improvement in their symptoms of asthma since receiving their last provision of ciclesonide.

The computer system runs survey results against a fourth series of filters that each generates a warning where the subject's survey results identify a risk factor for the OTC ciclesonide. In some embodiments, the fourth series of filters includes an infectious disease contact filter, a symptoms of infection filter, a vision deterioration filter, an oral health filter, a second infection filter, a second surgery filter, a second bone density filter, and a second ocular disease filter. The infectious disease contact filter is configured to ensure the subject has not been in contact with someone having chicken pox, tuberculosis, or measles since receiving their last provision of ciclesonide. The symptoms of infection filter are configured to ensure the subject has not experienced symptoms of an infection (e.g., fever) since receiving their last provision of ciclesonide. The vision deterioration filter is configured to ensure the subject has not experienced deterioration in their vision since receiving their last provision of ciclesonide. The oral health filter is configured to ensure the subject has not experience an oral infection (e.g., thrush) since receiving their last provision of ciclesonide. The second infection filter is configured to ensure the subject does not have an untreated infection. The second surgery filter is configured to ensure the subject is not planning on undergoing surgery. The second bone density filter is configured to ensure the subject has not experienced a decrease in bone mineral density since receiving their last provision of ciclesonide. The second ocular disease filter is configured to ensure the subject has not developed an ocular disease (e.g., glaucoma or cataracts) since receiving their last provision of ciclesonide.

The computer system then prompts the subject to acknowledge or deny having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC ciclesonide in the subject profile, and communicates the over-the-counter drug facts label for the ciclesonide pharmaceutical composition to the subject. Upon confirmation from the subject that they have received and read the over-the-counter drug facts label, the computer system authorizes provision of the OTC ciclesonide pharmaceutical composition to the subject.

Example 3

A computer system is configured for qualifying a subject for over-the-counter delivery of a mometasone furoate pharmaceutical composition (e.g., (9R,10S,11S,13S,14S,16R,17R)-9-chloro-17-(2-chloroacetyl)-11-hydroxy-10,13,16-trimethyl-3-oxo-6,7,8,9,10,11,12,13,14,15,16,17-dodecahydro-3H-cyclopenta[a]phenanthren-17-yl furan-2-carboxylate) to treat or prevent symptoms of asthma. The computer system includes instructions for conducting a survey of the subject. The survey is utilized to obtain one or more results indicating: whether the subject has a dairy allergy, whether the subject is already taking a steroid medication, an age of the subject, a pulmonary function status of the subject, a severity of the subject's asthma, whether the subject has a liver problem, whether the subject has an untreated infection, a surgery status of the subject, a bone density status of the subject, whether the subject has ever had cataracts or glaucoma, and whether the subject is taking a medication that interacts (e.g., a pharmacokinetic interaction and/or a pharmacodynamic interaction) with mometasone furoate.

The computer system runs survey results against a first series of filters that are each associated with a first filter category class. The first filter category class is configured to prevent authorization for OTC delivery of the OTC mometasone furoate when the subject's survey results identify a contraindication for the mometasone furoate. The first series of filters includes one or more of a first dairy allergy filter, a first steroid medication filter, an age filter, a first pulmonary function filter, and an asthma severity filter. The dairy allergy filter is configured to ensure the subject is not allergic to milk protein. The steroid medication filter is configured to ensure the subject is not already taking a steroid medication. The age filter is configured to ensure that the subject is of appropriate age (e.g., eighteen years old or older). The pulmonary function filter is configured to ensure the subject has sufficient pulmonary function. The asthma severity filter is configured to ensure the subject has sufficiently severe asthma symptoms warranting daily use of a corticosteroid, but not such severe symptoms that a stronger, prescription medication should be administered (e.g., under the supervision of a medical professional).

The computer system runs survey results against a second series of filters that each generates a warning where the subject's survey results identify a risk factor for the OTC mometasone furoate. In some embodiments, the second series of filters includes a first liver disease filter, a first infection filter, a first surgery filter, a first bone density filter, a first ocular disease filter, and a first drug interaction filter. The first liver disease filter is configured to ensure that the subject does not have liver problems. The first infection filter is configured to ensure that the subject does not have an untreated infection. The first surgery filter is configured to ensure the subject is not planning to undergo a medical procedure. The first bone density filter is configured to ensure the subject has sufficient bone mineral density. The first ocular disease filter is configured to ensure the subject does not have an ocular disease such as cataracts or glaucoma. The first drug interaction filter is configured to ensure the subject is not taking a substance that interacts with mometasone furoate.

The computer system then prompts the subject to acknowledge having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC mometasone furoate in a subject profile, and communicates an over-the-counter drug facts label for the mometasone furoate pharmaceutical composition to the subject. Upon confirmation from the subject that they have received and read the over-the-counter drug facts label, the computer system authorizes provision of the OTC mometasone furoate pharmaceutical composition to the subject.

In some embodiments, the computer system includes instructions for conducting another survey of the subject responsive to a re-order request of the mometasone furoate pharmaceutical composition. This survey is utilized to obtain one or more results indicating: whether the subject has developed a dairy allergy since receiving their last provision of mometasone furoate, whether the subject is already taking a steroid medication, a pulmonary function status of the subject, whether the subject has observed an improvement in the symptoms of asthma since receiving their last provision of mometasone furoate, whether the subject has been in contact with someone having chicken pox, measles, or tuberculosis since receiving their last provision of mometasone furoate, whether the subject has experienced symptoms of an infection (e.g., fever) since receiving their last provision of mometasone furoate, a vision deterioration status of the subject, an oral health status of the subject, whether the subject has developed a liver problem since receiving their last provision of mometasone furoate, whether the subject has a severe, untreated infection, a surgery status of the subject, whether the subject has experienced decreased bone density since receiving their last provision of mometasone furoate, whether the subject has developed cataracts or glaucoma since receiving their last provision of mometasone furoate, and whether the subject is taking a medication that interacts with mometasone furoate.

The computer system runs survey results against a third series of filters that are each associated with the first filter category class. In some embodiments, the third series of filters includes one or more of a second dairy allergy filter, a second steroid medication filter, a second pulmonary function filter, and an asthma reduction filter. The second dairy allergy filter is configured to ensure the subject is not, or has not developed, allergic to milk protein since receiving their last provision of mometasone furoate. The second steroid medication filter is configured to ensure the subject is not taking a steroid medication. The pulmonary function filter is configured to ensure the subject has sufficient pulmonary function. The asthma reduction filter is configured to ensure the subject has observed an improvement in their symptoms of asthma since receiving their last provision of mometasone furoate.

The computer system runs survey results against a fourth series of filters that each generates a warning where the subject's survey results identify a risk factor for the OTC mometasone furoate. In some embodiments, the fourth series of filters includes an infectious disease contact filter, a symptoms of infection filter, a vision deterioration filter, an oral health filter, a second liver disease filter, a second infection filter, a second surgery filter, a second bone density filter, a second ocular disease filter, and a second drug interaction filter. The infectious disease contact filter is configured to ensure the subject has not been in contact with someone having chicken pox, tuberculosis, or measles since receiving their last provision of mometasone furoate. The symptoms of infection filter are configured to ensure the subject has not experienced symptoms of an infection (e.g., fever) since receiving their last provision of mometasone furoate. The vision deterioration filter is configured to ensure the subject has not experienced deterioration in their vision since receiving their last provision of mometasone furoate. The oral health filter is configured to ensure the subject has not experience an oral infection (e.g., thrush) since receiving their last provision of mometasone furoate. The second liver disease filter is configured to ensure that the subject has not developed a liver problem since receiving their last provision of mometasone furoate. The second infection filter is configured to ensure the subject does not have an untreated infection. The second surgery filter is configured to ensure the subject is not planning on undergoing surgery. The second bone density filter is configured to ensure the subject has not experienced a decrease in bone mineral density since receiving their last provision of mometasone furoate. The second ocular disease filter is configured to ensure the subject has not developed an ocular disease (e.g., glaucoma or cataracts) since receiving their last provision of mometasone furoate. The second drug interaction filter is configured to ensure the subject has not started taking a substance that interacts with mometasone furoate since receiving their last provision of mometasone furoate.

The computer system then prompts the subject to acknowledge having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC mometasone furoate in the subject profile, and communicates the over-the-counter drug facts label for the mometasone furoate pharmaceutical composition to the subject. Upon confirmation from the subject that they have received and read the over-the-counter drug facts label, the computer system authorizes provision of the OTC mometasone furoate pharmaceutical composition to the subject.

Example 4

A computer system is configured for qualifying a subject for over-the-counter delivery of a fluticasone propionate pharmaceutical composition (e.g., 5-(fluoromethyl)-6α,9-difluoro-11β, 17-dihydroxy-16α-methyl-3-oxoandrosta-1,4-diene-17β-carbothioate, 17-propanoate) to treat or prevent symptoms of asthma. The computer system includes instructions for conducting a survey of the subject. The survey is utilized to obtain one or more results indicating: whether the subject is already taking a steroid medication, an age of the subject, a pulmonary function status of the subject, a severity of the subject's asthma, whether the subject has a liver problem, whether the subject has a severe, untreated infection, a surgery status of the subject, a bone density status of the subject, whether the subject has ever had cataracts or glaucoma, and whether the subject is taking a medication that interacts (e.g., a pharmacokinetic interaction and/or a pharmacodynamic interaction) with fluticasone propionate.

The computer system runs survey results against a first series of filters that are each associated with a first filter category class. The first filter category class is configured to prevent authorization for OTC delivery of the OTC fluticasone propionate when the subject's survey results identify a contraindication for the fluticasone propionate. In some embodiments, the first series of filters includes one or more of a first steroid medication filter, an age filter, a first pulmonary function filter, and an asthma severity filter. The steroid medication filter is configured to ensure the subject is not already taking a steroid medication. The age filter is configured to ensure that the subject is of appropriate age (e.g., eighteen years old or older). The pulmonary function filter is configured to ensure the subject has sufficient pulmonary function. The asthma severity filter is configured to ensure the subject has sufficiently severe asthma symptoms warranting daily use of a corticosteroid, but not such severe symptoms that a stronger, prescription medication should be administered (e.g., under the supervision of a medical professional).

The computer system runs survey results against a second series of filters that each generates a warning where the subject's survey results identify a risk factor for the OTC fluticasone propionate. In some embodiments, the second series of filters includes a first liver disease filter, a first infection filter, a first surgery filter, a first bone density filter, a first ocular disease filter, and a first drug interaction filter. The first liver disease filter is configured to ensure that the subject does not have liver problems. The first infection filter is configured to ensure that the subject does not have an untreated infection. The first surgery filter is configured to ensure the subject is not planning to undergo a medical procedure. The first bone density filter is configured to ensure the subject has sufficient bone mineral density. The first ocular disease filter is configured to ensure the subject does not have an ocular disease such as cataracts or glaucoma. The first drug interaction filter is configured to ensure the subject is not taking a substance that interacts with fluticasone propionate.

The computer system then prompts the subject to acknowledge having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC fluticasone propionate in a subject profile, and communicates an over-the-counter drug facts label for the fluticasone propionate pharmaceutical composition to the subject. Upon confirmation from the subject that they have received and read the over-the-counter drug facts label, the computer system authorizes provision of the OTC fluticasone propionate pharmaceutical composition to the subject.

In some embodiments, the computer system includes instructions for conducting another survey of the subject responsive to a re-order request of the fluticasone propionate pharmaceutical composition. This survey is utilized to obtain one or more results indicating: whether the subject is already taking a steroid medication, a pulmonary function status of the subject, whether the subject has observed an improvement in the symptoms of asthma since receiving their last provision of fluticasone propionate, whether the subject has been in contact with someone having chicken pox, measles, or tuberculosis since receiving their last provision of fluticasone propionate, whether the subject has experienced symptoms of an infection (e.g., fever) since receiving their last provision of fluticasone propionate, a vision deterioration status of the subject, an oral health status of the subject, whether the subject has developed a liver problem since receiving their last provision of fluticasone propionate, whether the subject has a severe, untreated infection since receiving their last provision of fluticasone propionate, a surgery status of the subject, whether the subject has experienced decreased bone density since receiving their last provision of fluticasone propionate, whether the subject has developed cataracts or glaucoma asthma since receiving their last provision of fluticasone propionate, and whether the subject has started taking a medication that interacts with fluticasone propionate.

The computer system runs survey results against a third series of filters that are each associated with the first filter category class. In some embodiments, the third series of filters includes one or more of a second steroid medication filter, a second pulmonary function filter, and asthma reduction filter. The second steroid medication filter is configured to ensure the subject is not taking a steroid medication. The pulmonary function filter is configured to ensure the subject has sufficient pulmonary function. The asthma reduction filter is configured to ensure the subject has observed an improvement in their symptoms of asthma since receiving their last provision of fluticasone propionate.

The computer system runs survey results against a fourth series of filters that each generates a warning where the subject's survey results identify a risk factor for the OTC fluticasone propionate. In some embodiments, the fourth series of filters includes an infectious disease contact filter, a symptoms of infection filter, a vision deterioration filter, an oral health filter, a second liver disease filter, a second infection filter, a second surgery filter, a second bone density filter, a second ocular disease filter, and a second drug interaction filter. The infectious disease contact filter is configured to ensure the subject has not been in contact with someone having chicken pox, tuberculosis, or measles since receiving their last provision of fluticasone propionate. The symptoms of infection filter are configured to ensure the subject has not experienced symptoms of an infection (e.g., fever) since receiving their last provision of fluticasone propionate. The vision deterioration filter is configured to ensure the subject has not experienced deterioration in their vision since receiving their last provision of fluticasone propionate. The oral health filter is configured to ensure the subject has not experience an oral infection (e.g., thrush) since receiving their last provision of fluticasone propionate. The second liver disease filter is configured to ensure that the subject has not developed a liver problem since receiving their last provision of fluticasone propionate. The second infection filter is configured to ensure the subject does not have an untreated infection. The second surgery filter is configured to ensure the subject is not planning on undergoing surgery. The second bone density filter is configured to ensure the subject has not experienced a decrease in bone mineral density since receiving their last provision of fluticasone propionate. The second ocular disease filter is configured to ensure the subject has not developed an ocular disease (e.g., glaucoma or cataracts) since receiving their last provision of fluticasone propionate. The second drug interaction filter is configured to ensure the subject is not taking a substance that interacts with fluticasone propionate since receiving their last provision of fluticasone propionate.

The computer system then prompts the subject to acknowledge or deny having discussed these warnings with a medical professional (e.g., their physician or healthcare provider). The computer system then proceeds with a re-fulfillment process only when none of the third series of filters was fired and the subject acknowledged that they discussed each warning issued in association with the fourth series of filters that was fired.

The computer system stores an indication of a re-order of the OTC fluticasone propionate in the subject profile, and communicates the over-the-counter drug facts label for the fluticasone propionate pharmaceutical composition to the subject. Upon confirmation from the subject that they have received and read the over-the-counter drug facts label, the computer system authorizes provision of the OTC fluticasone propionate pharmaceutical composition to the subject.

Example 5

A computer system is configured for qualifying a subject for over-the-counter delivery of a beclomethasone dipropionate pharmaceutical composition (e.g., (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phenanthren-17-yl propionate) to treat or prevent symptoms of asthma. The computer system includes instructions for conducting a survey of the subject. The survey is utilized to obtain results indicating: whether the subject is already taking a steroid medication, an age of the subject, a pulmonary function status of the subject, a severity of the subject's asthma, whether the subject has an untreated infection, a surgery status of the subject, a bone density status of the subject, and whether the subject has ever had cataracts or glaucoma.

The computer system runs survey results against a first series of filters that are each associated with a first filter category class. The first filter category class is configured to prevent authorization for OTC delivery of the OTC beclomethasone dipropionate when the subject's survey results identify a contraindication for the beclomethasone dipropionate. In some embodiments, the first series of filters includes one or more of a first steroid medication filter, an age filter, a first pulmonary function filter, and an asthma severity filter. The steroid medication filter is configured to ensure the subject is not already taking a steroid medication. The age filter is configured to ensure that the subject is of appropriate age (e.g., eighteen years old or older). The pulmonary function filter is configured to ensure the subject has sufficient pulmonary function. The asthma severity filter is configured to ensure the subject has sufficiently severe asthma symptoms warranting daily use of a corticosteroid, but not such severe symptoms that a stronger, prescription medication should be administered (e.g., under the supervision of a medical professional).

The computer system runs survey results against a second series of filters that each generates a warning where the subject's survey results identify a risk factor for the OTC beclomethasone dipropionate. In some embodiments, the second series of filters includes filter, a first infection filter, a first surgery filter, a first bone density filter, and a first ocular disease filter. The first infection filter is configured to ensure that the subject does not have an untreated infection. The first surgery filter is configured to ensure the subject is not planning to undergo a medical procedure. The first bone density filter is configured to ensure the subject has sufficient bone mineral density. The first ocular disease filter is configured to ensure the subject does not have an ocular disease such as cataracts or glaucoma.

The computer system then prompts the subject to acknowledge having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC beclomethasone dipropionate in a subject profile, and communicates an over-the-counter drug facts label for the beclomethasone dipropionate pharmaceutical composition to the subject. Upon confirmation from the subject that they have received and read the over-the-counter drug facts label, the computer system authorizes provision of the OTC beclomethasone dipropionate pharmaceutical composition to the subject.

In some embodiments, the computer system includes instructions for conducting another survey of the subject responsive to a re-order request of the beclomethasone dipropionate pharmaceutical composition. This survey is utilized to obtain results indicating: whether the subject is already taking a steroid medication, a pulmonary function status of the subject, whether the subject has observed an improvement in the symptoms of asthma since receiving their last provision of beclomethasone dipropionate, whether the subject has been in contact with someone having chicken pox, measles, or tuberculosis since receiving their last provision of beclomethasone dipropionate, whether the subject has experienced symptoms (e.g., fever) of an infection since receiving their last provision of beclomethasone dipropionate, a vision deterioration status of the subject, an oral health status of the subject, whether the subject has a severe, untreated infection, a surgery status of the subject, whether the subject has experienced decreased bone density since receiving their last provision of beclomethasone dipropionate, and whether the subject has developed cataracts or glaucoma since receiving their last provision of beclomethasone dipropionate.

The computer system runs survey results against a third series of filters that are each associated with the first filter category class. In some embodiments, the third series of filters includes one or more of a second steroid medication filter, a second pulmonary function filter, and an asthma reduction filter. The second steroid medication filter is configured to ensure the subject is not taking a steroid medication. The pulmonary function filter is configured to ensure the subject has sufficient pulmonary function. The asthma reduction filter is configured to ensure the subject has observed an improvement in their symptoms of asthma since receiving their last provision of beclomethasone dipropionate.

The computer system runs survey results against a fourth series of filters that each generates a warning where the subject's survey results identify a risk factor for the OTC beclomethasone dipropionate. In some embodiments, the fourth series of filters includes an infectious disease contact filter, a symptoms of infection filter, a vision deterioration filter, an oral health filter, a second infection filter, a second surgery filter, a second bone density filter, and a second ocular disease filter. The infectious disease contact filter is configured to ensure the subject has not been in contact with someone having chicken pox, tuberculosis, or measles since receiving their last provision of beclomethasone dipropionate. The symptoms of infection filter are configured to ensure the subject has not experienced symptoms of an infection (e.g., fever) since receiving their last provision of beclomethasone dipropionate. The vision deterioration filter is configured to ensure the subject has not experienced deterioration in their vision since receiving their last provision of beclomethasone dipropionate. The oral health filter is configured to ensure the subject has not experience an oral infection (e.g., thrush) since receiving their last provision of beclomethasone dipropionate. The second infection filter is configured to ensure the subject does not have an untreated infection. The second surgery filter is configured to ensure the subject is not planning on undergoing surgery. The second bone density filter is configured to ensure the subject has not experienced a decrease in bone mineral density since receiving their last provision of beclomethasone dipropionate. The second ocular disease filter is configured to ensure the subject has not developed an ocular disease (e.g., glaucoma or cataracts) since receiving their last provision of beclomethasone dipropionate.

The computer system then prompts the subject to acknowledge having discussed these warnings with a medical professional (e.g., their physician or healthcare provider). The computer system then proceeds with a re-fulfillment process only when none of the third series of filters was fired and the subject acknowledged that they discussed each warning issued in association with the fourth series of filters that was fired.

The computer system stores an indication of a re-order of the OTC beclomethasone dipropionate in the subject profile, and communicates the over-the-counter drug facts label for the beclomethasone dipropionate pharmaceutical composition to the subject. Upon confirmation from the subject that they have received and read the over-the-counter drug facts label, the computer system authorizes provision of the OTC beclomethasone dipropionate pharmaceutical composition to the subject.

Example 6

A computer system is configured for qualifying a subject for over-the-counter delivery of a fluticasone furoate pharmaceutical composition (e.g., (6α,11β,16α,17α)-6,9-difluoro-17-{[(fluoro-methyl)thio]carbonyl}-11-hydroxy-16-methyl-3-oxoandrosta-1,4-dien-17-yl 2-furancarboxylate) to treat or prevent symptoms of asthma. The computer system includes instructions for conducting a survey of the subject. The survey is utilized to obtain one or more results indicating: whether the subject has a dairy allergy, whether the subject is already taking a steroid medication, an age of the subject, a pulmonary function status of the subject, a severity of the subject's asthma, whether the subject has a liver problem, whether the subject has an untreated infection, a surgery status of the subject, a bone density status of the subject, whether the subject has ever had cataracts or glaucoma, and whether the subject is taking a medication that interacts (e.g., a pharmacokinetic interaction and/or a pharmacodynamic interaction) with fluticasone furoate.

The computer system runs survey results against a first series of filters that are each associated with a first filter category class. The first filter category class is configured to prevent authorization for OTC delivery of the OTC fluticasone furoate when the subject's survey results identify a contraindication for the fluticasone furoate. The first series of filters includes one or more of a first dairy allergy filter, a first steroid medication filter, an age filter, a first pulmonary function filter, and an asthma severity filter. The dairy allergy filter is configured to ensure the subject is not allergic to milk protein. The steroid medication filter is configured to ensure the subject is not already taking a steroid medication. The age filter is configured to ensure that the subject is of appropriate age (e.g., eighteen years old or older). The pulmonary function filter is configured to ensure the subject has sufficient pulmonary function. The asthma severity filter is configured to ensure the subject has sufficiently severe asthma symptoms warranting daily use of a corticosteroid, but not such severe symptoms that a stronger, prescription medication should be administered (e.g., under the supervision of a medical professional).

The computer system runs survey results against a second series of filters that each generates a warning where the subject's survey results identify a risk factor for the OTC fluticasone furoate. In some embodiments, the second series of filters includes a first liver disease filter, a first infection filter, a first surgery filter, a first bone density filter, a first ocular disease filter, and a first drug interaction filter. The first liver disease filter is configured to ensure that the subject does not have liver problems. The first infection filter is configured to ensure that the subject does not have an untreated infection. The first surgery filter is configured to ensure the subject is not planning to undergo a medical procedure. The first bone density filter is configured to ensure the subject has sufficient bone mineral density. The first ocular disease filter is configured to ensure the subject does not have an ocular disease such as cataracts or glaucoma. The first drug interaction filter is configured to ensure the subject is not taking a substance that interacts with fluticasone furoate.

The computer system then prompts the subject to acknowledge having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC fluticasone furoate in a subject profile, and communicates an over-the-counter drug facts label for the fluticasone furoate pharmaceutical composition to the subject. Upon confirmation from the subject that they have received and read the over-the-counter drug facts label, the computer system authorizes provision of the OTC fluticasone furoate pharmaceutical composition to the subject.

In some embodiments, the computer system includes instructions for conducting another survey of the subject responsive to a re-order request of the fluticasone furoate pharmaceutical composition. This survey is utilized to obtain one or more results indicating: whether the subject has developed a dairy allergy since receiving their last provision of fluticasone furoate, whether the subject is already taking a steroid medication, a pulmonary function status of the subject, whether the subject has observed an improvement in the symptoms of asthma since receiving their last provision of fluticasone furoate, whether the subject has been in contact with someone having chicken pox, measles, or tuberculosis since receiving their last provision of fluticasone furoate, whether the subject has experienced symptoms of an infection (e.g., fever) since receiving their last provision of fluticasone furoate, a vision deterioration status of the subject, an oral health status of the subject, whether the subject has developed a liver problem since receiving their last provision of fluticasone furoate, whether the subject has a severe, untreated infection, a surgery status of the subject, whether the subject has experienced decreased bone density since receiving their last provision of fluticasone furoate, whether the subject has developed cataracts or glaucoma since receiving their last provision of fluticasone furoate, and whether the subject has started taking a medication that interacts with fluticasone furoate.

The computer system runs survey results against a third series of filters that are each associated with the first filter category class. In some embodiments, the third series of filters includes one or more of a second dairy allergy filter, a second steroid medication filter, a second pulmonary function filter, and an asthma reduction filter. The second dairy allergy filter is configured to ensure the subject is not, or has not developed, allergic to milk protein since receiving their last provision of fluticasone furoate. The second steroid medication filter is configured to ensure the subject is not taking a steroid medication. The pulmonary function filter is configured to ensure the subject has sufficient pulmonary function. The asthma reduction filter is configured to ensure the subject has observed an improvement in their symptoms of asthma since receiving their last provision of fluticasone furoate.

The computer system runs survey results against a fourth series of filters that each generates a warning where the subject's survey results identify a risk factor for the OTC fluticasone furoate. In some embodiments, the fourth series of filters includes an infectious disease contact filter, a symptoms of infection filter, a vision deterioration filter, an oral health filter, a second liver disease filter, a second infection filter, a second surgery filter, a second bone density filter, a second ocular disease filter, and a second drug interaction filter. The infectious disease contact filter is configured to ensure the subject has not been in contact with someone having chicken pox, tuberculosis, or measles since receiving their last provision of fluticasone furoate. The symptoms of infection filter are configured to ensure the subject has not experienced symptoms of an infection (e.g., fever) since receiving their last provision of fluticasone furoate. The vision deterioration filter is configured to ensure the subject has not experienced deterioration in their vision since receiving their last provision of fluticasone furoate. The oral health filter is configured to ensure the subject has not experience an oral infection (e.g., thrush) since receiving their last provision of fluticasone furoate. The second liver disease filter is configured to ensure that the subject has not developed a liver problem since receiving their last provision of fluticasone furoate. The second infection filter is configured to ensure the subject does not have an untreated infection. The second surgery filter is configured to ensure the subject is not planning on undergoing surgery. The second bone density filter is configured to ensure the subject has not experienced a decrease in bone mineral density since receiving their last provision of fluticasone furoate. The second ocular disease filter is configured to ensure the subject has not developed an ocular disease (e.g., glaucoma or cataracts) since receiving their last provision of fluticasone furoate. The second drug interaction filter is configured to ensure the subject has not started taking a substance that interacts with fluticasone furoate since receiving their last provision of fluticasone furoate.

The computer system then prompts the subject to acknowledge having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC fluticasone furoate in the subject profile, and communicates the over-the-counter drug facts label for the fluticasone furoate pharmaceutical composition to the subject. Upon confirmation from the subject that they have received and read the over-the-counter drug facts label, the computer system authorizes provision of the OTC fluticasone furoate pharmaceutical composition to the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

Figure 5C:
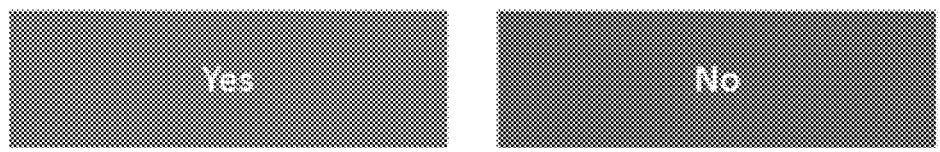
Figure 5D:
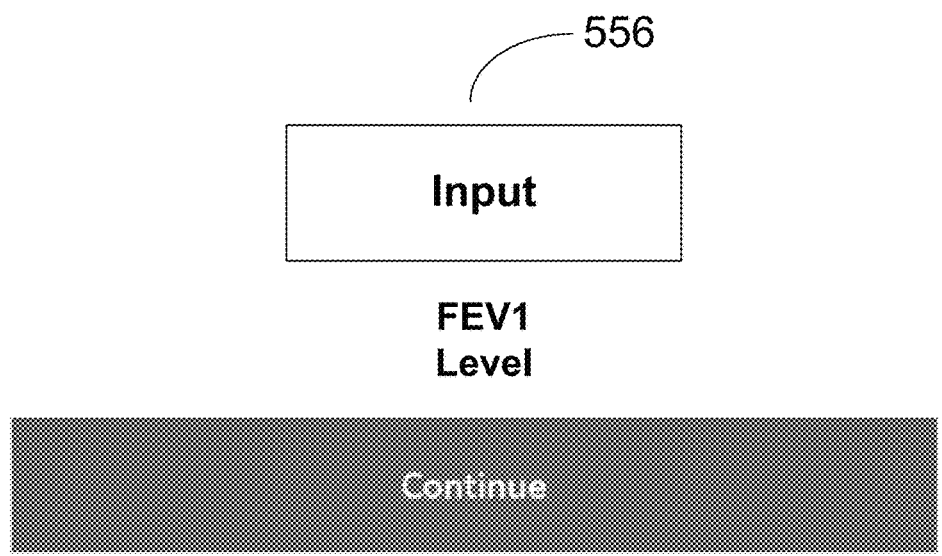

The present invention can be implemented as a computer program product that comprises a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of treating or preventing symptoms of asthma in a human subject with an over-the-counter corticosteroid pharmaceutical composition, the method comprising:
   A) providing a first survey for obtaining a first plurality of survey results about the subject, via a first computer system having a processor programed to perform the first survey, wherein the first plurality of survey results indicates:
      whether the subject is taking another steroid medication,
      an age of the subject,
      a pulmonary function status of the subject,
      a severity of the subject's asthma,
      whether the subject has an untreated infection,
      a surgery status of the subject,
      a bone density status of the subject, and
      whether the subject has ever had cataracts or glaucoma;
   B) applying an algorithm to the first plurality of survey results, via a second computer system having a process programed to perform the algorithm, wherein the algorithm is associated with an over-the-counter dosage of the corticosteroid pharmaceutical composition that is lower than a prescription dosage, and wherein the algorithm:
      i) runs all or a portion of the first plurality of survey results against a first plurality of filters of a first category class, wherein, when a respective filter in the first plurality of filters is fired, the subject is deemed not qualified for provision of the corticosteroid pharmaceutical composition and the method is terminated without authorizing provision of the corticosteroid pharmaceutical composition to the subject, wherein the first plurality of filters comprises:
         a first steroid medication filter that is fired at least when the first plurality of survey results indicates that the subject is taking a steroid medication,
         an age filter,
         a first pulmonary function filter that is fired at least when the first plurality of survey results indicates that the subject has compromised pulmonary function, and
         an asthma severity filter;
      ii) runs all or a portion of the first plurality of survey results against a second plurality of filters of a second category class, wherein, when a respective filter in the second plurality of filters is fired, the subject is provided with a warning corresponding to the respective filter, and wherein the second plurality of filters comprises:
         a first infection filter that is fired at least when the first plurality of survey results indicates that the subject has a severe, untreated infection,
         a first surgery filter that is fired at least when the first plurality of survey results indicates that the subject is planning on undergoing surgery,
         a first bone density filter that is fired at least when the first plurality of survey results indicates that the subject has decreased bone mineral density, and
         a first ocular disease filter that is fired at least when the first plurality of survey results indicates that the subject has ever had cataracts or glaucoma;
      iii) obtains acknowledgment from the subject for the warning issued to the subject by any filter in the second plurality of filters; and
      iv) proceeds with a fulfillment process when a) no filter in the first plurality of filters has been fired and b) the subject has acknowledged each warning associated with each filter in the second plurality of filters that was fired, wherein the fulfillment process comprises:
         storing, in a memory of the second computer system, an indication in a subject profile of an initial order for the corticosteroid pharmaceutical composition,
         communicating an over-the-counter drug facts label for the corticosteroid pharmaceutical composition to the subject, and
         authorizing, upon confirmation from the subject that the over-the-counter drug facts label has been received and read, provision of the corticosteroid pharmaceutical composition to the subject; and
   C) administering the corticosteroid pharmaceutical composition to the subject at the over-the-counter dosage that is lower than a prescription dosage after authorization of the provision.

2. The method of claim 1, wherein the corticosteroid pharmaceutical composition includes a class B corticosteroid.

3. The method of claim 1 wherein the corticosteroid pharmaceutical composition includes a glucocorticosteroid.

4. The method of claim 1, wherein the corticosteroid pharmaceutical composition includes budesonide as an active ingredient.

5. The method of claim 4, wherein, upon satisfying the requirements of the survey, the subject is authorized for an over-the-counter dosage of 90 mcg to 270 mcg of budesonide twice daily.

6. The method of claim 4, wherein, upon satisfying the requirements of the survey, the subject is authorized for an over-the-counter dosage of 180 mcg of budesonide twice daily.

7. The method of claim 4, wherein, upon satisfying the requirements of the survey, the subject is authorized for an over-the-counter dosage of 45 mcg of budesonide twice daily.

8. The method of claim 4, wherein, upon satisfying the requirements of the survey, the subject is authorized for an over-the-counter dosage of 90 mcg of budesonide twice daily.

9. The method of claim 4, wherein, upon satisfying the requirements of the survey, the subject is authorized for an over-the-counter dosage of between 90 mcg of budesonide and 180 mcg of budesonide twice daily.

10. The method of claim 1, wherein the corticosteroid pharmaceutical composition includes a composition selected from the group consisting of ciclesonide, fluticasone furoate, mometasone furoate, fluticasone propionate, and beclomethasone dipropionate.

11. The method of claim 1, wherein the compromised pulmonary function, capable of firing the first pulmonary filter, is a forced expiratory volume measured over one second (FEV1) of no more than 80% of a predicted volume for the subject.

12. The method of claim 1, wherein:
the first plurality of survey results further comprises an asthma severity status of the subject, and
the first plurality of filters includes a first asthma filter that is fired when the first plurality of survey results indicates that the subject has severe asthma.

13. The method of claim 1, wherein:
the first plurality of survey results further comprises how frequently the subject experiences symptoms of asthma, wherein:
an infrequency with which the subject experiences symptoms of asthma, which is capable of firing the first asthma filter, is less than twice a week, and
a frequency with which the subject experiences symptoms of asthma, which is capable of firing the first asthma filter, is more than six times a week.

14. The method of claim 1, wherein:
the first plurality of survey results further comprises how frequently symptoms of asthma disrupt the subject's sleep, wherein:
an infrequency with which the subject's sleep is disrupted by symptoms of asthma, which is capable of firing the first asthma filter, is less than three times a month, and
a frequency with which the subject's sleep is disrupted by symptoms of asthma, which is capable of firing the first asthma filter, is more than four times a month.

15. The method of claim 1, wherein:
the first plurality of survey results further comprises how frequently the subject uses a rescue inhaler, wherein:
an infrequency with which the subject uses a rescue inhaler, which is capable of firing the first asthma filter, is less than twice a week, and
a frequency with which the subject uses a rescue inhaler, which is capable of firing the first asthma filter, is more than six times a week.

16. The method of claim 1, wherein:
the first plurality of survey results further comprises how frequently the subject uses oral steroids, wherein a frequency with which the subject has used oral steroids, which is capable of firing the first asthma filter, is more than once in the past year.

17. The method of claim 1, wherein:
the warning corresponding to a respective filter in the second plurality of filters comprises a prompt for the user to indicate whether they have discussed the risk factor underlying the respective filter in the second plurality of filters that was fired with a health care provider; and
acknowledgement is obtained from the subject when the subject indicates that they have discussed the risk factor underlying the respective filter in the second plurality of filters that was fired with a health care provider.

18. The method of claim 1 further comprising:
D) receiving a re-order request from the subject for the corticosteroid pharmaceutical composition; and
E) performing a re-fulfillment procedure comprising:
i) providing a second survey for obtaining a second plurality of survey results, wherein the second plurality of survey results comprises:
whether the subject is taking a steroid medication,
a pulmonary function status of the subject,
whether the subject has observed an improvement in the symptoms of asthma since receiving their last provision of the corticosteroid pharmaceutical composition,
whether the subject has or has been in contact with someone having chicken pox, measles, or tuberculosis since receiving their last provision of the corticosteroid pharmaceutical composition,
whether the subject has experienced symptoms of an infection since receiving their last provision of the corticosteroid pharmaceutical composition,
a vision deterioration status of the subject,
an oral health status of the subject,
whether the subject has developed an infection since receiving their last provision of the corticosteroid pharmaceutical composition,
a surgery status of the subject,
a bone density status of the subject, and
whether the subject has developed cataracts or glaucoma since receiving their last provision of the corticosteroid pharmaceutical composition;
ii) running all or a portion of the second plurality of survey results against a third plurality of filters of the first category class, wherein, when a respective filter in the third plurality of filters is fired, the subject is deemed not qualified for the corticosteroid pharmaceutical composition and the re-fulfillment process is terminated without authorizing provision of the corticosteroid pharmaceutical composition to the subject, wherein the third plurality of filters comprises:
a second steroid medication filter that is fired at least when the second plurality of survey results indicates that the subject is taking a steroid medication,
a second pulmonary function filter that is fired at least when the second plurality of survey results indicates that the subject has compromised pulmonary function, and
an asthma reduction filter that is fired when the second plurality of survey results indicates that the subject has not observed an improvement in symptoms of asthma;
iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises:
an infectious disease contact filter that is fired at least when the second plurality of survey results indicates that the subject has or has been in contact with someone having chicken pox, measles, or tuberculosis since receiving their last provision of the corticosteroid pharmaceutical composition,
a symptoms of infection filter that is fired at least when the second plurality of survey results indicates that the subject has experienced symptoms of an infection,
a vision deterioration filter that is fired at least when the second plurality of survey results indicates that the subject has experienced a change in vision since receiving their last provision of the corticosteroid pharmaceutical composition,
an oral health filter that is fired at least when the second plurality of survey results indicates that the subject has experienced redness or white-colored patches in their mouth or throat since receiving their last provision of the corticosteroid pharmaceutical composition,
a second infection filter that is fired at least when the second plurality of survey results indicates that the subject has a severe, untreated infection,
a second surgery filter that is fired at least when the second plurality of survey results indicates that the subject is planning on undergoing surgery,
a second bone density filter that is fired at least when the second plurality of survey results indicates that the subject has decreased bone mineral density, and
a second ocular disease filter that is fired at least when the second plurality of survey results indicates that the subject has developed cataracts or glaucoma since receiving their last provision of the corticosteroid pharmaceutical composition,
iv) obtaining acknowledgment from the subject for the warning issued to the subject by any filter in the fourth plurality of filters; and
v) proceeding with the re-fulfillment process when (a) the re-fulfillment process is not already terminated by the firing of a filter in the third plurality of filters and (b) the subject has acknowledged each warning associated with each filter in the fourth plurality of filters that was fired, wherein the re-fulfillment process further comprises:
storing an indication in a subject profile of a re-order for the corticosteroid pharmaceutical composition,
communicating the over-the-counter drug facts label for the corticosteroid pharmaceutical composition to the subject, and
authorizing, upon confirmation from the subject that the over-the-counter drug facts label has been received and read, a re-order provision of the corticosteroid pharmaceutical composition to the subject; and
F) administering the corticosteroid pharmaceutical composition to the subject after authorization of the re-fulfillment.

19. The method of claim 18, wherein:
the second plurality of survey results further comprises how frequently the subject experiences symptoms of asthma since receiving their last provision of the corticosteroid pharmaceutical composition, wherein a frequency with which the subject experiences symptoms of asthma, which is capable of firing the asthma reduction filter, is more than twice a week.

20. The method of claim 18, wherein:
the second plurality of survey results further comprises how frequently symptoms of asthma disrupt the subject's sleep since receiving their last provision of the corticosteroid pharmaceutical composition, wherein a frequency with which the subject's sleep is disrupted by symptoms of asthma, which is capable of firing the asthma reduction filter, is more than twice a month.

21. The method of claim 18, wherein:
the second plurality of survey results further comprises how frequently the subject uses a rescue inhaler since receiving their last provision of the corticosteroid pharmaceutical composition, wherein a frequency with which the subject uses a rescue inhaler, which is capable of firing the asthma reduction filter, is more than twice a week.

22. The method of claim 18, wherein the re-fulfillment process further comprises, when a respective filter in the third plurality of filters or fourth plurality of filters is fired, storing a record associated with the firing of the respective filter in an adverse event profile comprising records of filter firing events associated with a plurality of users.

23. The method of claim 1, wherein the corticosteroid pharmaceutical composition is fluticasone propionate and wherein, upon satisfying the requirements of the survey, the subject is authorized for an over-the-counter dosage of between 88 mcg of fluticasone propionate and 176 mcg of fluticasone propionate twice daily.

24. The method of claim 1, wherein the corticosteroid pharmaceutical composition is beclomethasone dipropionate and wherein, upon satisfying the requirements of the survey, the subject is authorized for an over-the-counter dosage of between 40 mcg of beclomethasone dipropionate and 80 mcg of beclomethasone dipropionate twice daily.

25. The method of claim 1, wherein the corticosteroid pharmaceutical composition is ciclesonide and wherein, upon satisfying the requirements of the survey, the subject is authorized for an over-the-counter dosage of between 80 mcg of ciclesonide and 160 mcg of ciclesonide twice daily.

26. The method of claim 1, wherein the corticosteroid pharmaceutical composition is mometasone furoate and wherein, upon satisfying the requirements of the survey, the subject is authorized for an over-the-counter dosage of between 220 mcg of budesonide and 440 mcg of budesonide twice daily.

\* \* \* \* \*